US010071068B2

(12) United States Patent
Edgren et al.

(10) Patent No.: US 10,071,068 B2
(45) Date of Patent: Sep. 11, 2018

(54) SUSTAINED RELEASE ORAL DOSAGE FORMS OF AN R-BACLOFEN PRODRUG

(75) Inventors: David E. Edgren, Los Altos, CA (US); David J. Kidney, San Jose, CA (US); Nikhil Pargaonkar, Sunnyvale, CA (US); Derrick K. Kim, Issaquah, WA (US); Gorm Yoder, Oakland, CA (US); Sarni Karaborni, Cupertino, CA (US)

(73) Assignee: XENOPORT, INC., Santa Clara, CA (US)

(*) Notice: Subject to any disclaimer, the term of this patent is extended or adjusted under 35 U.S.C. 154(b) by 422 days.

(21) Appl. No.: 12/717,098

(22) Filed: Mar. 3, 2010

(65) Prior Publication Data
US 2010/0255093 A1 Oct. 7, 2010

Related U.S. Application Data

(60) Provisional application No. 61/157,114, filed on Mar. 3, 2009.

(51) Int. Cl.
*A61K 31/197* (2006.01)
*A61K 9/20* (2006.01)
*A61K 31/27* (2006.01)

(52) U.S. Cl.
CPC .......... *A61K 31/197* (2013.01); *A61K 9/2027* (2013.01); *A61K 9/2054* (2013.01); *A61K 9/2095* (2013.01); *A61K 31/27* (2013.01)

(58) Field of Classification Search
None
See application file for complete search history.

(56) References Cited

U.S. PATENT DOCUMENTS

| | | | |
|---|---|---|---|
| 4,126,684 A | 11/1978 | Robson et al. | |
| 5,006,560 A | 4/1991 | Kreutner et al. | |
| 5,719,185 A | 2/1998 | Bountra et al. | |
| 6,117,451 A * | 9/2000 | Kumar | 424/465 |
| 6,117,908 A | 9/2000 | Andrews et al. | |
| 6,733,782 B1 * | 5/2004 | Huet De Barochez et al. | 424/464 |
| 6,818,787 B2 | 11/2004 | Gallop et al. | |
| 6,927,036 B2 | 8/2005 | Gallop et al. | |
| 6,972,341 B2 | 12/2005 | Gallop et al. | |
| 6,992,076 B2 | 1/2006 | Cundy et al. | |
| 7,109,239 B2 * | 9/2006 | Gallop et al. | 514/533 |
| 7,186,855 B2 | 3/2007 | Gallop et al. | |
| 7,227,028 B2 | 6/2007 | Gallop et al. | |
| 7,232,924 B2 | 6/2007 | Raillard et al. | |
| 7,300,956 B2 | 11/2007 | Gallop et al. | |
| 7,511,158 B2 | 3/2009 | Gallop et al. | |
| 7,572,830 B2 | 8/2009 | Gallop et al. | |
| 7,662,987 B2 | 2/2010 | Bhat et al. | |
| 7,700,652 B2 | 4/2010 | Barrett et al. | |
| 2004/0254246 A1 | 12/2004 | Barrett et al. | |
| 2005/0154057 A1 | 7/2005 | Estrada et al. | |
| 2005/0192353 A1 | 9/2005 | Barrett et al. | |
| 2005/0220873 A1 | 10/2005 | Han et al. | |
| 2006/0099245 A1 * | 5/2006 | Kumar et al. | 424/451 |
| 2006/0141034 A1 | 6/2006 | Cundy et al. | |
| 2006/0229361 A1 | 10/2006 | Gallop et al. | |
| 2008/0058546 A1 | 3/2008 | Raillard et al. | |
| 2008/0096960 A1 | 4/2008 | Gallop et al. | |
| 2008/0161393 A1 | 7/2008 | Barrett et al. | |
| 2008/0188562 A1 | 8/2008 | Zerangue et al. | |
| 2008/0206332 A1 | 8/2008 | Kidney et al. | |
| 2009/0118365 A1 | 5/2009 | Benson et al. | |
| 2009/0192325 A1 | 7/2009 | Gallop et al. | |
| 2009/0197958 A1 | 8/2009 | Sastry et al. | |
| 2010/0081830 A1 | 4/2010 | Raillard et al. | |
| 2010/0087667 A1 | 4/2010 | Raillard et al. | |

FOREIGN PATENT DOCUMENTS

| | | |
|---|---|---|
| EP | 1178034 A1 | 2/2002 |
| WO | WO 91/08740 A1 | 6/1991 |
| WO | WO 01/08675 A1 | 2/2001 |
| WO | WO 01/26638 A2 | 4/2001 |
| WO | WO 01/90052 A1 | 11/2001 |
| WO | WO 02/096404 A1 | 12/2002 |
| WO | WO 05/019163 A2 | 3/2005 |
| WO | WO 05/097079 A1 | 10/2005 |
| WO | WO 08/011016 A1 | 1/2008 |
| WO | WO 08/086492 A1 | 7/2008 |
| WO | WO 08/157408 A2 | 12/2008 |
| WO | WO 09/096985 A1 | 8/2009 |

OTHER PUBLICATIONS

FDA, Bioavailability and Bioequivalence Studies for Orally Administered Drug Products—General Considerations, 2000, pp. 1-27.*
Pharmacopeial Forum, "Tablet Friability ", 2006, vol. No. 31(6) p. 1735.*
U.S. Appl. No. 61/309,336, filed Mar. 1, 2010, Win et al.
U.S. Appl. No. 12/024,830, filed Feb. 1, 2008, Sastry, et al.
Abrams et al., The standardisation of terminology of lower urinary tract function: report from the standardisation sub-committee of the International Continence Society. *Neurology and Urodynamics* (2002), 21:167-178.
Abrams, Describing bladder storage function: overactive bladder syndrome and detrusor overactivity. *Urology* (2003), 62 (Suppl 5B):28-37.
Addolorato et al., Baclofen efficacy in reducing alcohol craving and intake: a preliminary double-blind randomized controlled study. *Alcohol & Alcoholism* (2002), 37(5):504-508.
Ahmadi-Abhari et al., Baclofen versus clonidine in the treatment of opiates withdrawal, side-effects aspect: a double-blind randomized controlled trial. *J Clin Pharm Ther.* (2001), 26:67-71.

(Continued)

*Primary Examiner* — Michael G Hartley
*Assistant Examiner* — Lance W Rider
(74) *Attorney, Agent, or Firm* — King & Spalding LLP

(57) ABSTRACT

Sustained release oral dosage forms of an R-baclofen prodrug are disclosed.

12 Claims, 15 Drawing Sheets

(56) References Cited

OTHER PUBLICATIONS

American Society of Anesthesiologists, Practice guidelines for sedation and analgesia by non-anesthesiologists, *Anesthesiology* (2002), 96:1004-1017.
Andersson, The overactive bladder: pharmacologic basis of drug treatment. *Urology* (1997), 50(Suppl. 6A):74-84.
Anghinah et al., Effect of baclofen on pain in diabetic neuropathy, *Muscle & Nerve* (1994), 17(8):958-9.
Assadi et al., Baclofen for maintenance treatment of opioid dependence: a randomized double-blind placebo-controlled clinical trial. *BMC Psychiatry* (2003), 3(16) (10 pages).
Balerio et al., Baclofen analgesia: involvement of the GABAergic system, *Pharm. Res.* (2002), 46(3):281-286.
Becker et al., Intrathecal baclofen alleviates autonomic dysfunction in severe brain injury, *J Clin. Neurosci.* (2000), 7(4):316-319.
Bowery, $GABA_B$ receptors and their significance in mammalian pharmacology, *Trends Pharmacol. Sci.* (1989), 10:401-407.
Bowsher, Neurogenic pain syndromes and their management, *Br. Med. Bull.* (1991), 47(3):644-666.
Brebner et al., A potential role for $GABA_B$ agonists in the treatment of psychostimulant addiction, *Alcohol & Alcoholism* (2002), 37(5):478-484.
Castell et al., XP19986 decreases reflux and is well tolerated in GERD patients, *Am J. Gastroenterology* (2006), 101(suppl 2)(52):S59.
Castell et al., R-baclofen prodrug XP19986 decreases reflux episodes and is well tolerated in GERD patients, *Gastroenterology* (2007), 132(4)(suppl. A):A-486.
Cercos-Fortea, et al., Influence of leucine on intestinal baclofen absorption as a model compound of neutral α-aminoacids, *Biopharm. Drug Disp.* (1995), 16:563-577.
Chan et al., Action of anti-tussive drugs on the emetic reflex of *Suncus murinus* (house musk shrew), *Eur. J. Pharmacol.* (2007), 559:196-201.
Ciccaglione et al., Effect of acute and chronic administration of the $GABA_B$ agonist baclofen on 24 hour pH metry and symptoms in control subjects and in patients with gastro-oesophageal reflux disease, *Gut* (2003), 52:464-470.
Colli et al., Overactive bladder treatments in early phase clinical trials, *Expert Opin. Investig. Drugs* (2007), 16(7):999-1007.
Cousins et al., $GABA_B$ receptor agonists for the treatment of drug addiction: a review of recent findings. *Drug and Alcohol Depend.* (2002), 65:209-220.
Dapas et al., Baclofen for the treatment of acute low-back syndrome—a double-blind comparison with placebo. *Spine* 1985, 10(4):345-349.
Deguchi et al., Study on brain interstitial fluid distribution and blood-brain barrier transport of baclofen in rats by microdialysis, *Pharm. Res.* (1995), 12(12):1838-1844.
Dicpinigaitis et al., Antitussive effect of the GABA-agonist baclofen, *Chest* (1997), 111:996-999.
Dicpinigaitis et al., Treatment of chronic, refractory cough with baclofen, *Respiration* (1998), 65:86-88.
Dicpinigaitis et al., Inhibition of capsaicin-induced cough by the γ-aminobutyric acid agonist baclofen, *J Clin Pharmacol* (1998), 38:364-367.
Flannery et al., Baclofen for alcohol dependence: a preliminary open-label study, *Alcohol Clin. Exp. Res.* (2004), 28(10):1517-1523.
Freitag, Preventative treatment for migraine and tension-type headaches: do drugs having effects on muscle spasm and tone have a role?, *CNS Drugs* (2003), 17(6), 373-381.
Fromm et al., Role of inhibitory mechanisms in trigeminal neuralgia, *Neurology* (1981), 31:683-687.
Fromm et al., Baclofen in the treatment of trigeminal neuralgia: double-blind study and long-term follow-up, *Ann. Neurol.* (1984), 15:240-244.
Fromm et al., Comparison of L-baclofen and racemic baclofen in trigeminal neuralgia, *Neurology* (1987), 37:1725-1728.
Gatscher et al., Combined intrathecal baclofen and morphine infusion for the treatment of spasticity related pain and central deafferentiation pain. *Acta Neurochir* (2001), 79(Suppl):75-76.
Gerson et al., Arbaclofen Placarbil Decreases Postprandial Reflux in Patients With Gastroesophageal Reflux Disease, *Am J Gastroenterol.* (2010), 105:1266-1275.
Haney et al., Effects of baclofen on cocaine self-administration: opioid- and nonopioid-dependent volunteers. *Neuropsychopharmacology* (2006), 31:1814-21.
Heinzerling et al., Randomized, placebo-controlled trial of baclofen and gabapentin for the treatment of methamphetamine dependence, *Drug Alcohol Depend.* (2006), 85:177-184.
Hering-Hanit, Baclofen for prevention of migraine, *Cephalalgia* (1999), 19:589-591.
Hering-Hanit et al., Baclofen in cluster headache, *Headache* (2000), 40:48-51.
Herman et al., Intrathecal baclofen suppresses central pain in patients with spinal lesions. A pilot study, *Clin J Pain* (1992), 8:338-345.
Hornby et al., Central mechanisms of lower esophageal sphincter control, *Gastroenterol. Clin. N. Am.* (2002), 31(4 Suppl):S11-S20.
Hwang et al., The effect of spinal GABA receptor agonists on tactile allodynia in a surgically-induced neuropathic pain model in the rat, *Pain* (1997), 70:15-22.
Katz, Management of spasticity, *Am. J. Phys. Med. Rehab.* 1988, 67(3), 108-16.
Krach, Pharmacotherapy of spasticity: oral medications and intrathecal baclofen, *J. Child Neurol.* (2001), 16:31-36.
Kydonieus ed., Treatise on Controlled Drug Delivery, Fundamentals, Optimization, and Applications, Marcel Dekker, Inc. (1992) (6 pages).
Lal et al., Arbaclofen placarbil, a novel R-baclofen prodrug: improved absorption, distribution, metabolism, and elimination properties compared with R-baclofen. *J Pharmacology Experimental Therapeutics* (2009), 330:911-921.
Lidums et al., Control of transient lower esophageal sphincter relaxations and reflux by $GABA_B$ agonist baclofen in normal subjects. *Gastroenterology* (2000), 118:7-13.
Magora et al., Investigation of the clinical and electrophysiological effects of intrathecal baclofen in low back pain: preliminary results, *The Pain Clin.* (1988), 2(2):81-85.
Malcangio and Bowery, GABA and its receptors in the spinal cord. *Trends Pharmacol Sci* (1996), 17:457-462.
Markou et al., Role of γ-aminobutyric acid (GABA) and metabotropic glutamate receptors in nicotine reinforcement: potential pharmacotherapies for smoking cessation, *Ann N.Y. Acad. Sci.* (2004), 1025:491-503.
Meleger et al., Neck and back pain: musculoskeletal disorders, *Neurol. Clin.* (2007), 25:419-438.
Merino et al., Evidence of a specialized transport mechanism for the intestinal absorption of baclofen. *Biopharm. Drug. Disp.* (1989), 10:279-297.
Misgeld et al., A physiological role for $GABA_B$ receptors and the effects of baclofen in the mammalian central nervous system, *Prog. Neurobiol.* (1995), 46:423-462.
Moll-Navarro et al., Interaction of taurine on baclofen intestinal absorption: a nonlinear mathematical treatment using differential equations to describe kinetic inhibition models, *J. Pharm. Sci.* (1996), 85(11):1248-1254.
Ohtsuki et al., Role of blood-brain barrier organic anion transporter 3 (OAT3) in the efflux of indoxyl sulfate, a uremic toxin: its involvement in neurotransmitter metabolite clearance from the brain. *J. Neurochem.* (2002), 83:57-66.
Ouslander, Management of overactive bladder. *N. Engl J Med* (2004), 350:786-799.
Patel et al., The effects of $GABA_B$ agonists and gabapentin on mechanical hyperalgesia in models of neuropathic and inflammatory pain in the rat, *Pain* (2001), 90(3):217-26.
Price et al., Are baclofen-sensitive $GABA_B$ receptors present on primary afferent terminals of the spinal cord? *Nature* (1984), 307(5946):71-74.
Raphael et al., Long-term experience with implanted intrathecal drug administration systems for failed back syndrome and chronic mechanical low back pain, *BMC Musculoskeletal Disorders* (2002), 3(17): 1-8.

(56) References Cited

OTHER PUBLICATIONS

Raphael et al., Efficacy and adverse effects of intravenous lignocaine therapy in fibromyalgia syndrome. *BMC Musculoskeletal Disorders* (2002), 3(21):1-8.
Reis et al., Baclofen, an agonist at peripheral $GABA_B$ receptors, induces antinociception via activation of TEA-sensitive potassium channels, *Br J Pharmacol* (2006), 149(6):733-739.
Ringel et al., Glossopharyngeal neuralgia: successful treatment with baclofen, *Ann Neurol* (1987), 21(5):514-515.
Robinson et al., New drug treatments for urinary incontinence, *Maturitas* (2010), 65:340-347.
Sampathkumar et al., Baclofen withdrawal presenting as multiorgan system failure. *Anesth. Analg.* (1998), 87:562-563.
Sawynok et al., D-baclofen in an antagonist at baclofen receptors mediating antinociception in the spinal cord. *Pharmacology* (1985), 31:248-259.
Slonimski et al., Intrathecal baclofen in pain management, *Reg Anesth Pain Med* (2004), 29(3):269-276.
Smith et al., Increased sensitivity to the antinociceptive activity of (+/−)-baclofen in an animal model of chronic neuropathic, but not chronic inflammatory hyperalgesia, *Neuropharmacology* (1994), 33(9):1103-1108.
Suzuki et al., Effect of a selective $GABA_B$ receptor agonist baclofen on the μ-opioid receptor agonist-induced antinociceptive, emetic and rewarding effects, *Neuropharmacology* (2005), 49:1121-1131.
Taira et al., A new approach to control central deafferentation pain: spinal intrathecal baclofen. *Stereotactic Funct Neurosurg* (1995), 65:101-105.
Taylor et al., A double-blind crossover trial of baclofen—a new treatment for the unstable bladder syndrome. *British J Urology* (1979), 51:504-505.
Taylor-Gjevre et al., Anti-glutamic acid decarboxylase antibodies in a patient with systemic lupus erythematosus and fibromyalgia symptoms, *Lupus* (2005), 14:486-488.
Tyagi et al., $β_3$-adrenoceptor agonists for the treatment of overactive bladder, *Drugs of the Future* (2009), 34(8):635-640.
U.S. Food and Drug Administration, Dissolution Testing of Immediate Release Solid Oral Dosage Forms—Guidance for Industry, *FDA-CDER*, Aug. 1997 (17 pages).
U.S. Food and Drug Administration, Guidance for Industry—Bioavailability and Bioequivalence Studies for Orally Administered Drug Products, Revision 1, Mar. 2003 (26 pages).
Van Bree et al., Carrier-mediated transport of baclofen across monolayers of bovine brain endothelial cells in primary culture. *Pharm Res* (1988), 5(6):369-371.
Van Bree et al., Stereoselective transport of baclofen across the blood-brain barrier in rats as determined by the unit impulse response methodology. *Pharm Res* (1991), 8(2):259-262.
Van Herwaadren et al., The effect of baclofen on gastro-oesophageal reflux, lower oesophageal sphincter function and reflux symptoms in patients with reflux disease. *Aliment. Pharmacol. Ther.* (2002), 16:1655-1662.
Van Hilten et al., Intrathecal baclofen for the treatment of dystonia in patients with reflex sympathetic dystrophy. *N Engl J Med* (2000), 343:625-630.
Vatine et al., Effect of intrathecal baclofen in low back pain with root compression syndromes. *Pain Clin* (1988), 2(4):207-217.
Vela et al., Baclofen decreases acid and non-acid post-prandial gastro-oesophageal reflux measured by combined multichannel intraluminal impedance and pH. *Aliment Pharmacol Ther* (2003), 17:243-251.
Wall et al., Metabolism of 3-(ρ-chlorophenyl)pyrrolidine. Structural effects in conversion of a prototype γ-aminobutyric acid prodrug to lactam and γ-aminobutyric acid type metabolites. *J. Med. Chem.* (1989), 32:1340-1348.
Wein et al., Definition and epidemiology of overactive bladder. *Urology* (2002), 60(Suppl. 5A):7-12.
Wise ed., Handbook of Pharmaceutical Controlled Release Technology, Marcel Dekker, Inc. (2000) (8 pages).
Zhang et al., Control of transient lower oesophageal sphincter relaxations and reflux by the $GABA_B$ agonist baclofen in patients with gastro-oesophageal reflux disease. *Gut* (2002), 50:19-24.
Zuniga et al., Intrathecal baclofen is analgesic in patients with chronic pain. *Anesthesiology* (2000), 92:876-880.
Zuniga et al., Intrathecal baclofen: a useful agent in the treatment of well-established complex regional pain syndrome. *Reg Anesth Pain Med* (2002), 27:90-93.
International Search Report and Written Opinion of the International Searching Authority dated Jun. 13, 2008, for International Application No. PCT/US2008/050796 filed Jan. 10, 2008 (13 pages).
International Preliminary Report on Patentability dated Jul. 14, 2009, for International Application No. PCT/US2008/050796 filed Jan. 10, 2008 (9 pages).
International Search Report and Written Opinion of the International Searching Authority dated Jun. 13, 2008 for International Application No. PCT/US2008/052808, filed Feb. 1, 2008 (15 pages).
Non-final Office Action dated Sep. 2, 2010, for U.S. Appl. No. 11/972,575, filed Jan. 10, 2008 (14 pages).
Final Office Action dated Jun. 15, 2007 for U.S. Appl. No. 11/145,159, filed Jun. 3, 2005 (8 pages).
Notice of Allowance dated Oct. 10, 2007 for U.S. Appl. No. 11/145,159, filed Jun. 3, 2005 (6 pages).
Notice of Allowance and Examiner's Amendment dated Jan. 23, 2008, in U.S. Appl. No. 11/145,159, filed Jun. 3, 2005 (5 pages).
Notice of Allowance, Notice of Allowability, and Examiner's Amendment dated Sep. 11, 2007, for U.S. Appl. No. 11/145,280, filed Jun. 3, 2005 (8 pages).
International Search Report and Written Opinion of the International Searching Authority dated Jul. 15, 2010, for International Application No. PCT/US2010/026133 filed Mar. 3, 2010 (10 pages).
Dow Wolff Cellulosics, "Indroducing METHOCEL DC Grade Hypromellose Polymers for Direct Compression of Controlled Release Dosage Forms," Oct. 2008, 8 pages.
Abdelkader et al., Formulation of Controlled-Release Baclofen Matrix Tablets: Influence of Some Hydrophilic Polymers on the Release Rate and In Vitro Evaluation, 8 AAPS Pharm SciTech E1-E11, E4 (2007).
Gennaro; Remington: The Science and Practice of Pharmacy, $20^{th}$ Edition; "Physiochemical Properties: Aqueous Solubility and pKa"; Daniel Limmer, Editor; 2000, 3 pages.

\* cited by examiner

1A

1B

1C

2A

2B

2C

SUSTAINED RELEASE ORAL DOSAGE FORMS OF AN R-BACLOFEN PRODRUG

This application claims the benefit of U.S. Provisional Patent Application No. 61/157,114 filed Mar. 3, 2009, which is incorporated by reference herein for all purposes.

FIELD

Methods provided by the present disclosure relate to sustained release oral dosage forms of an (R)-baclofen prodrug.

BACKGROUND (3R)-4-{[(1S)-2-Methyl-1-(2-methylpropanoyloxy)propoxy]carbonylamino}-3-(4-chlorophenyl)butanoic acid (1),

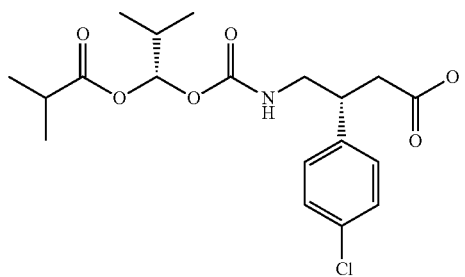

a prodrug of the GABA$_B$ agonist, R-baclofen((±)-4-amino-3-(4-chlorophenyl)butanoic acid), exhibits high bioavailability as R-baclofen when dosed either orally or directly into the colon of a mammal (Gallop et al., U.S. Pat. Nos. 7,109,239 and 7,227,028; and Lal et al., *J Pharmacology Experimental Therapeutics* 2009, 330(3), 911-921).

The high R-baclofen oral bioavailability following administration of compound (1) favors the use of compound (1) in oral dosage forms, including sustained-release oral dosage forms, and the use of such oral dosage forms for treating diseases such as spasticity and gastro-esophageal reflux disease (van Herwaarden et al., *Aliment. Pharmacol. Ther.* 2002, 16(9), 1655-62; Ciccaglione and Marzio, *Gut* 2003, 52(4), 464-70; Andrews et al., U.S. Pat. No. 6,117,908; and Fara et al., WO 02/096404); in promoting alcohol abstinence in alcoholics (Gessa et al., WO 01/26638); in promoting smoking cessation (Gessa et al., WO 01/08675); in reducing addiction liability of narcotic agents (Robson et al., U.S. Pat. No. 4,126,684); in the treatment of emesis (Bountra et al., U.S. Pat. No. 5,719,185); as an anti-tussive for the treatment of cough (Kreutner et al., U.S. Pat. No. 5,006,560); as well as for treating neuropathic and musculoskeletal pain (Benson et al., US 2009/0118365), urinary incontinence (Wun and Wustrow, U.S. Provisional Application Ser. No. 61/309,336, filed Mar. 1, 2010), movement disorders such as dystonia and hiccups; peripheral nerve disorders such as muscle stimulation disorders; spinal cord disorders such as spastic paraparesis; cranial nerve disorders such as glossopharyngeal neuralgia and trigeminal neuralgia; multiple sclerosis; and cerebral palsy.

The synthesis of compound (1) is described by Gallop et al., U.S. Pat. No. 7,109,239; Gallop et al., U.S. Pat. No. 7,227,028; Gallop et al., US 2009/0192325; Raillard et al., U.S. application Ser. No., 12/537,798 filed Aug. 7, 2009; and Raillard et al., U.S. application Ser. No. 12/537,764 filed Aug. 7, 2009, each of which is incorporated herein by reference in its entirety.

Oral dosage forms comprising compound (1) are disclosed in Kidney et al., US 2008/0206332; and Sastry et al., US 2009/0197958. Kidney et al. disclose sustained release tablet dosage forms comprising compound (1) and a release rate-controlling polymer prepared using high shear wet granulation. Sastry et al. disclose sustained release particulate dosage forms comprising compound (1).

In the direct compression tablet manufacturing process, tablet components are combined by dry blending and the resulting dry blend is subsequently combined into tablets with punch tooling on a rotary tablet press. Previous matrix tablet formulations of compound (1) required the use of organic solvents such as alcohols during the high shear wet granulation process in order to form free-flowing granulations (Kidney et al., US 2008/0206332). Free-flowing granulations are required in manufacturing processes to maintain acceptable weight control on rotary tablet presses. Solvents used in the high shear wet granulation process must subsequently be removed to acceptable levels by drying at elevated temperature, which increases manufacturing costs and slows the production rate.

SUMMARY

Thus, improved methods for preparing oral dosage forms of (3R)-4-{[(1S)-2-methyl-1-(2-methylpropanoyloxy)propoxy]carbonylamino}-3-(4-chlorophenyl)butanoic acid are useful.

Oral tablet dosage forms comprising (3R)-4-{[(1S)-2-methyl-1-(2-methylpropanoyloxy)propoxy]carbonylamino}-3-(4-chlorophenyl)butanoic acid prepared from dry powders and methods of preparing such dosage forms are disclosed. Dry processing eliminates exposure of the drug to water or to solvents that may cause chemical degradation. Additionally, dry processing can be performed at room temperature. This benign temperature condition can minimize or prevent thermal decomposition that may occur when the drug is exposed for prolonged periods of time to the elevated temperatures typically used to remove residual solvents introduced during wet granulation processing.

In a first aspect, oral tablet dosage forms are disclosed comprising about 3 wt-% to about 20 wt-% (3R)-4-{[(1S)-2-methyl-1-(2-methylpropanoyloxy)propoxy]carbonylamino}-3-(4-chlorophenyl)butanoic acid or a pharmaceutically acceptable salt thereof; about 15 wt-% to about 40 wt-% microcrystalline cellulose; about 15 wt-% to about 40 wt-% hydroxypropylmethyl cellulose; and about 3 wt-% to about 30 wt-% of a release rate-controlling polymer; wherein wt-% is based on the total weight of the dosage form.

In a second aspect, methods of preparing oral tablet dosage forms are disclosed comprising
dry blending a mixture comprising about 3 wt-% to about 20 wt-% (3R)-4-{[(1S)-2-methyl-1-(2-methylpropanoyloxy)propoxy]carbonylamino}-3-(4-chlorophenyl)butanoic acid or a pharmaceutically acceptable salt thereof; about 15 wt-% to about 40 wt-% microcrystalline cellulose; about 15 wt-% to about 40 wt-% hydroxypropylmethyl cellulose; and about 3 wt-% to about 30 wt-% of a release rate-controlling polymer; wherein wt-% is based on the total weight of the dosage form; and compacting the blended mixture to provide an oral tablet dosage form.

In a third aspect, methods of preparing oral tablet dosage forms are disclosed comprising blending dicalcium phosphate and (3R)-4-{[(1S)-2-methyl-1-(2-methylpropanoyloxy)propoxy]carbonylamino}-3-(4-chlorophenyl)butanoic acid or a pharmaceutically acceptable salt thereof to provide a first blend; passing the first blend through a cone mill; dry blending hydroxypropylmethyl cellulose and colloidal silicon dioxide to form a second blend; passing the second blend through a cone mill; blending the first blend, the second blend, microcrystalline cellulose, and a release rate-controlling polymer in a high shear blender to form a third blend; blending magnesium stearate with the third blend; and compacting the third blended to provide an oral tablet dosage form.

In a fourth aspect, methods of treating a disease in a patient are disclosed wherein the disease is chosen from spasticity, gastro-esophageal reflux disease, emesis, cough, narcotic addiction or abuse, alcohol addiction or abuse, nicotine addiction or abuse, neuropathic pain, and musculoskeletal pain, comprising orally administering to a patient in need of such treatment at least one oral tablet dosage form provided by the present disclosure.

BRIEF DESCRIPTION OF THE DRAWINGS

Those skilled in the art will understand that the drawings, described herein, are for illustration purposes only. The drawings are not intended to limit the scope of the present disclosure.

DETAILED DESCRIPTION

Definitions

Figure 1:
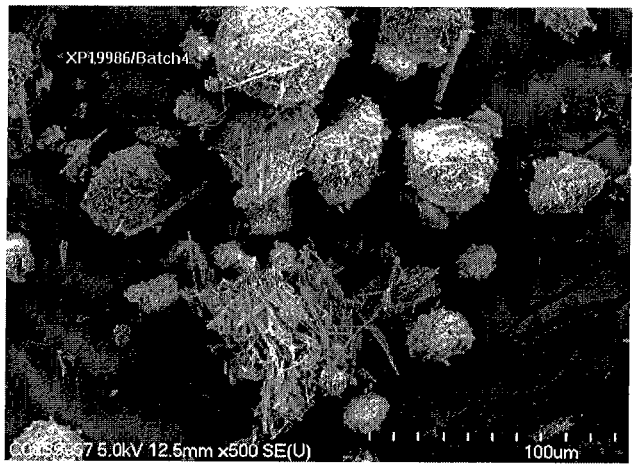
FIG. 1 shows scanning electron microscopy (SEM) micrographs of three lots of compound (1) at 500× magnification: Lot 4 (1A); Lot 70 (1B); Lot 71 (1C).
Figure 1:
Figure 1:
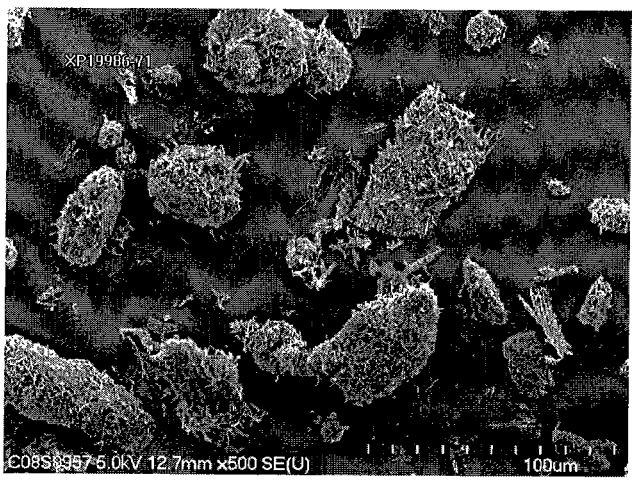

"Adverse drug effects" refers to drug effects that are unwanted, unpleasant, noxious, or potentially harmful. Adverse drug effects can be mild, moderate or severe. Examples of mild adverse drug effects include, without limitation, digestive disturbance, headaches, fatigue, vague muscle aches, malaise, and changes in sleep patterns. Moderate adverse drug effects represent reactions that a person experiencing them considers annoying, distressing, or intolerable such as, for example, skin rashes, visual disturbances, muscle tremor, difficulty with urination, perceptible changes in mood or mental function, and certain changes in blood components. Examples of severe adverse drug effects include reactions that may be life threatening, that result in persistent or significant disability or hospitalization, and that cause a birth defect. Examples of adverse effects known to be associated with baclofen therapy include sedation, impairment of cognitive function, confusion, memory loss, dizziness, weakness, ataxia, blurred or double vision, nausea, shortness of breath, convulsions, and orthostatic hypotension.

"AUC" is the area under a curve representing the concentration of a compound or metabolite thereof in the blood of a patient as a function of time following administration of the compound to the patient. For example, the administered compound can be the R-baclofen prodrug (1) and the corresponding metabolite R-baclofen. The AUC may be determined by measuring the concentration of a compound or metabolite thereof in blood using standard methods for measuring such as, for example, liquid chromatography-tandem mass spectrometry (LC/MS/MS), at various time intervals, and calculating the area under the blood concentration-versus-time curve. The concentration versus time curve is also referred to as the pharmacokinetic profile. Suitable methods for calculating the AUC from a drug concentration-versus-time curve are well known in the art. For example, an AUC for R-baclofen may be determined by measuring the concentration of R-baclofen in the blood of a patient following administration of an R-baclofen prodrug, such as compound (1), to the patient. $AUC_{0-24}$ is the area under the curve from administration (time 0) to 24 hours following administration. $AUC_{ss,24}$ is the area under the curve over a 24 hour period following a dosing regimen administered over a period of days (steady state).

"Bioavailability" refers to the rate and amount of R-baclofen that reaches the systemic circulation of a patient following administration of the compound (1) to the patient and can be determined by evaluating, for example, the blood concentration-versus-time profile for R-baclofen. Parameters useful in characterizing a blood concentration-versus-time curve include the area under the curve (AUC), the time to peak concentration ($T_{max}$), and the maximum R-baclofen concentration ($C_{max}$), where $C_{max}$ is the maximum concentration of a drug in the blood of a patient following administration of a dose of compound (1) to the patient, and $T_{max}$ is the time to the maximum concentration ($C_{max}$) of R-baclofen in the blood of a patient following administration of a dose of compound (1) to the patient.

Absolute oral bioavailability is the bioavailability of a compound or metabolite thereof following oral administration compared to the bioavailability following intravenous administration of an equivalent amount of the compound or metabolite thereof. Relative oral bioavailability of a compound or metabolite thereof is the bioavailability following oral administration of a compound or metabolite thereof relative to administration of an equivalent amount of the compound or metabolite thereof in another dosage form and/or route of administration. For example, in certain embodiments, relative oral bioavailability expressed as % $F_{rel}$ is the bioavailability of R-baclofen determined by the $AUC_{0-24}$ following oral administration of compound (1) to a patient relative to the bioavailability of R-baclofen following oral administration of 20 mg compound (1) as a sustained release dosage form.

"Bioequivalence" refers to equivalence of the rate and extent of absorption of R-baclofen after administration of equal doses of R-baclofen or compound (1) to a patient. As used herein, two pharmacokinetic profiles are bioequivalent if the 90% confidence interval for the ratio of the mean response of the two profiles is within the limits of 0.8 and 1.25. The mean response includes at least one of the characteristic parameters of a profile such as $C_{max}$, $T_{max}$, and AUC.

"Compound (1)" includes the R-baclofen prodrug compound (1), (3R)-4-{[(1S)-2-methyl-1-(2-methylpropanoyloxy)propoxy]carbonylamino}-3-(4-chlorophenyl)butanoic acid, pharmaceutically acceptable salts thereof, pharmaceutically acceptable solvates of any of the foregoing, and crystalline forms of any of the foregoing. Compound (1) is used interchangeably with R-baclofen prodrug (1). In certain embodiments, R-baclofen prodrug compound (1), (3R)-4-{[(1S)-2-methyl-1-(2-methylpropanoyloxy)propoxy]carbonylamino}-3-(4-chlorophenyl)butanoic acid, is the free acid. In certain embodiments, R-baclofen prodrug compound (1), (3R)-4-{[(1S)-2-methyl-1-(2-methylpropanoyloxy)propoxy]carbonylamino}-3-(4-chlorophenyl)butanoic acid, is the free acid and is crystalline. In certain embodiments, R-baclofen prodrug compound (1), (3R)-4-{[(1S)-2-methyl-1-(2-methylpropanoyloxy)propoxy]carbonylamino}-3-(4-chlorophenyl)butanoic acid, is the hydrochloride salt. Using IUPAC nomenclature, compound (1) may also be referred to as (R)-4-chloro-β-[[[[2-methyl-1-(S)-(2-methyl-1-oxopropoxy)propoxy]carbonyl]amino]methyl]-benzenepropanoic acid.

Compound (1) may also exist in several tautomeric forms including the enol form, the keto form, and mixtures thereof. Accordingly, the chemical structures depicted herein encompass all possible tautomeric forms of the illustrated compounds. Compounds of the present disclosure also include isotopically labeled compounds where one or more atoms have an atomic mass different from the atomic mass conventionally found in nature. Examples of isotopes that may be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compound (1) may exist in unsolvated forms as well as solvated forms, including hydrated forms and as N-oxides. In general, compounds as referred to herein may be salts, free acid, hydrated, solvated, N-oxides or combinations of any of the foregoing. Compound (1) may exist in multiple crystalline, co-crystalline, or amorphous forms. Compound (1) includes pharmaceutically acceptable salts thereof, or pharmaceutically acceptable solvates of the free acid form of any of the foregoing, as well as crystalline forms of any of the foregoing.

Compound (1) also includes solvates. A solvate refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Compounds" of the present disclosure include any specific compounds within the formulae disclosed herein. Compounds may be identified either by their chemical structure and/or chemical name. When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, unless specifically indicated, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to those skilled in the art. For example, resolution of the enantiomers or diastereomers may be accomplished, for example, by conventional methods such as crystallization in the presence of a resolving agent, or chromatography, using, for example, a chiral high-pressure liquid chromatography (HPLC) column.

"$C_{max}$" is the maximum R-baclofen concentration observed in the blood of a patient following administration of a dose of compound (1) to the patient. $C_{ss,max}$ is the maximum steady state concentration following administration of compound (1) during a dosing regimen administered over a period of days (steady state). $C_{ss,min}$ is the minimum concentration at steady state.

"$C_{12}$" is the R-baclofen concentration observed in the blood of a patient twelve (12) hours after administration of compound (1) to the patient. $C_{ss,12}$ is the concentration 12 hours following administration of compound (1) during a dosing regimen administered over a period of days (steady state).

"$T_{max}$" is the time to the maximum concentration ($C_{max}$) of R-baclofen in the blood of a patient following administration of a dose of compound (1) to the patient. $T_{ss,max}$ is the time to maximum concentration following administration of compound (1) during a dosing regimen administered over a period of days (steady state).

"$T_{1/2}$" is the time interval between $T_{max}$ and the time at which the R-baclofen concentration in the blood of a patient has decreased to one-half the maximum drug concentration. $T_{ss,1/2}$ is the time interval between $T_{max}$ and the time at which the R-baclofen concentration in the blood of a patient has decreased to one-half the maximum drug concentration following administration of compound (1) during a dosing regimen administered over a period of days (steady state).

"Dosage form" refers to a form of a formulation that contains an amount of active agent or prodrug of an active agent, i.e., R-baclofen prodrug (1), which can be administered to a patient to achieve a therapeutic effect. An oral dosage form is intended to be administered to a patient via the mouth and swallowed. A dose of a drug may include one or more dosage forms administered simultaneously or over a period of time.

"Fasted patient" refers to a patient whose stomach is substantially free of food at the time a dose is administered to the patient and for at least 4 hours following administration. The time at which a patient's stomach becomes substantially free of food following a meal can depend on a number of factors including, for example, the size of the meal such as the number of calories, the content of the meal such as the fat content, the health of the patient, and the condition of the patient's gastrointestinal tract. The stomach of a healthy human subject is typically substantially free of food after about 4 hours to about 8 hours following ingestion of food. In certain embodiments, a fasted patient does not eat any food (but can ingest any amount of water or clear liquid) from about 10 hours prior to dosing until about 4 hours after dosing, drinks about 250 mL of water about 2 hours and about 1 hour prior to dosing, and about 250 mL of water about 2 hours after dosing, eats a lunch about 4 hours after dosing, and eats a dinner about 10 hours after dosing.

"Fed patient" refers to a patient whose stomach contains food. In certain embodiments, a fed patient begins eating a test meal about 30 minutes prior to dosing and completes eating the test meal about 5 minutes prior to dosing, eats a lunch 4 hours after dosing, and eats a dinner about 10 hours after dosing. A test meal may comprise a high fat (about 50% of the total number of calories in the test meal) and high calorie (about 1000 total calories) breakfast such as, for example, 2 eggs fried in butter, 2 strips of bacon, 2 slices of wheat toast with butter, 4 ounces of hash brown potatoes, and 8 ounces of whole milk. A test meal may contain any number of calories and, in some embodiments, contains about 150 protein calories, 250 carbohydrate calories, and about 500 to 600 fat calories.

"Minimum adverse concentration" refers to the minimum concentration of a therapeutic compound in, for example, the blood or plasma of a patient, which does not produce an unacceptable adverse drug effect. The unacceptability of an adverse drug effect can be determined, for example, by the patient and/or by the prescribing physician based at least in part on the severity of the adverse drug effect and/or the perceived risk in view of the therapeutic benefits of the compound being administered to the patient. The minimum adverse concentration may also depend, at least in part, on the age, weight and health of the patient being treated, the disease being treated, the frequency and severity of the symptoms, and the judgment of the prescribing physician.

"Minimum therapeutically effective concentration" refers to the minimum concentration of a therapeutic compound in, for example, the blood or plasma of a patient that produces an intended therapeutic effect.

"Patient" includes mammals such as, for example, humans.

"Pharmaceutically acceptable" refers to approved or approvable by a regulatory agency of a federal or a state government, listed in the U.S. Pharmacopeia, or listed in other generally recognized pharmacopeia for use in mammals, including humans.

"Pharmaceutically acceptable salt" refers to a salt of a compound such as compound (1) that is pharmaceutically acceptable and that possesses the desired pharmacological activity of the parent compound. Such salts include, without limitation: (a) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (b) salts formed when an acidic proton present in the parent compound either is replaced by a metal ion, e.g., an alkali metal ion, an alkaline earth metal ion, or an aluminum ion; or coordinates with an organic base such as ethanolamine, diethanolamine, triethanolamine, N-methylglucamine, and the like. In certain embodiments, a salt of compound (1) is the hydrochloride salt, and in certain embodiments, the sodium salt.

"Pharmaceutically acceptable vehicle" or "pharmaceutically acceptable excipient" refers to a pharmaceutically acceptable diluent, a pharmaceutically acceptable adjuvant, a pharmaceutically acceptable excipient, a pharmaceutically acceptable vehicle, a pharmaceutically acceptable carrier, or a combination of any of the foregoing with which a compound such as the R-baclofen prodrug, (3R)-4-{[(1S)-2-methyl-1-(2-methylpropanoyloxy)propoxy]carbonylamino}-3-(4-chlorophenyl)butanoic acid (1), may be administered to a patient, which does not destroy the pharmacological activity thereof, and which is nontoxic when administered in doses sufficient to provide a therapeutically effective amount of the compound, such as the R-baclofen prodrug or R-baclofen metabolite.

"Pharmaceutical composition" refers to a composition comprising the R-baclofen prodrug (1) or a pharmaceutically acceptable salt thereof and at least one pharmaceutically acceptable vehicle, with which the prodrug is to be administered to a patient.

"Prodrug" refers to a derivative of an active compound (drug) that undergoes a transformation under the conditions of use, such as within the body, to release an active drug. Prodrugs are frequently, but not necessarily, pharmacologically inactive until converted into the active drug. Prodrugs can be obtained by bonding a promoiety (defined herein), typically via a functional group, to a drug. For example, R-baclofen prodrug (1) is metabolized within a patient's body to provide the parent drug R-baclofen.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. For example, for R-baclofen prodrug (1), the drug is R-baclofen and the promoiety has the structure:

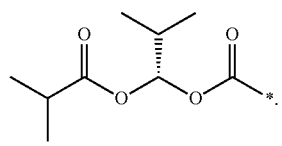

"Sedation" as used herein refers to minimal sedation and/or moderate sedation (see e.g., American Society of Anesthesiologists, *Anesthesiology* 2002, 96, 1004-17). Minimal sedation, also referred to as anxiolysis, is a minimally depressed level of consciousness that retains a patient's ability to independently and continuously maintain an airway and respond appropriately to physical stimulation or verbal command that is produced by a pharmacological or non-pharmacological method or combination thereof. Although cognitive function and coordination may be modestly impaired, ventilatory and cardiovascular functions are unaffected. When the intent is minimal sedation in adults, the appropriate dosing is no more than the maximum recommended dose that can be prescribed for unmonitored home use, e.g., a maximum recommended therapeutic dose. Moderate sedation is a drug-induced depression of consciousness during which patients respond purposefully to verbal commands, either alone or accompanied by light tactile stimulation. No intervention is required to maintain a patient's airway. Sedation is a continuum and it is not always possible to predict how an individual patient will respond. A sedative dose can be determined by incremental dosing, administering multiple doses of a drug, such as R-baclofen prodrug (1), until a desired effect is achieved. A variety of scales can be used to assess sedation including, for example, the Ramsay scale, and others. Objective measures of sedation include measurement of electroencephalogram parameters such as the Bispectral Index version XP and the Patient State Analyzer. In certain embodiments, sedation refers to minimal sedation, and in certain embodiments, to moderate sedation.

"Sustained release" refers to release of a compound from a dosage form at a rate effective to achieve a therapeutic amount of the compound, or active metabolite thereof, in the systemic blood circulation over a prolonged period of time relative to that achieved by oral administration of an immediate formulation of the compound. In some embodiments, in vivo release of the compound occurs over a period of at least about 4 hours, in some embodiments, over a period of at least about 8 hours, in some embodiments over a period of at least about 12 hours, in some embodiments, over a period of at least about 16 hours, in some embodiments, over a period of at least about 20 hours, and in some embodiments, over a period of at least about 24 hours. In certain embodiments, a sustained release dosage form provided by the present disclosure releases from about 45% to about 55% of compound (1) in the dosage form within about 18 hours; from about 40% to about 50% of compound (1) within about 18 hours; and in certain embodiments, from about 34% to about 44% of compound (1) is released within about 18 hours; in 50 mM sodium phosphate monobasic buffer at pH 6.8 and 37° C. stirred with a paddle rotating at a specified speed such as at 75 rpm (USP, Type II).

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. The therapeutically effective amount may vary depending, for example, on the compound, the disease, disorder, and/or symptoms of the disease, severity of the disease or disorder, and/or symptoms of the disease or disorder, the age, weight, and/or health of the patient to be treated, and the judgment of the prescribing physician. A therapeutically effective amount may be ascertained by those skilled in the art or determined by routine experimentation.

"Treating" or "treatment" of any disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease, or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease even though that patient does not yet experience or display symptoms of the disease.

Reference is now made in detail to certain embodiments of dosage forms and methods. The disclosed embodiments are not intended to be limiting of the claims. To the contrary, the claims are intended to cover all alternatives, modifications, and equivalents.

In one aspect, the present disclosure relates to the compound (3R)-4-{[(1S)-2-methyl-1-(2-methylpropanoyloxy) propoxy]carbonylamino}-3-(4-chlorophenyl)butanoic acid, having the following structure:

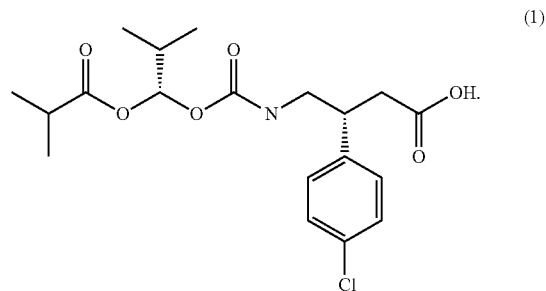 [SMILES: CC(C)C(=O)O[C@@H](OC(=O)NC[C@H](CC(=O)O)c1ccc(Cl)cc1)C(C)C]

(1)

Compound (1) is a prodrug of R-baclofen.

Composition

Figure 2:
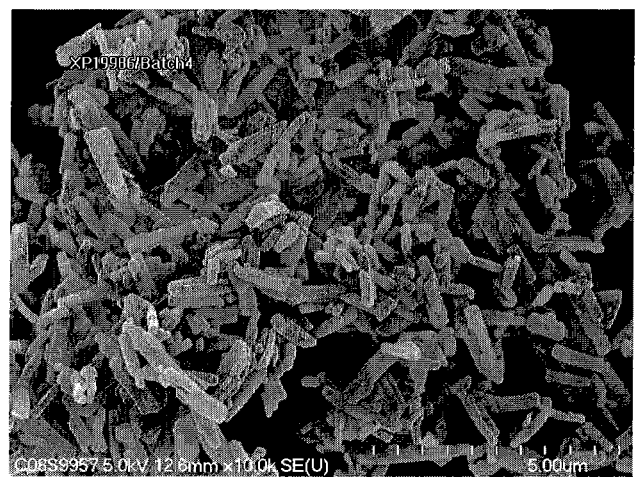
FIG. 2 shows SEM micrographs of three lots of compound (1) at 10,000× magnification: Lot 4 (2A); Lot 70 (2B); Lot 71 (2C).
Figure 2:
Figure 2:
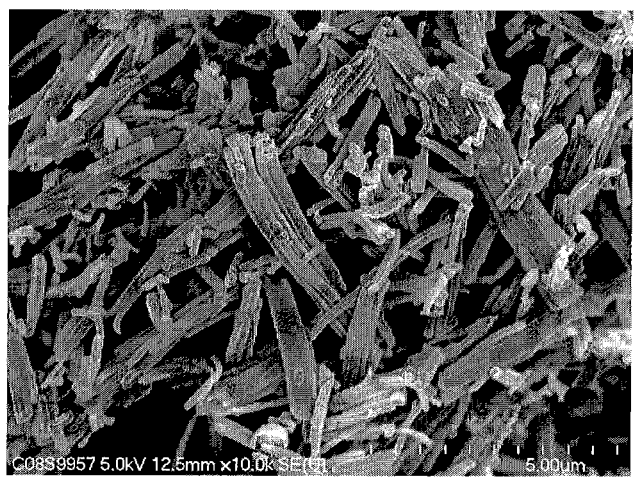

In another aspect, the present disclosure provides sustained release oral dosage forms that comprise (3R)-4-{[(1S)-2-methyl-1-(2-methylpropanoyloxy)propoxy]carbonylamino}-3-(4-chlorophenyl)butanoic acid and pharmaceutically acceptable excipients. Compound (1) may be prepared using the methods described by Gallop et al., U.S. Pat. No. 7,109,239; Gallop et al., U.S. Pat. No. 7,227,028; Gallop et al., US 2009/0192325; Raillard et al., U.S. application Ser. No., 12/537,798 filed Aug. 7, 2009; and/or Raillard et al., U.S. application Ser. No. 12/537,764 filed Aug. 7, 2009, the entire contents of which are incorporated by reference. In another aspect, crystallization of compound (1) provides products having different morphologies depending at least in part on the composition of the solvent or solvents and the rate of crystallization. Some of the different morphologies of compound (1) crystallized from acetone/hexane mixtures at different crystallization rates are shown in FIG. 1 and FIG. 2. The morphology obtained at an intermediate rate of crystallization (FIG. 1A and FIG. 2A) can be characterized as comprising aggregates of primary crystals of compound (1), which aggregates are predominantly rounded and compact with a diameter from about 25 microns to about 50 microns, and with the primary crystals having dimensions of less than a few microns. The morphology obtained at a slow rate of crystallization (FIG. 1B and FIG. 2B) can be characterized as comprising loose fibrous or filamentous masses with overall dimensions of about 100 microns, and with filaments about 100 μm in length. The morphology of compound (1) obtained at a fast rate of crystallization (FIG. 1C and FIG. 2C) can be characterized by irregularly shaped aggregates of primary crystals, where the aggregates have dimensions of about 25 microns to about 50 microns in length/width and with the primary crystals having dimensions of less than a few microns.

In another aspect, in addition to compound (1), sustained release oral dosage forms provided by the present disclosure may comprise pharmaceutically acceptable excipients such as microcrystalline cellulose, hydroxypropylmethyl cellulose, a release-rate controlling polymer, dibasic calcium phosphate dihydrate, colloidal silicon dioxide, and magnesium stearate.

In another aspect, in addition to compound (1), sustained release oral dosage forms provided by the present disclosure can comprise pharmaceutically acceptable excipients such as microcrystalline cellulose, hydroxypropylmethyl cellulose, a release-rate controlling polymer, dibasic calcium phosphate anhydrous, colloidal silicon dioxide, and magnesium stearate.

In certain embodiments, the microcrystalline cellulose used in dosage forms provided by the present disclosure can be characterized by a nominal particle size of about 180 microns, a moisture content of about 2% to about 5%, and a loose bulk density of about 0.29 g/cc to about 0.36 g/cc, such as for example AVICEL® PH200 (AVICEL®, FMC Biopolymer). In certain embodiments, the microcrystalline cellulose exhibits a Flodex of about 12 mm.

In certain embodiments, the hydroxypropylmethyl cellulose used in dosage forms provided by the present disclosure can be hypromellose 2208 having a 19-24% methoxyl content, a 7-12% hydroxypropyl content, and a viscosity of 3,000-5,600 cP in a 2% aqueous solution, such as for example, METHOCEL™ K4M SP (standard premium) or METHOCEL™ K4M CR (controlled release). In certain embodiments, the hydroxypropylmethyl cellulose used in dosage forms provided by the present disclosure can have a 19-24% methoxyl content, a 7-12% hydroxypropyl content, a hypromellose 2208 substitution type, a viscosity of 2,663-4,970 cP, a bulk density of 0.1-0.2 g/cc, and a moisture content of about 5% maximum, such as for example, METHOCEL™ K4M DC (direct compression). In certain embodiments, the hydroxypropylmethyl cellulose exhibits a Flodex from about 28 mm to about 30 mm.

In certain embodiments, the release rate controlling polymer used in dosage forms provided by the present disclosure can be a copolymer of ethyl acrylate, methyl methacrylate and a low content of a methacrylic acid ester with quarternary ammonium groups such as trimethylammonioethyl methacrylate chloride. In certain embodiments, the copolymer has an average molecular weight of about 150,000 Daltons. In certain embodiments, the release rate controlling copolymer contains about 8.9% to about 12.3% ammonio methacrylate units on the dry substance, and in certain embodiments, can be EUDRAGIT® RLPO (Evonik Industries AG, Darmstadt, Del.). In certain embodiments, the release rate controlling copolymer contains about 4.5% to about 7.0% ammonio methacrylate units on the dry substance, and in certain embodiments, can be EUDRAGIT® RSPO (Evonik Industries AG, Darmstadt, Del.). In certain embodiments, the release rate controlling polymer exhibits a Flodex of about 22 mm.

In certain embodiments, the dibasic calcium phosphate dihydrate used in dosage forms provided by the present disclosure can be DI-TAB®, which is unmilled. In certain embodiments, the dibasic calcium phosphate dihydrate exhibits a Flodex less than or equal to 4 mm.

In certain embodiments, the dibasic calcium phosphate anhydrous used in dosage forms provided by the present disclosure can be A-TAB®, which is unmilled. In certain embodiments, the dibasic calcium phosphate anhydrous exhibits a Flodex less than or equal to 4 mm.

In certain embodiments, the colloidal silicon dioxide or untreated fumed amorphous silica used in dosage forms provided by the present disclosure can be CAB-O-SIL™ M-5P (Cabot Corporation, Bilerica, Mass.).

In certain embodiments, sustained release oral dosage forms comprise about 3 wt-% to about 20 wt-% (3R)-4-{[(1S)-2-methyl-1-(2-methylpropanoyloxy)propoxy]carbonylamino}-3-(4-chlorophenyl)butanoic acid or a pharmaceutically acceptable salt thereof; about 15 wt-% to about 40 wt-% microcrystalline cellulose; about 15 wt-% to about 40 wt-% hydroxypropylmethyl cellulose; and about 3 wt-% to about 30 wt-% of a release rate-controlling polymer; wherein wt-% is based on the total weight of the dosage form. In certain embodiments, sustained release oral dosage forms comprise about 5 wt-% to about 15 wt-% (3R)-4-{[(1S)-2-methyl-1-(2-methylpropanoyloxy)propoxy]carbonylamino}-3-(4-chlorophenyl)butanoic acid or a pharmaceutically acceptable salt thereof; about 17 wt-% to about 33 wt-% microcrystalline cellulose; about 20 wt-% to about 35 wt-% hydroxypropylmethyl cellulose; and about 5 wt-% to about 20 wt-% of a release rate-controlling polymer; wherein wt-% is based on the total weight of the dosage form. In certain embodiments, sustained release oral dosage forms comprise about 8 wt-% to about 12 wt-% (3R)-4-{[(1S)-2-methyl-1-(2-methylpropanoyloxy)propoxy]carbonylamino}-3-(4-chlorophenyl)butanoic acid or a pharmaceutically acceptable salt thereof; about 17 wt-% to about 33 wt-% microcrystalline cellulose; about 21 wt-% to about 35 wt-% hydroxypropylmethyl cellulose; and about 5 wt-% to about 22 wt-% of a release rate-controlling polymer; wherein wt-% is based on the total weight of the dosage form. In certain embodiments, sustained release oral dosage forms comprise about 5 wt-% to about 12 wt-% (3R)-4-{[(1S)-2-methyl-1-(2-methylpropanoyloxy)propoxy]carbonylamino}-3-(4-chlorophenyl)butanoic acid or a pharmaceutically acceptable salt thereof; about 18 wt-% to about 22 wt-% microcrystalline cellulose; about 33 wt-% hydroxypropylmethyl cellulose; and about 17 wt-% of a release rate-controlling polymer; wherein wt-% is based on the total weight of the dosage form.

In certain embodiments, sustained release dosage forms comprise one or more pharmaceutically acceptable excipients chosen from a diluent, a filler, and a glidant. In certain embodiments, sustained release oral dosage forms provided by the present disclosure comprise about 23 wt-% to about 33 wt-% dibasic calcium phosphate dihydrate; about 0.1 wt-% to about 2 wt-% colloidal silicon dioxide; and about 0.1 wt-% to about 2 wt-% magnesium stearate. In certain embodiments, sustained release oral dosage forms provided by the present disclosure comprise about 19 wt-% to about 22 wt-% dibasic calcium phosphate dihydrate; about 1 wt-% colloidal silicon dioxide; and about 1 wt-% magnesium stearate.

In certain embodiments, sustained release oral dosage forms provided by the present disclosure comprise about 23 wt-% to about 33 wt-% dibasic calcium phosphate anhydrous; about 0.1 wt-% to about 2 wt-% colloidal silicon dioxide; and about 0.1 wt-% to about 2 wt-% magnesium stearate. In certain embodiments, sustained release oral dosage forms provided by the present disclosure comprise about 19 wt-% to about 22 wt-% dibasic calcium phosphate anhydrous; about 1 wt-% colloidal silicon dioxide; and about 1 wt-% magnesium stearate.

In certain embodiments, the microcrystalline cellulose is AVICEL® PH200, the hydroxypropylmethyl cellulose is chosen from METHOCEL™ K4M DC and METHOCEL™ K4M CR, the release rate-controlling polymer is EUDRAGIT® RLPO.

In certain embodiments, sustained release oral dosage forms provided by the present disclosure comprise (3R)-4-{[(1S)-2-methyl-1-(2-methylpropanoyloxy)propoxy]carbonylamino}-3-(4-chlorophenyl)butanoic acid or a pharmaceutically acceptable salt thereof having a Flodex of about 24-26 mm; microcrystalline cellulose having a Flodex of about 12 mm; hydroxypropylmethyl cellulose having a Flodex of about 28-20 mm; and a release rate-controlling polymer having a Flodex of about 22.

In certain embodiments, tablet dosage forms provided by the present disclosure comprise about 5 wt-% to about 12 wt-% (3R)-4-{[(1S)-2-methyl-1-(2-methylpropanoyloxy)propoxy]carbonylamino}-3-(4-chlorophenyl)butanoic acid; about 18 wt-% to about 32 wt-% AVICEL® PH200; about 22 wt-% to about 33 wt-% METHOCEL™ K4M DC; about 5 wt-% to about 18 wt-% EUDRAGIT® RLPO; about 19 wt-% to about 28 wt-% A-TAB®; about 0.7 wt-% to about 1.5 wt-% magnesium stearate; and about 0.9 wt-% to about 1.1 wt-% colloidal silicon dioxide; and the tablet dosage forms each weigh between about 150 mg to about 400 mg; and in certain embodiments from about 50 mg to about 600 mg.

In certain embodiments, dosage forms provided by the present disclosure have a total weight of about 100 mg to about 600 mg.

Characterization of Compounds and Blends

In various aspects, to facilitate tablet manufacturing from dry powder blends, it is desirable that the dry powder formed from the combined compound (1) and pharmaceutically acceptable excipients exhibit acceptable flow properties. Flow of dry powders can be affected by a number of parameters including particle size, particle size distribution, particle shape, particle roughness, bulk density, porosity, air permeability through the powder, electrostatic charges, humidity, settling effects, and cohesion forces such as London dispersion forces and hydrogen bonding forces. We have found that certain combinations or blends of excipients unexpectedly provide improved powder flow properties useful for direct compression tablet manufacturing, which improvements are not anticipated by the powder flow properties of the individual excipients. The unexpected synergistic effect on powder flow provides blends useful in commercial tableting operations. Additionally, we have found that a hydrophilic acrylate polymer can be more effective in slowing and controlling release of compound (1) from a hydrophilic matrix tablet than from a hydrophobic polymer of the same type.

Flow properties of dry powder blends may be characterized by the Flodex. Dry powder blends exhibiting a low Flodex are generally more amenable to the tablet manufacturing process as reflected, for example, in manufacturing speed, tablet weight uniformity, drug content uniformity, hardness uniformity, tablet appearance, and drug release profile. Dry powder blends exhibiting a Flodex of about 22 mm or less, or about 15 mm or less, are useful.

In certain embodiments, compound (1) exhibits a Flodex from about 22 mm to about 28 mm.

In certain embodiments, the microcrystalline cellulose used in a dosage form exhibits a Flodex from about 10 mm to about 14 mm.

In certain embodiments, the hydroxypropylmethylcellulose used in a dosage form exhibits a Flodex from about 26 mm to about 32 mm.

In certain embodiments, the release rate-controlling polymer used in a dosage form exhibits a Flodex from about 20 mm to about 24 mm.

In certain embodiments, the dibasic calcium phosphate dihydrate used in a dosage form exhibits a Flodex of about 4 mm or less.

In certain embodiments, the dibasic calcium phosphate anhydrous used in a dosage form exhibits a Flodex of about 4 mm or less.

Manufacture

In various aspects, sustained release oral dosage forms provided by the present disclosure may be provided as tablets. Formulations provided by the present disclosure are generally useful in forming oral tablet dosage forms by direct compression.

In certain embodiments, dosage forms may be in the form of tablets comprising compound (1). Tablet dosage forms may be of any shape suitable for oral administration of a drug such as spheroidal, cube-shaped, oval, or ellipsoidal. In certain embodiments, tablet dosage forms, e.g., an oral dosage form in the form of a tablet, provided by the present disclosure are matrix systems in which the R-baclofen prodrug (1) is dispersed in a matrix comprising at least one release-rate modifying compound. Matrix systems are well-known in the art as described, for example, in "Handbook of Pharmaceutical Controlled Release Technology," ed. Wise, Marcel Dekker, Inc. (2000) and "Treatise on Controlled Drug Delivery, Fundamentals, Optimization, and Applications," ed. Kydonieus, Marcel Dekker, Inc. (1992).

In certain embodiments, the amount of compound (1) in a dosage form provided by the present disclosure ranges from about 0.1 mg to about 200 mg; in certain embodiments, from about 1 mg to about 100 mg; in certain embodiments from about 5 mg to about 80 mg; and in certain embodiments, from about 5 mg to about 50 mg. For dosage forms comprising a pharmaceutically acceptable salt and/or solvate of compound (1), the amount of compound (1) in a dosage form refers to the mass equivalent weight of compound (1) comprising the salt and/or hydrate. In certain embodiments, tablet dosage forms may comprise a therapeutically effective amount of compound (1). A therapeutically effective amount of compound (1) may comprise: from about 1 mg-equivalents to about 100 mg-equivalents R-baclofen; from about 2 mg-equivalents to about 80 mg-equivalents R-baclofen; from about 2 mg-equivalents to about 40 mg equivalents R-baclofen; or from about 5 mg-equivalents to about 20 mg-equivalents R-baclofen. One (1) mg of compound (1) comprises about 0.535 mg-equivalents R-baclofen. In certain embodiments, the amount of compound (1) in a dosage form provided by the present disclosure is less than an amount that causes moderate sedation and impairment of motor activity in a patient. In certain embodiments, a therapeutically effective amount of compound (1) is less than an amount that causes moderate sedation and impairment of motor activity in a patient.

In certain embodiments in which tablet dosage forms comprise less than a therapeutically effective amount of compound (1), multiple tablet dosage forms may be administered to a patient simultaneously or over a period of time to provide a therapeutically effective dose of compound (1).

In addition to compound (1) and the release rate modifying compounds disclosed herein, tablet dosage forms may also comprise one or more pharmaceutically acceptable excipients such as surfactants, lubricants, plasticizers, binding agents, diluents, anti-adherents, glidants, buffers, dyes, wetting agents, emulsifying agents, pH buffering agents, stabilizing agents, thickening agents, disintegrants, flavoring agents, taste masking agents, and coloring agents.

Diluents, or fillers, may be added to increase the bulk to make dosage forms a practical size for compression. Examples of diluents useful in tablet dosage forms provided by the present disclosure include: dibasic calcium phosphate anhydrous, dibasic calcium phosphate dihydrate, calcium sulfate, dicalcium phosphate, tricalcium phosphate, lactose, cellulose including microcrystalline cellulose, kaolin, mannitol, sodium chloride, dry starch, pregelatinized starch, compressible sugar, and combinations of any of the foregoing. In certain embodiments, a diluent is selected from dibasic calcium phosphate and microcrystalline cellulose. Fillers may be water insoluble, water soluble, or combinations thereof. Examples of useful water insoluble fillers include: silicon dioxide, titanium dioxide, talc, alumina, starch, kaolin, polacrilin potassium, powdered cellulose, microcrystalline cellulose, fumed silica, glyceryl monostearate, magnesium stearate, calcium stearate, colloidal silica, micronized silica, magnesium trisilicate, gypsum, and combinations of any of the foregoing. Examples of useful water-soluble fillers include water soluble sugars and sugar alcohols, such as: lactose, glucose, fructose, sucrose, mannose, dextrose, galactose, the corresponding sugar alcohols and other sugar alcohols, such as mannitol, sorbitol, xylitol, and combinations of any of the foregoing. In certain embodiments wherein the diluent is microcrystalline cellulose, a tablet dosage form may comprise an amount of diluent ranging from about 15 wt-% to about 35 wt-%, and in certain embodiments, from about 18 wt-% to about 20 wt-%. In certain embodiments, the diluent or filler is dibasic calcium phosphate anhydrous, and in certain embodiments dibasic calcium phosphate dihydrate.

Tableting lubricants may be included in dosage forms provided by the present disclosure to reduce sticking effects during processing, film formation, and/or drying. Examples of useful lubricants include: magnesium stearate, calcium stearate, stearic acid, glycerol monostearate, and combinations of any of the foregoing.

Glidants may be included in dosage forms provided by the present disclosure to improve powder flow. Examples of useful glidants include: talc, colloidal silicon dioxide, precipitated silicon dioxide, fumed silicon dioxide, and combinations of any of the foregoing. In certain embodiments, a glidant is colloidal silicon dioxide. Tablet dosage forms may comprise less than about 2 wt-% of a glidant, and in certain embodiments, less than about 1 wt-% of a glidant. In certain embodiments, the glidant is colloidal silicon dioxide.

Binding agents may be included in dosage forms to facilitate adhesion of the constituents. Examples of binding agents useful in tablet dosage forms provided by the present disclosure include polyvinyl acetate phthalate, molasses, methylcellulose, hydroxypropyl cellulose (HPC), hydroxypropyl methyl cellulose (HPMC), sodium carboxymethyl cellulose (MCC), microcrystalline cellulose (MCC), and polyvinyl pyrrolidone. In certain embodiments provided by the present disclosure, a binding agent is microcrystalline cellulose such as AVICEL® PH200 (FMC Corporation).

Plasticizers may be included in tablet dosage forms provided by the present disclosure. Examples of plasticizers useful in tablet dosage forms provided by the present disclosure include: alkyl citrates such as triethyl citrate, acetyl triethyl citrate, tributyl citrate, acetyl triethyl citrate, and acetyl tributyl citrate; sucrose fatty acid esters; glycerin mono-, di- and tri-fatty acid esters such as triacetin, glycerin mono-fatty acid esters, glycerin monostearate and acetylated monoglyceride; polyglycerin fatty acid esters; polyethylene glycols such as macrogol 400, macrogol 600, macrogol 1500, macrogol 4000, macrogol 6000, macrogol 20,000, and macrogol 35,000; dibutyl sebacate; tributyl sebacate; vinyl pyrrolidone; propylene glycol; sesame oil; castor oil; glycerin; silicone resins; D-sorbitol; phytosterol; alkyl phthalates such as diethyl phthalate, dibutyl phthalate and dioctyl phthalate; adipate polyesters; isopropyl myristate; medium chain triglyceride; butyl phthalyl butyl glycolate; polyoxyethylene polyoxypropylene glycol; and combinations of any of the foregoing. Tablet dosage forms may comprise an amount of plasticizer ranging from about 0.1 wt-% to about 10 wt-%, from about 1 wt-% to about 8 wt-%, and in certain embodiments, from about 2 wt-% to about 6 wt-%. In certain embodiments of dosage forms provided by the present disclosure, the dosage form comprises from about 2 wt-% to about 6 wt-% of a plasticizer chosen from triethyl citrate and acetyl triethyl citrate.

Lubricants and anti-adherents may be included in tablet dosage forms provided by the present disclosure to aid in processing. Examples of lubricants and/or anti-adherents useful in tablet dosage forms provided by the present disclosure include: calcium stearate, glyceryl behenate, glyceryl monostearate, magnesium stearate, mineral oil, polyethylene glycol, sodium stearyl fumarate, sodium lauryl sulfate, sodium dodecyl sulfate, stearic acid, talc, hydrogenated vegetable oil, zinc stearate, and combinations of any of the foregoing. In certain embodiments, a lubricant is glyceryl monostearate. In certain embodiments, a lubricant is magnesium stearate. In certain embodiments, tablet dosage forms may comprise an amount of lubricant and/or anti-adherent ranging from about 0.1 wt-% to about 5 wt-%, in certain embodiments from about 0.1 wt-% to about 1 wt-%, and in certain embodiments about 1 wt-%. In certain embodiments, the lubricant is magnesium stearate.

Examples of surfactants useful in tablet dosage forms provided by the present disclosure include: pharmaceutically acceptable anionic surfactants, cationic surfactants, zwitterionic, amphoteric (amphiphatic/amphiphilic) surfactants, non-ionic surfactants, polyethyleneglycol esters or ethers, and combinations of any of the foregoing. Examples of useful pharmaceutically acceptable anionic surfactants include monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates such as sodium lauryl sulfate and sodium dodecyl sulfate, ethoxylated alkyl sulfates, ester linked sulfonates such as docusate sodium and dioctyl sodium succinate, alpha olefin sulfonates, or phosphated ethoxylated alcohols. Examples of useful pharmaceutically acceptable cationic surfactants include: monoalkyl quaternary ammonium salts, dialkyl quaternary ammonium compounds, amidoamines, and animinides. Examples of useful pharmaceutically acceptable amphoteric surfactants include N-substituted alkyl amides, N-alkyl betaines, sulfobetaines, and N-alkyl-6-aminopropionates. Examples of useful pharmaceutically acceptable nonioinic surfactants include diblock and triblock copolymers of polyethylene oxide, polypropylene oxide, polyoxyethylene (20) sorbitan monooleate, and polyethyleneglycol esters or ethers such as polyethoxylated castor oil, polyethoxylated hydrogenated castor oil, and hydrogenated castor oil. In certain embodiments, a surfactant is chosen from sodium lauryl sulfate and sodium dodecyl sulfate. In certain embodiments, tablet dosage forms may comprise less than about 3 wt-% of a surfactant, and in certain embodiments, less than about 2 wt-% of a surfactant.

Disintegrants may be included in a tablet formulation to cause a tablet to break apart, for example, by expansion of a disintegrant when exposed to water. Examples of useful disintegrants include water swellable substances such as low-substituted hydroxypropyl cellulose, cross-linked sodium carboxymethylcellulose (sodium croscarmellose), sodium starch glycolate, sodium carboxymethylcellulose, sodium carboxymethyl starch, ion-exchange resins, microcrystalline cellulose, cross-linked polyvinyl pyrrolidone, starches and pregelatinized starch, formalin-casein, alginic acid, certain complex silicates, and combinations of any of the foregoing.

Tablet dosage forms provided by the present disclosure may further comprise one or more coatings, which may partially or fully cover the tablets. While certain coatings may be applied to modify or affect the release of compound (1) from a tablet dosage form in the gastrointestinal tract, others may have no such effect. For example, one or more additional coatings may be for physical protection, aesthetics, ease in swallowing, identification, and/or to facilitate further processing of the tablets. Coatings may be impermeable to moisture or moisture permeable. Moisture impermeable exterior tablet coatings may be useful for maintaining low moisture content in a dosage form that is packaged in the presence of a desiccant and may thereby enhance, for example, the storage stability of a tablet dosage form. Examples of materials useful in coatings for physical protection include: permeable or soluble materials such as hydroxypropyl methylcellulose, hydroxypropyl cellulose, lactose, hydroxypropyl ethylcellulose, hydroxyethyl cellulose, and xanthan gum. Examples of materials useful in external tablet coatings to facilitate further processing include: talc, colloidal silica, polyvinyl alcohol, titanium dioxide, micronized silica, fumed silica, glycerol monostearate, magnesium trisilicate, and magnesium stearate. An external tablet coating may further include one or more vehicles such as plasticizers, binders, fillers, lubricants, compression aides, and combinations of any of the foregoing. The one or more additional coatings may comprise a single material or a combination of more than one material including any of those disclosed herein. These additional coatings may be applied to tablet dosage forms by methods known to those skilled in the art.

In certain embodiments, dosage forms provided by the present disclosure are substantially free of lactam side products formed by intramolecular cyclization of compound (1) and/or R-baclofen. Dosage forms may be stable to extended storage, such as for example, greater than one year, without substantial lactam formation such as less than about 0.5% lactam by weight, less than about 0.2% lactam by weight, or less than about 0.1% lactam by weight.

Dissolution Profiles of Dosage Forms

The release characteristics of dosage forms provided by the present disclosure comprising compound (1) may be characterized, in part, by the in vitro dissolution profile.

Methods for determining dissolution profiles of dosage forms are well known to those skilled in the pharmaceutical arts. Standard methodologies set forth in the U.S. Pharmacopeia may be used. For example, a dissolution profile may be measured in either a U.S. Pharmacopeia Type I Apparatus (baskets) or a U.S. Pharmacopeia Type II Apparatus (paddles).

Using the latter method, in certain embodiments, dissolution, or release, profiles of dosage forms provided by the present disclosure may be determined by immersing the dosage forms in a 50 mM sodium phosphate monobasic buffer ($NaH_2PO_4$) at pH 6.8, at a temperature of 37° C. The dissolution medium is stirred with a paddle at 75 rpm (USP, Type II). Samples are withdrawn from the dissolution medium at time intervals and the content of compound (1) and or R-baclofen in the dissolution medium is determined using reverse phase high pressure liquid chromatography (HPLC).

In certain embodiments, release of compound (1) from tablet dosage forms provided by the present disclosure exhibits an in vitro dissolution profile in 50 mM sodium phosphate monobasic buffer at pH 6.8 and 37° C. stirred at 75 rpm (USP, Type II) in which: from about 10% to about 30% of compound (1) is released within about 4 hours; from about 20% to about 50% of compound (1) is released within about 8 hours; from about 30% to about 65% of compound (1) is released within about 12 hours; and from about 40% to about 80% of compound (1) is released within about 18 hours.

In certain embodiments, release of (3R)-4-{[(1S)-2-methyl-1-(2-methylpropanoyloxy)propoxy]carbonylamino}-3-(4-chlorophenyl)butanoic acid or pharmaceutically acceptable salt thereof from the oral dosage form exhibits the following in vitro dissolution profile in 50 mM, pH 6.8, sodium phosphate buffer at 37° C. stirred at 75 rpm (USP, Type II): about 10% to about 30% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 4 hours; about 15% to about 35% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 8 hours; about 20% to about 50% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 12 hours; and about 30% to about 80% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 18 hours.

In certain embodiments, release of (3R)-4-{[(1S)-2-methyl-1-(2-methylpropanoyloxy)propoxy]carbonylamino}-3-(4-chlorophenyl)butanoic acid or pharmaceutically acceptable salt thereof from the oral dosage form exhibits the following in vitro dissolution profile in 50 mM, pH 6.8, sodium phosphate buffer at 37° C. stirred at 75 rpm (USP, Type II): about 10% to about 20% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 4 hours; about 20% to about 30% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 8 hours; about 25% to about 45% of the (3R)-4-{[(1S)-2- methyl-1-(2-methylpropanoyloxy)propoxy]carbonylamino}-3-(4-chlorophenyl)butanoic acid or pharmaceutically acceptable salt thereof is released within about 12 hours; and about 35% to about 55% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 18 hours.

In certain of such embodiments, the tablet dosage form exhibiting any of the foregoing release profiles weighs about 200 mg or about 300 mg and is prepared as described in Example 9 or Example 10, respectively.

In certain embodiments, release of (3R)-4-{[(1S)-2-methyl-1-(2-methylpropanoyloxy)propoxy]carbonylamino}-3-(4-chlorophenyl)butanoic acid or pharmaceutically acceptable salt thereof from the oral dosage form exhibits the following in vitro dissolution profile in 50 mM, pH 6.8, sodium phosphate buffer at 37° C. stirred at 75 rpm (USP, Type II): about 15.5% to about 21.5% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 4 hours; about 26% to about 32% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 8 hours; about 35% to about 41% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 12 hours; and about 46% to about 51% of the (3R)-4-{[(1S)-2-methyl-1-(2-methylpropanoyloxy)propoxy]carbonylamino}-3-(4-chlorophenyl)butanoic acid or pharmaceutically acceptable salt thereof is released within about 18 hours.

In certain of such embodiments, the tablet dosage form exhibiting the foregoing release profiles is prepared by any of the methods and contains the compositions described in Examples 16, 18, and/or 19, which describe tablets prepared from structured powder blends.

In certain embodiments, the tablet dosage forms exhibit a release profile that is similar to any of the profiles described in Example 19, Table 14.

Consistent with "Dissolution Testing of Immediate Release Solid Oral Dosage Forms—Guidance for Industry", FDA-CDER, August 1997, dissolution profiles may be considered similar based on a difference factor ($f_1$) and a similarity factor ($f_2$). For dissolution profiles to be considered similar, $f_1$ values should be close to 0 and $f_2$ values should be close to 100. Generally, $f_1$ values up to 15 (0-15) and $f_2$ values greater than 50 (50-100) ensure sameness or equivalence of two dissolution profiles. Procedures for calculating $f_1$ and $f_2$ are set forth in the foregoing reference. In certain embodiments, oral tablet dosage forms provided by the present disclosure exhibit a dissolution profile that when compared with any one of the foregoing dissolution profiles or any of the dissolution profiles described in Table 12 or Table 14 produce an $f_1$ difference factor less than 15 and an $f_2$ similarity factor from 50 to 100.

It is generally accepted that commercially acceptable tablets have a friability of less than about 1 wt-% determined according to USP Test No. 1216. In certain embodiments, tablets provided by the present disclosure have a friability of less than about 1 wt-%, in certain embodiments, less than about 0.5 wt-%, in certain embodiments, less than about 0.3 wt-%, and in certain embodiments, less than about 0.2 wt-%.

Pharmacokinetics and In Vivo Release Profile

Sustained release dosage forms comprising compound (1) exhibit enhanced oral bioavailability as R-baclofen compared to the oral bioavailability of R-baclofen when administered in an equivalent dosage form of R-baclofen and/or racemate. The enhanced oral bioavailability of compound (1) is believed to be due to the efficient absorption of compound (1) throughout the gastrointestinal tract, including the colon, via passive and/or active transport mechanisms. Dosage forms provided by the present disclosure provide for the release of compound (1) from the dosage form during passage of the dosage form through the gastrointestinal tract.

Following oral administration to a patient, sustained release dosage forms comprising compound (1) provide R-baclofen in the systemic circulation of a patient. Compound (1) may be absorbed from the gastrointestinal tract and enter the systemic circulation where the promoiety is cleaved to release R-baclofen. The promoiety of compound (1) may be cleaved either chemically and/or enzymatically. For example, one or more enzymes, such as esterases, present in the stomach, intestinal lumen, intestinal tissue, blood, liver, brain, and/or any other suitable tissue of a mammal can enzymatically cleave the promoiety of compound (1).

When administered orally to a patient, i.e., by a patient swallowing a dosage form provided by the present disclosure, the dosage form provides a sustained therapeutically effective concentration of R-baclofen in the blood of the patient during a continuous period of time. In certain embodiments, dosage forms provide a concentration of R-baclofen in the blood of a patient that is greater than a minimum therapeutically effective concentration and less than a minimum adverse concentration of R-baclofen in the blood of the patient. In certain embodiments, dosage forms provided by the present disclosure provide a therapeutically effective concentration R-baclofen in the blood of a patient for a continuous period of time without exceeding the minimum adverse concentration of R-baclofen. In certain embodiments, the concentration of R-baclofen in the blood of a patient does not exceed a minimum adverse concentration at any time after the dosage form is orally administered to the patient. Dosage forms provided by the present disclosure can provide a therapeutically effective concentration of R-baclofen in the blood of a patient for a continuous period of time while reducing or eliminating adverse drug effects associated with high blood concentrations of R-baclofen, e.g., at concentrations above the minimum adverse concentration, observed following oral dosing of forms comprising R-baclofen. The high bioavailability of R-baclofen achievable using dosage forms comprising compound (1) may facilitate the use of lower mass equivalents of R-baclofen in a dose to achieve a sustained therapeutically effective concentration of R-baclofen in the blood of a patient compared to the amount of R-baclofen in an oral dosage form comprising R-baclofen.

Sustained release dosage forms provided by the present disclosure are capable of providing a sustained therapeutically effective concentration of R-baclofen in the blood of a patient following oral administration. For example, in certain embodiments dosage forms may provide a sustained therapeutically effective concentration of R-baclofen in the blood of a patient during a continuous time period selected from at least about 4 hours, at least about 8 hours, at least about 12 hours, at least about 16 hours, at least about 20 hours, or at least about 24 hours, after oral administration to a patient. In certain embodiments, the concentration of R-baclofen in the blood of a patient will not exceed a minimum adverse concentration at any time after the dosage form is orally administered to the patient, e.g., will not reach a concentration that causes adverse events in the patient. In certain embodiments, a therapeutically effective concentration of R-baclofen in the blood of a patient may range from about 50 ng/mL to about 1,000 ng/mL, and in certain embodiments, from about 100 ng/mL to about 500 ng/mL. The pharmacokinetic profile of the blood R-baclofen concentration can be characterized by a lower $C_{max}/C_{12}$, ratio, and a lower $C_{max}$/dose, compared to immediate release and sustained release oral formulations comprising R-baclofen that provide a similar R-baclofen blood AUC.

In certain embodiments, repeated once daily (QD) dosing of oral tablet dosage forms provided by the present disclosure provide steady state concentrations of R-baclofen in blood as shown in Table 1. In certain embodiments, once daily oral administration of 60 mg compound (1) as a sustained release oral tablet dosage form provided by the present disclosure to sixteen (16) fed healthy adult human volunteers provides a mean steady state pharmacokinetic profile of (R)-3-amino-3-(4-chlorophenyl)butanoic acid in the blood of the healthy adult human volunteers characterized by a $C_{ss,max}$ of about 202±56 ng/mL; a $T_{ss,max}$ of about 3.9±1.0 hours; a $C_{12}$ of about 63 ng/mL; a $C_{ss,max}/C_{ss,12}$ from about 8 to about 15; a $T_{ss,1/2}$ of about 10.9±3.8 hours; and an $AUC_{ss,24}$ of about 1803±320 ng·hr/mL. In certain embodiments, dosage forms provided by the present disclosure provide a $C_{ss,max}/C_{ss,12}$ from about 8 to about 15.

A dosage regimen employing oral administration of dosage forms provided by the present disclosure may be developed to maintain a concentration of R-baclofen in the blood of a patient that is greater than a minimum therapeutically effective concentration and less than a minimum adverse concentration during a prolonged period of time. In certain embodiments, a minimum therapeutically effective concentration of R-baclofen may range from about 1 ng/mL to about 200 ng/mL, and in certain embodiments, can range from about 10 ng/mL to about 100 ng/mL In certain embodiments, a minimum adverse concentration can range from about 200 ng/mL to about 2,000 ng/mL, and in certain embodiments, can range from about 500 ng/mL to about 1,000 ng/mL. A minimum therapeutic concentration and a minimum adverse concentration will depend on a number of factors such as, for example, the disease being treated, the severity of the disease, the intended clinical outcome, the condition of the patient being treated, and so forth. Such regimens may employ repeated dosing of one or more dosage forms provided by the present disclosure. An appropriate interval of dosing may depend, for example, on the amount of compound (1) in the dosage form, the composition of the dosage form, the release characteristics of compound (1) from the dosage form, the disease being treated, the condition of the patient, the potential adverse effects, and the judgment of the prescribing physician. Dosage regimens may include repeated administration of the same dosage form at each interval or different dosage forms at different intervals. For example, a twice-daily dosage regimen can include the administration of a first dosage form in the morning, and a second dosage form in the evening.

Dosage forms provided by the present disclosure further include dosage forms that are bioequivalent to the dosage

TABLE 1

Mean (SD) pharmacokinetic parameters for R-baclofen in blood determined at steady state after once daily (QD) oral dosing of 60 mg (6 × 10 mg) compound (1) as SR3 tablet formulations; or 60 mg (6 × 10 mg), 60 mg (3 × 20 mg), or 60 mg (2 × 30 mg) compound (1) as SR4 tablet formulations for 4 days in fed healthy adult human volunteers.

| Formulation | $C_{ss,max}$ (ng/mL) | $T_{ss,max}$ (hr) | $T_{ss,1/2}$ (h) | $C_{ss,12\,h}$ (ng/mL) | $C_{ss,max}/C_{ss,12\,h}$ | $AUC_{ss,24}$ (ng · h/mL) |
|---|---|---|---|---|---|---|
| 6 × 10 mg Cmpd (1) SR3 Tablets | 149 (47) | 3.2 (1.1) | 12.2 (6.1) | 15 | 9.9 | 1560 (403) |
| 6 × 10 mg Cmpd (1) SR4-10 Tablets | 208 (68) | 3.9 (1.0) | 10.4 (4.3) | 23 | 9.0 | 1850 (417) |
| 3 × 20 mg Cmpd (1) SR4-20 Tablets | 204 (59) | 3.9 (1.0) | 9.8 (3.1) | 19 | 10.7 | 1810 (460) |
| 2 × 30 mg Cmpd (1) SR4-30 Tablets | 193 (41) | 4.0 (1.0) | 12.4 (4.1) | 14 | 13.8 | 1750 (383) |

In certain embodiments, at least one oral dosage form is administered to a human patient at a dose of (3R)-4-{[(1S)-2-methyl-1-(2-methylpropanoyloxy)propoxy]carbonylamino}-3-(4-chlorophenyl)butanoic acid ranging from about 5 mg to about 140 mg, and in certain embodiments from about 10 mg to about 80 mg. In certain of the preceding embodiments, the dose of (3R)-4-{[(1S)-2-methyl-1-(2-methylpropanoyloxy)propoxy]carbonylamino}-3-(4-chlorophenyl)butanoic acid administered is less than a dose of (3R)-4-{[(1S)-2-methyl-1-(2-methylpropanoyloxy)propoxy]carbonylamino}-3-(4-chlorophenyl)butanoic acid that causes moderate sedation and impairment of motor activity in a patient.

forms disclosed herein, in terms of both rate and extent of absorption, for example as defined by the U.S. Food and Drug Administration and discussed in "Guidance for Industry—Bioavailability and Bioequivalence Studies for Orally Administered Drug Products" (2003).

Dosing

It is believed that tablet dosage forms providing sustained systemic concentrations of R-baclofen will enhance patient compliance as compared to the immediate release non-prodrug form which is currently administered three times per day, a regimen that may be inconvenient for patients and difficult for patients to remember. Additionally, it is believed that the use of tablet oral dosage forms provided by the present disclosure will provide enhanced efficacy with reduced side effects such as drowsiness, weakness, headache, seizures, nausea, vomiting, low blood pressure, constipation, confusion, respiratory depression, insomnia, and increased urinary frequency or urinary retention.

The amount of compound (1) that will be effective in the treatment of a particular disease disclosed herein will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of compound (1) administered may depend on, among other factors, the subject being treated, the weight of the subject, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound (1) can be adjusted to provide an equivalent molar quantity or mass equivalent dose of R-baclofen. A dose can comprise multiple dosage forms provided by the present disclosure. In certain embodiments, therapeutically effective doses of R-baclofen are generally from about 0.03 mg to about 1 mg per kilogram body weight per day. In certain embodiments, a daily dose can comprise a mass equivalent of R-baclofen ranging from about 1 mg to about 100 mg; in certain embodiments from about 5 mg to about 80 mg; in certain embodiments from about 5 mg to about 60 mg; and in certain embodiments from about 10 mg to about 40 mg. In certain embodiments, a dose of compound (1) is less than a dose that causes moderate sedation and impairment of motor activity in a patient. The dose of compound (1) and appropriate dosing intervals can be selected to maintain a sustained therapeutically effective concentration of R-baclofen in the blood of a patient, and in certain embodiments, without exceeding a minimum adverse concentration.

In certain embodiments, dosage forms provided by the present disclosure may be administered once per day, twice per day, and in certain embodiments at intervals of more than once per day. Dosing may be provided alone or in combination with other drugs and may continue as long as required for effective treatment of the disease. Dosing includes administering a dosage form to a mammal, such as a human, in a fed or fasted state.

A dose may be administered in a single dosage form or in multiple dosage forms. When multiple dosage forms are used the amount of compound (1) contained within each of the multiple dosage forms may be the same or different.

In certain embodiments, an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a pharmaceutical composition may exhibit a high therapeutic index. The data obtained from these cell culture assays and animal studies may be used in formulating a dosage range that is not toxic for use in humans. A dose of compound (1) may be within a range of circulating concentrations in, for example, the blood, plasma, or central nervous system, that is therapeutically effective, that is less than a sedative dose, and/or that exhibits little or no toxicity.

During treatment, a dose and dosing schedule may provide sufficient or steady state systemic concentration of R-baclofen to treat a disease. In certain embodiments, an escalating dose may be administered.

Therapeutic Uses

Sustained release oral dosage forms provided by the present disclosure may be administered to a patient suffering from any disease or disorder for which the parent drug, R-baclofen, is known, believed to be, or is hereafter determined to be therapeutically effective. Indications for which R-baclofen has been prescribed, and hence for which the dosage forms provided by the present disclosure are also effective, include spasticity, gastro-esophageal reflux disease, narcotic addiction or abuse, alcohol addiction or abuse, nicotine addiction or abuse, emesis, cough, neuropathic pain, musculoskeletal pain, and urinary incontinence.

The suitability of dosage forms provided by the present disclosure in treating the above-listed diseases may be determined by methods described in the art.

A suitable dose of compound (1) to be administered to a patient in need of R-baclofen therapy may be estimated based on the mass equivalent of R-baclofen and the enhanced oral bioavailability of R-baclofen provided by compound (1).

Spasticity

Spasticity is an involuntary, velocity-dependent, increased resistance to stretch. Spasticity is characterized by muscle hypertonia in which there is increased resistance to externally imposed movement with increasing speed of stretch. Spasticity can be caused by lack of oxygen to the brain before, during, or after birth (cerebral palsy); physical trauma (brain or spinal cord injury); blockage of or bleeding from a blood vessel in the brain (stroke); certain metabolic diseases; adrenolekodystrophy; phenylketonuria; neurodegenerative diseases such as Parkinson's disease and amyotrophic lateral sclerosis; and neurological disorders such as multiple sclerosis. Spasticity is associated with damage to the corticospinal tract and is a common complication of neurological disease. Diseases and conditions in which spasticity may be a prominent symptom include cerebral palsy, multiple sclerosis, stroke, head and spinal cord injuries, traumatic brain injury, anoxia, and neurodegenerative diseases. Patients with spasticity complain of stiffness, involuntary spasm, and pain. These painful spasms may be spontaneous or triggered by a minor sensory stimulus, such as touching the patient.

Symptoms of spasticity can include hypertonia (increased muscle tone), clonus (a series of rapid muscle contractions), exaggerated deep tendon reflexes, muscle spasms, scissoring (involuntary crossing of the legs), deformities with fixed joints, stiffness, and/or fatigue caused by trying to force the limbs to move normally. Other complications include urinary tract infections, chronic constipation, fever or other systemic illnesses, and/or pressure sores. The degree of spasticity can vary from mild muscle stiffness to severe, painful, and uncontrollable muscle spasms. Spasticity may coexist with other conditions but is distinguished from rigidity (involuntary bidirectional non-velocity-dependent resistance to movement), clonus (self-sustaining oscillating movements secondary to hypertonicity), dystonia (involuntary sustained contractions resulting in twisting abnormal postures), athetoid movement (involuntary irregular confluent writhing movements), chorea (involuntary, abrupt, rapid, irregular, and unsustained movements), ballisms (involuntary flinging movements of the limbs or body), and tremor (involuntary rhythmic repetitive oscillations, not self-sustaining). Spasticity can lead to orthopedic deformity such as hip dislocation, contractures, or scoliosis; impairment of daily living activities such as dressing, bathing, and toileting; impairment of mobility such as inability to walk, roll, or sit; skin breakdown secondary to positioning difficulties and shearing pressure; pain or abnormal sensory feedback; poor weight gain secondary to high caloric expenditure; sleep disturbance; and/or depression secondary to lack of functional independence.

Treatment of spasticity includes physical and occupational therapy such as functional based therapies, rehabilitation, facilitation such as neuro-developmental therapy, proprioceptive neuromuscular facilitation, and sensory integration; biofeedback: electrical stimulation; and orthoses. Oral medications useful in treating spasticity include baclofen, benzodiazepines such as diazepam, dantrolene sodium; imidazolines such as clonidine and tizanidine; and gabapentin. Intrathecal medications useful in treating spasticity include baclofen. Chemodenervation with local anesthetics such as lidocaine and xylocaine; type A botulinum toxin and type B botulinum toxin; phenol and alcohol injection can also be useful in treating spasticity. Surgical treatments useful in treating spasticity include neurosurgery such as selective dorsal rhizotomy; and orthopedic operations such as contracture release, tendon or muscle lengthening, tendon transfer, osteotomy, and arthrodesis.

A principal pharmacological effect of baclofen in mammals is reduction of muscle tone and consequently the drug is frequently used in the treatment of spasticity.

The efficacy of the dosage forms provided by the present disclosure for the treatment of spasticity can be assessed using animal models of spasticity and in clinically relevant studies of spasticity of different etiologies. Animal models of spasticity are known and include (a) the mutant spastic mouse; (b) the acute/chronic spinally transected rat and the acute decerebrate rat; (c) primary observation Irwin Test in the rat; and d) Rotarod Test in the rat and mouse. Other animal models include spasticity induced in rats following transient spinal cord ischemia, spasticity in mouse models of multiple sclerosis; and spasticity in rat models of cerebral palsy. The maximal electroshock seizure (MES) threshold test in rodents is sensitive for detecting potential anticonvulsant properties.

The efficacy of dosage forms provided by the present disclosure for treating spasticity may also be assessed in humans using double blind placebo-controlled clinical trials. Clinical trial outcome measures for spasticity include the Ashworth Scale, the modified Ashworth Scale, muscle stretch reflexes, presence of clonus and reflex response to noxious stimuli. Spasticity can be assessed using methods and procedures known in the art such as a combination of clinical examination, rating scales such as the Ashworth Scale, the modified Ashworth scale the spasm frequency scale and the reflex score, biomechanical studies such as the pendulum test, electrophysiologic studies including electromyography, and functional measurements such as the Fugl-Meyer Assessment of Sensorimotor Impairment scale. Other measures can be used to assess spasticity associated with a specific disorder such as the Multiple Sclerosis Spasticity Scale.

Gastroesphageal Reflux Disease

Gastro-esophageal reflux disease (GERD) is defined as chronic symptoms or mucosal damage produced by the abnormal relfux in the esophagus. Symptoms of GERD include heartburn, esophagitis, strictures, dysphagia, chronic chest pain, cough, hoarsness, voice changes, chronic ear ache, burning chest pains, nausea, and sinusitis.

Tonic contraction of the lower esophageal sphincter is the principal factor preventing the reflux of gastric contents into the esophagus. Transient lower esophageal sphincter relaxation (TLESR) is the major mechanism underlying reflux in normal subjects and patients with GERD. $GABA_B$ agonists such as R-baclofen have been shown to reduce TLESRs in humans (Lidums et al., *Gastroenterology* 2000, 118(1), 7-13; Vela et al., *Aliment Pharmacol Ther* 2003, 17(2), 243-51; Ciccaglione and Marzio, *Gut* 2003, 52(4), 464-70; and Zhang et al., *Gut* 2002, 50(1), 19-24). Reduction of the frequency of TLESRs by baclofen is believed to be due to inhibition of vagal afferents, information transfer between the nucleus tractus solitarious and dorsal motor nucleus of the vagus, and vagal efferent outflow (Hornby et al., *Gastroenterol Clin N Am* 2002, 31(4 Suppl), S11-S20). More specifically, (3R)-4-{[(1S)-2-methyl-1-(2-methylpropanoyloxy)propoxy]carbonylamino}-3-(4-chlorophenyl)butanoic acid, compound (1), has been shown to reduce reflux episodes in clinical trials (Gerson et al., *Am J Gastroenterol* 2009, online publication 29 Dec. 2009; doi: 10.1038/ajg.2009.718).

The efficacy for treating GERD may be assessed using animal models and in clinical trials.

Emesis

Nausea, vomiting, and retching are basic human protective reflexes against the absorption of toxins as well as responses to certain stimuli. Nausea is a subjectively unpleasant wavelike sensation in the back of the throat or epigastrium associated with pallor or flushing, tachycardia, and an awareness of the urge to vomit. Sweating, excess salivation, and a sensation of being cold or hot may also occur. Vomiting is characterized by contraction of the abdominal muscles, descent of the diaphragm, and opening of the gastric cardia, resulting in forceful expulsion of stomach contents from the mouth. Retching involves spasmodic contractions of the diaphragm and the muscles of the thorax and abdominal wall without expulsion of gastric contents. Emesis is used herein to refer to nausea, vomiting, and/or retching.

Baclofen has been shown to suppress the retching and vomiting induced by morphine, thereby indicating the involvement of the $GABA_B$ receptor in the emetic control pathway (Suzuki et al., *Neuropharmacology* 2005, 49(8), 1121-31). Baclofen has also been shown to antagonize emesis induced by nicotine and motion in animal models (Chan et al., *Eur J Pharmacology* 2007, 559(2-3), 196-201).

Efficacy in treating emesis can be assessed using appropriate animal models and using clinical trials. For example, efficacy in treating emesis induced by chemotherapeutic agents can be determined based on effects indicative of emesis such as pica, gastric stasis, and reduced food intake in rats, mice, or ferrets. In clinical trials, assessment instruments such as the Duke Descriptive Scale, Visual Analog Scales, Morrow Assessment of Nausea and Emesis, Rhodes Index of Nausea and Vomiting Form-2, and Functional Living Index Emesis can be used to measure efficacy. In general, adequately controlled, double blind placebo controlled trails may be used to evaluate efficacy in humans.

Cough

Cough reflex, elicited by activation of cough receptors located in the respiratory tract, clears inhaled irritants and foreign substances from the respiratory tract and, in conjunction with the mucociliary system, can expel excessive airway secretion produced under abnormal conditions from the respiratory tract. Cough can be caused by mild acuate upper respiratory tract infections, allergies, asthma, chronic obstructive pulmonary disease, lung cancer, gastroesophageal reflux disease, post-nasal drip, and heart or ear disorders. However, chronic non-productive cough having no identifiable cause accounts for a significant percent of patients presenting with cough. Chronic cough is associated with exacerbation of asthmatic symptoms, rib fractures, breathlessness, ruptured abdominal muscles, pneumothorax, syncope, second and third degree heart block, and loss of consciousness. Persistent and uncontrollable cough can lead to morbidity and severely impairs the quality of life of these patients.

Cough includes acute and chronic cough of any type, etiology, or pathogenesis, and in particular cough associated with laryngeal sensory neuropathy.

The anti-tussive effects of baclofen are well-known (Dicpinigaitis and Dobkin, *Chest* 1997, 111(4), 996-9; Dicpinigaitis and Rauf, *Respiration* 1998, 65(1), 86-8; Dicpinigaitis et al., *J Clin Pharmacol* 1998, 38(4), 364-7; and Kreutner et al., U.S. Pat. No. 5,006,560 and WO 91/08740).

Efficacy in treating cough can be assessed using appropriate animal models and using clinical trials.

Substance Addiction or Abuse

In clinical trials, baclofen has been shown to be effective in treating cocaine addiction (Brebner et al., *Alcohol* 2002, 37(5), 478-84; and Haney et al., *Neuropsychopharmacology* 2006, 31, 1814-21); methamphetamine dependence (Heinzerling et al., *Drug Alcohol Depend* 2006, 85(3), 177-84); opioid dependence (Assadi et al., *BMC Psychiatry* 2003, Nov. 18, 3(16); and Ahmadi-Abhari et al., *J Clin Pharm Therapeutics* 2001, 26(1), 67-71); alcohol craving and intake (Addolorato et al., *Alcohol* 2002, 37(5), 504-8; and Flannery et al., *Alcohol Clin Exp Res* 2004, 28(10), 1517-23); nicotine use (Markou et al., *Ann N.Y. Acad Sci* 2004, 1025, 491-503); and drug addiction generally (Cousins et al., *Drug Alcohol Dependence* 2002, 65(3), 209-20).

Efficacy for treating substance addiction and abuse can be assessed using animal models and in clinical trials. Animal models of substance abuse disorders are known.

Neuropathic Pain

Neuropathic pain involves an abnormal processing of sensory input usually occurring after direct injury or damage to nerve tissue. Neuropathic pain is a collection of disorders characterized by different etiologies including infection, inflammation, disease such as diabetes and multiple sclerosis, trauma or compression to major peripheral nerves, and chemical or irradiation-induced nerve damage. Neuropathic pain typically persists long after tissue injury has resolved.

Compound (1) may be used to treat neuropathic pain. In certain embodiments, compound (1) may be used to treat neuropathic pain including, for example, post-herpetic neuralgia, peripheral neuropathy, trigeminal neuralgia, painful diabetic neuropathy, HIV-related neuropathic pain, cancer-related pain, or fibromyalgia.

The International Association for the Study of Neuropathic Pain defines neuropathic pain states as disorders that are characterized by lesions or dysfunction of the neural system(s) that under normal conditions transmit noxious information to the central nervous system. The mechanisms underlying neuropathic pain conditions are highly heterogeneous, however, all types of neuropathic pain are presumed to involve nerve injury and certain common aberrations in somatosensory processing in the central and/or peripheral nervous system. Potential causes of neuropathic pain include physical damage, infection, and chemical exposure. Neuropathic pain can be generally classified as a focal/multifocal lesion of the peripheral nervous system, e.g., post-herpetic neuralgia, a generalized lesion of the peripheral nervous system, e.g., painful diabetic neuropathy, HIV-related NP, a lesion of the central nervous system, or a more complex neuropathic disorder. Peripheral neuropathic pain can arise as a consequence of trauma and surgery related nerve injury, e.g., brachial plexus injury; entrapment neuropathies such as lumbar disc compression, carpal tunnel syndrome; disease-related neuropathies, e.g., diabetes and HIV-AIDS; radiculopathy; complex regional pain syndrome; and/or tumor growth leading to nerve compression or infiltration. Central neuropathic pain can be the result of stroke, multiple sclerosis, post-ischemic myelopathy; post-herpetic neuralgia; and/or post-traumatic spinal cord injury.

Neuropathic pain can be characterized as a partial or complete loss of afferent sensory function and the paradoxical presence of certain hyperphenomena in the painful area. The nerve tissue lesion may be found in the brain, spinal cord, or the peripheral nervous system. Symptoms vary depending on the condition and can manifest as hyperalgesia (the lowering of pain threshold and an increased response to noxious stimuli), allodynia (the evocation of pain by non-noxious stimuli such as cold, warmth, or touch), hyperpathia (an explosive pain response that is suddenly evoked from cutaneous areas with increased sensory detection threshold when the stimulus intensity exceeds sensory threshold), paroxysms (a type of evoked pain characterized by shooting, electric, shock-like or stabbing pain that occur spontaneously, or following stimulation by an innocuous tactile stimulus or by a blunt pressure), paraesthesia (abnormal but non-painful sensations, which can be spontaneous or evoked, often described as pins and needles), dysesthesia (abnormal unpleasant but not necessarily painful sensations, which can be spontaneous or provoked by external stimuli), referred pain and abnormal pain radiation (abnormal spread of pain), and wind-up like pain and aftersensations (the persistence of pain long after termination of a painful stimulus).

Patients with neuropathic pain typically describe burning, lancinating, stabbing, cramping, aching, and/or sometimes vice-like pain. The pain can be paroxysmal or constant. Pathological changes to the peripheral nerve(s), spinal cord, and brain have been implicated in the induction and maintenance of chronic neuropathic pain. Patients suffering from neuropathic pain typically endure chronic, debilitating episodes that are refractory to current pharmacotherapies and profoundly affect their quality of life. Currently available treatments for neuropathic pain, which include tricyclic antidepressants and gabapentin, typically show limited efficacy in the majority of patients.

There are several types of neuropathic pain. A classification that relates to the type of damage or related pathophysiology causing a painful neuropathy includes: neuropathies associated with mechanical nerve injury such as carpal tunnel syndrome, vertebral disk herniation, entrapment neuropathies, ulnar neuropathy, and neurogenetic thoracic outlet syndrome; metabolic disease associated neuropathies such as diabetic polyneuropathy; neuropathies associated with neurotropic viral disease such as herpes zoster and human immunodeficiency virus (HIV) disease; neuropathies associated with neurotoxicity such as chemotherapy of cancer or tuberculosis, radiation therapy, drug-induced neuropathy, and alcoholic neuropathy; neuropathies associated with inflammatory and/or immunologic mechanisms such as multiple sclerosis, anti-sulfatide antibody neuropathies, neuropathy associated with monoclonal gammopathy, Sjogren's disease, lupus, vasculitic neuropathy, polyclonal inflammatory neuropathies, Guillain-Bane syndrome, chronic inflammatory demyelinating neuropathy, multifocal motor neuropathy, paraneoplastic autonomic neuropathy, ganglinoic acetylcholine receptor antibody autonomic neuropathy, Lambert-Eaton myasthenic syndrome and myasthenia gravis; neuropathies associated with nervous system focal ischemia such as thalamic syndrome (anesthesia dolorosa); neuropathies associated with multiple neurotransmitter system dysfunction such as complex regional pain syndrome (CRPS); neuropathies associated with chronic/neuropathic pain such as osteoarthritis, low back pain, fibromyalgia, cancer bone pain, chronic stump pain, phantom limb pain, and paraneoplastic neuropathies; toxic neuropathies (e.g., exposure to chemicals such as exposure to acrylamide, 3-chlorophene, carbamates, carbon disulfide, ethylene oxide, n-hexane, methyl n-butylketone, methyl bromide, organophosphates, polychlorinated biphenyls, pyriminil, trichlorethylene, or dichloroacetylene), focal traumatic neuropathies, phantom and stump pain, monoradiculopathy, and trigeminal neuralgia; central neuropathies including ischemic cerebrovascular injury (stroke), multiple sclerosis, spinal cord injury, Parkinson's disease, amyotrophic lateral sclerosis, syringomyelia, neoplasms, arachnoiditis, and post-operative pain; mixed neuropathies such as diabetic neuropathies (including symmetric polyneuropathies such as sensory or sensorimotor polyneuropathy, selective small-fiber polyneuropathy, and autonomic neuropathy; and focal and multifocal neuropathies such as cranial neuropathy, limb mononeuropathy, trunk mononeuropathy, mononeuropathy multiplex, and asymmetric lower limb motor neuropathy) and sympathetically maintained pain. Other neuropathies include focal neuropathy; glossopharyngeal neuralgia; ischemic pain; trigeminal neuralgia; atypical facial pain associated with Fabry's disease, Celiac disease, hereditary sensory neuropathy, or $B_{12}$-deficiency; mono-neuropathies; polyneuropathies; hereditary peripheral neuropathies such as Carcot-Marie-Tooth disease, Refsum's disease, Strumpell-Lorrain disease, and retinitis pigmentosa; acute polyradiculoneuropathy; and chronic polyradiculoneuropathy. Paraneoplastic neuropathies include paraneoplastic subacute sensory neuropathy, paraneoplastic motor neuron disease, paraneoplastic neuromyotonia, paraneoplastic demyelinating neuropathies, paraneoplastic vasculitic neuropathy, and paraneoplastic autonomic insufficiency. Prodrugs of $GABA_B$ agonists provided by the present disclosure can be used to treat any of the foregoing types of neuropathic pain. In certain embodiments, the neuropathic pain is chosen from post-herpetic neuralgia, peripheral neuropathy, trigeminal neuralgia, painful diabetic neuropathy, HIV-related neuropathic pain, cancer-related pain, and fibromyalgia. In certain embodiments, the neuropathic pain is chosen from post-herpetic neuralgia and trigeminal neuralgia.

In clinical studies, intrathecal baclofen administration has been shown to be effective in treating neuropathic pain associated with spinal-cord injury and multiple sclerosis (Herman et al., *Clin J Pain* 1992, 8(4), 338-345; and Taira et al., *Stereotactic Funct Neurosurg* 1995, 65, 101-105), painful extremity paresthesias (Gatscher et al., *Acta Neurochir Suppl* 2002, 79, 75-76), and sympathetically maintained pain (Van Hilten et al., *N Engl J Med* 2000, 343, 625-630; Becker et al., *J Clin Neurosci* 2000, 7, 316-319; and Zuniga et al., *Reg Anesth Pain Med* 2002, 27, 90-93). Baclofen has also been shown to be effective in trigeminal, glossopharyngeal, vagoglossopharyngeal, and ophthalmic-postherpetic neuralgias (Bowsher, *Br Med Bull* 1991, 47, 644-66; Fromm et al., *Neurology* 1981, 31, 683-687; and Ringel and Roy, *Ann Neurol* 1987, 21, 514-515); and in patients with diabetic neuropathy (Anghinah et al., *Muscle Nerve* 1994, 958-59). Doses of baclofen from about 50 mg/day to about 60 mg/day have been shown to be effective in treating trigeminal neuralgia (Fromm et al., *Ann Neurol* 1984, 15, 240-244).

The efficacy of compound (1) for treating various types of neuropathic pain can also be assessed in clinical trials using techniques known in the art including, for example, randomized double-blind placebo controlled methods. End points used in clinical trials for neuropathic pain can be determined using validated neuropathic pain criteria such as the Brief Pain Inventory, Categorical Scale, Gracety Pain Scale, Likert Scale, Neuropathic Pain Scale, Numerical Pain Scale, Short Form McGill Pain Questionnaire, Verbal Pain Scale, Visual Analog Scale (VAS), VAS Pain Intensity Scale, and/or VAS Pain Relief Scale.

Musculoskeletal Pain

Musculoskeletal conditions causing tenderness and muscle spasms include fibromyalgia, tension headaches, myofascial pain syndrome, facet joint pain, internal disk disruption, somatic dysfunction, spinal fractures, vertebral osteomyelitis, polymyalgia rheumatica, atlantoaxial instability, atlanto-occipital joint pain, osteoporotic vertebral compression fracture, Scheuermann's disease, spondyloysis, spondylolisthesis, kissing spines, sacroiliac joint pain, sacral stress fracture, coccygodynia, failed back syndrome, and mechanical low back or neck pain (Meleger and Krivickas, *Neurol Clin* 2007, 25, 419-438). In these conditions, muscle spasm is related to local factors involving the affected muscle groups without the increased tone or reflex characteristic of spasticity. Muscle, tendon, ligament, intervertebral disc, articular cartilage, and bone can be involved in musculoskeletal pain. Disorders that can produce neck and back pain include muscle strain, ligament sprain, myofascial pain, fibromyalgia, facet joint pain, internal disc disruption, somatic dysfunction, spinal fracture, verterbral osteomyelitis, and polymyalgia rheumatica, atlantoaxial instability and atlanto-occipital joint pain.

Baclofen is known to induce muscle-relaxant effects when administered systemically or centrally (Malcangio and Bowery, *Trends Pharmacol Sci* 1996, 17, 457-462). Consequently, the use of baclofen for treating spasticity associated with upper motor neuron syndromes is well established. Studies have also shown that baclofen can be effective in treating muscular pain and/or spasms associated with peripheral musculoskeletal conditions. For example, baclofen has been shown effective in treating migraine (Hering-Hanit, *Cephalalgia* 1999, 19, 589-591; and Hering-Hanit and Gadoth, *Headache* 2000, 40, 48-51); and specifically in tension-type headaches (Freitag, *CNS Drugs* 2003, 17(6), 373-381); as well as in low-back pain and radiculopathy (Zuniga et al., *Anesthesiology* 2000, 92, 876-880; Vatine et al., *Pain Clin* 1989, 2, 207-217; Dapas et al., *Spine* 1985, 10(4), 345-349; Raphael et al., *BMC Musculoskeletal Disorders* 2002, Jun. 20, 3(17); and Magora et al., *Pain Clin* 1988, 2, 81-85).

The efficacy of prodrugs of compound (1) for treating one or more types of musculoskeletal pain can be assessed in animal models of neuropathic pain and in clinical trials.

Back Pain

Compound (1) may be used to treat back pain including back pain in the cervical, thoracic, and/or lumbar spinal regions. The back pain may be acute or chronic. Acute low back pain is defined as low back pain present for fewer than 4 weeks, sometimes grouped with sub-acute low back pain with symptoms present for fewer than 3 months. Chronic low back pain is defined as low back pain present for more than 3 months.

Low Back Pain

Low back pain generally occurs in the lumbar region of the back in the location of lumbar vertebrae L1-L5. Pain in the lower back can be caused by: a sprain, strain, or spasm to one of the muscles, ligaments, facet joints, and/or sacroiliac joints in the back; spinal sprain or over-compression; or disc rupture or bulge. Low back pain may also reflect nerve or muscle irritation or bone lesions. Most low back pain follows injury or trauma to the back, but pain may also be caused by degenerative conditions such as arthritis or disc disease, osteoporosis, or other bone diseases, viral infections, irritation to joints and discs, or congenital abnormalities in the spine. Obesity, smoking, weight gain during pregnancy, stress, poor physical condition, posture inappropriate for the activity being performed, and poor sleeping position also may contribute to low back pain. Additionally, scar tissue created when the injured back heals itself does not have the strength or flexibility of normal tissue. Buildup of scar tissue from repeated injuries eventually weakens the back and can lead to more serious injury. Occasionally, low back pain may indicate a more serious medical problem. Pain accompanied by fever or loss of bowel or bladder control, pain when coughing, and progressive weakness in the legs may indicate a pinched nerve or other serious condition. People with diabetes may have severe back pain or pain radiating down the leg related to neuropathy. Low back pain can be caused by bulging disc (e.g., protruding, herniated, or ruptured disc), sciatica, spinal degeneration, spinal stenosis, osteoporosis, osteoarthritis, compression fractures, skeletal irregularities, fibromyalgia, spondylolysis and/or spondylolisthesis. Less common spinal conditions that can cause low back pain include ankylosing spondylitis, bacterial infections, osteomyelitis, spinal tumors, Paget's disease, and Scheuermann's disease. Clinical results suggest that $GABA_B$ agonists such as baclofen can be effective in treating low back pain (Dapas et al., *Spine* 1985, 10(4), 345-349; and Raphael et al., *BMC Musculoskeletal Disorders* 2002, Jun. 20, 3(17)). For example doses of baclofen from about 20 mg/day to about 80/mg day have been shown to be effective in treating acute low back pain (Dapas et al., *Spine* 1985, 10(4), 345-9).

In certain embodiments, methods of treating low back pain provided by the present disclosure comprises treating disorders, conditions, and/or symptoms associated with low back pain such as muscle spasms. Symptoms of low back pain can depend on the cause. For example, symptoms of back sprain or back strain include muscle spasms, cramping, stiffness, and pain centered in the back and buttocks. Symptoms of nerve-root pressure include leg pain, also referred to as sciatica, and nerve-related manifestations such as tingling, numbness, or weakness in one leg or in the foot, lower leg, or both legs. Symptoms of arthritis of the spine include pain and stiffness that are worse in the back and hip.

Muscle Spasm Associated with Acute Painful Musculoskeletal Conditions

Muscle spasms are associated with many acute painful musculoskeletal conditions. Low back pain and neck pain are common manifestations of such conditions. Acute musculoskeletal spasm of the back is a common disorder that causes localized pain, stiffness, reduced mobility, impaired activities of daily living, and sleep disturbances. Most episodes of acute low back pain or neck pain are nonspecific. Most subjects do not meet the criteria set forth for low back and neck pain, including significant trauma, cancer, infection, or motor weakness. Nonspecific back pain is defined as mechanical back pain, facet joint pain, osteoarthritis, muscle sprains, and muscle spasms. Low back pain may be caused by reflex spasms in the paraspinal muscles. Acute back spasms are involuntary and often painful contractions of the muscles of the back including the cervical, thoracic, and/or lumbar spinal regions. Spasms associated with the lumbar vertebrae are also referred to as lower back spasms.

Typical pharmacologic treatments for acute neck and low back pain are NSAIDS, acetaminophen, and muscle relaxants. A recent placebo-controlled study concluded that baclofen was effective, safe, and well-tolerated in treating acute low-back syndrome with evidence of paravertebral muscle spasm and functional disability of less than 2 weeks duration (Dapas et al., *Spine* 1985, 10(4), 345-349). Accordingly compound (1) may be used to treat muscle spasm associated with acute painful musculoskeletal conditions, including acute back spasms, and more particularly acute lower back spasms.

Fibromyalgia

Fibromyalgia is a condition characterized by aching and pain in muscles, tendons and joints all over the body, but especially along the spine. The body also is tender to touch in specific areas referred to as tender or trigger points. Other symptoms of fibromyalgia include sleep disturbance, depression, daytime tiredness, headaches, alternating diarrhea and constipation, numbness and tingling in the hands and feet, feelings of weakness, memory difficulties, and dizziness. Although the etiology of fibromyalgia is not known, stress, disordered sleep patterns, abnormal production of pain-related chemicals in the nervous system, and/or low levels of growth hormone are believed to contribute to the onset of fibromyalgia.

Current treatment of fibromyalgia is based on symptoms, with the goal of alleviating pain, restoring sleep, and improving general quality of life. Several nonpharmacologic treatments include exercise, education, behavioral and physical therapy. Pharmacologic treatments include tricyclic compounds, serotonin reuptake inhibitors, analgesics, muscle relaxants, and ACE inhibitors. There is evidence suggesting that baclofen may be useful in improving fibromyalgia symptoms (Taylor-Gjevre and Gjevre, *Lupis* 2005, 14(6), 486-8).

The efficacy of administering compounds provided by the present disclosure for treating fibromyalgia may be assessed using animal and human models of fibromyalgia and in clinical trials. Animal models of neuropathic pain or clinically relevant studies of different types of neuropathic pain have been found useful in assessing therapeutic activity for treating fibromyalgia.

The use of compound (1) and other R-baclofen prodrugs for treating neuropathic pain, musculoskeletal pain, low back pain, muscle spasm associated with acute painful musculoskeletal conditions, and fibromyalgia, is disclosed in Benson et al., US 2009/0118365, the entire contents of which are incorporated herein by this reference.

Urinary Incontinence

Urinary incontinence is any involuntary leakage of urine and can be categorized into five types based on the pattern of symptoms including urge incontinence, stress incontinence, overflow incontinence, functional incontinence, and mixed incontinence (Abrams et al., *Neurology and Urodynamics* 2002, 21, 167-178).

Urge incontinence is an abrupt and intense urge to urinate that cannot be suppressed, followed by an uncontrollable loss of urine. Urge incontinence can be caused by a combination of overactivity of the muscles in the bladder along with poor squeezing ability of the bladder muscles in part due to changes in the part of the brain in the frontal lobe that inhibits urination. Involuntary actions of bladder muscles can occur because of damage to the nerves of the bladder, to the nervous system including the spinal cord and brain, or to the muscles themselves. Damage to the muscles and nerves may occur as the result of stroke, surgery, or brain disorders such as multiple sclerosis, Parkinson's disease, Alzheimer's disease.

Stress incontinence is the uncontrollable loss of small amounts of urine when coughing, straining, sneezing, lifting heavy objects, or performing any maneuver that suddenly increases pressure within the abdomen and is generally caused by insufficient strength of the pelvic floor muscles. Incontinence following prostate surgery is the most common form of stress incontinence in men. In women, stress incontinence can result from physical changes associated with pregnancy, childbirth, menopause, or pelvic surgery.

Overflow incontinence is the uncontrollable leakage of small amounts of urine, usually caused by some type of blockage or by weak contractions of the bladder muscles. Overflow incontinence can be caused by prostate surgery, enlarged prostate, constipation, nerve damage, drugs that affect the brain or spinal cord that interfere with nerve messages, diabetes, multiple sclerosis, tumors, spinal cord injuries, nervous system disorders, and diseases such as multiple sclerosis that can decrease neural signals from the bladder or the expulsion of urine by the detrusor muscle.

Functional incontinence refers to urine loss resulting from the physical inability or unwillingness to get to the toilet due to limited mobility. Causes of functional incontinence include confusion, dementia, poor eyesight, poor mobility, poor dexterity, unwillingness to toilet due to depression, anxiety, anger, drunkenness, or physical impossibility such as a person in a wheelchair. Conditions causing immobility include stroke, severe arthritis, and contentions that interfere with mental function such as dementia due to Alzheimer's disease and severe depression.

Mixed urinary incontinence involves more than one type of incontinence.

Urinary incontinence also includes bedwetting or enuresis.

Urinary incontinence also includes overactive bladder. Overactive bladder is urgency, with or without urge incontinence, usually with frequency and nocturia (Abrams, *Urology* 2003, 62 (Suppl 5B), 28-37; Ouslander *N Engl J Med* 2004, 350, 786-99; and Wein and Rovner, *Urology* 2002 (Suppl 5A), 7-12). Urgency is the complaint of a sudden compelling desire to void; frequency is the complaint by the patient who considers that he/she voids too often by day; and nocturia is the complaint that the individual has to wake more than about one time during the night to void. Patients with overactive bladder typically present with symptoms of a sudden and compelling need to urinate that is difficult to defer (urgency), involuntary leakage of urine with feeling so urgency (urge urinary incontinence), frequency ($\geq 8$ micturitions in 24 hours) and nocturia ($\geq$one awakening per night to void). The symptoms of overactive bladder are due to involuntary contractions of the detrusor muscle during the filling phase of the micturition cycle. These involuntary contractions are termed detrusor overactivity and are mediated by acetylcholine-induced stimulation of bladder muscarinic receptor (Andersson, *Urology* 1997, 50(Suppl. 6A), 74-84). Detrusor overactivity is the urodynamic observation characterized by involuntary detrusor contractions during the filling phase that may be spontaneous or provoked. Detrusor overactivity can be characterized as idiopathic detrusor overactivity where there is no defined underlying cause and detrusor overactivity wherein there is a relevant neurologic condition.

Interstitial cystitis, also termed painful bladder syndrome, is a disorder related to urinary incontinence. Interstitial cystitis is a chronic inflammatory condition of the bladder believed to be caused by many factors including autoimmune, allergic, and infectious etiologies. Symptoms of interstitial cystitis include excessive urgency to urinate even after the patient has voided, urinary frequency averaging 16 times per day or greater, night time urination, suprapubic (bladder/pelvic/perineal) pain, and/or dyspareunia. In certain embodiments, dosage forms provided by the present disclosure may be used to treat interstitial cystitis.

In a double blind crossover trial baclofen administered at a dose of 5 mg four times per day was shown to significantly improve diurnal and nocturnal of frequency of micturition and the severity of incontinence in patients with unstable bladder syndrome (Taylor and Bates, *British J Urology* 1979, 51, 504-505). Accordingly compound (1) is expected to be useful in treating urinary incontinence including overactive bladder and/or detrusor overactivity.

Dosing

It is believed that tablet dosage forms providing sustained systemic concentrations of R-baclofen will enhance patient compliance as compared to the immediate release non-prodrug form which is currently administered three times per day, a regimen that is inconvenient for patients and difficult for patients to remember. Additionally, it is believed that the use of tablet oral dosage forms provided by the present disclosure will provide enhanced efficacy with reduced side effects which side effects may include drowsiness, weakness, headache, seizures, nausea, vomiting, low blood pressure, constipation, confusion, respiratory depression, insomnia, and increased urinary frequency or urinary retention.

The amount of compound (1) that will be effective in the treatment of a particular disease disclosed herein will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of compound (1) administered may depend on, among other factors, the subject being treated, the weight of the subject, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound (1) can be adjusted to provide an equivalent molar quantity or mass equivalent dose of R-baclofen. A dose can comprise multiple dosage forms provided by the present disclosure. Therapeutically effective doses of R-baclofen are generally from about 0.03 mg to about 1 mg per kilogram body weight per day. In certain embodiments, a daily dose can comprise a mass equivalent of R-baclofen ranging from about 1 mg to about 100 mg, in certain embodiments, from about 5 mg to about 80 mg, in certain embodiments, from about 5 mg to about 60 mg, and in certain embodiments, from about 10 mg to about 40 mg. In certain embodiments, a dose of compound (1) is less than a dose that causes moderate sedation and impairment of motor activity in a patient. The dose of compound (1) and appropriate dosing intervals can be selected to maintain a sustained therapeutically effective concentration of R-baclofen in the blood of a patient, and in certain embodiments, without exceeding a minimum adverse concentration.

In certain embodiments, dosage forms provided by the present disclosure may be administered once per day, twice per day, and in certain embodiments at intervals of more than once per day. Dosing may be provided alone or in combination with other drugs and may continue as long as required for effective treatment of the disease. Dosing includes administering a dosage form to a mammal, such as a human, in a fed or fasted state.

A dose may be administered in a single dosage form or in multiple dosage forms. When multiple dosage forms are used, the amount of compound (1) contained within each of the multiple dosage forms may be the same or different.

In certain embodiments, an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a pharmaceutical composition may exhibit a high therapeutic index. The data obtained from these cell culture assays and animal studies may be used in formulating a dosage range that is not toxic for use in humans. A dose of compound (1) may be within a range of circulating concentrations in, for example, the blood, plasma, or central nervous system, that is therapeutically effective, that is less than a sedative dose, and that exhibits little or no toxicity.

During treatment, a dose and dosing schedule may provide sufficient or steady state systemic concentration of R-baclofen to treat a disease. In certain embodiments, an escalating dose may be administered.

Combination Therapy

Dosage forms provided by the present disclosure may further comprise one or more pharmaceutically active compounds in addition to compound (1). Such compounds may be provided to treat the same disease or a different disease than the disease being treated with compound (1).

In certain embodiments, compound (1) may be used in combination with at least one other therapeutic agent. In certain embodiments, compound (1) may be administered to a patient together with another compound for treating movement disorders such as spasticity, digestive disorders such as gastro-esophageal reflux disease and emesis, or addictive or abuse disorders such as nicotine addiction or abuse, alcohol addiction or abuse, narcotic addiction or abuse, cough, neuropathic pain, musculoskeletal pain, or urinary incontinence. In certain embodiments, the at least one other therapeutic agent may be a different R-baclofen prodrug. In various aspects, compound (1) and the at least one other therapeutic agent may act additively or, and in certain embodiments, synergistically. The at least one additional therapeutic agent may be included in the same dosage form comprising compound (1) or may be in a separate dosage form. Accordingly, methods provided by the present disclosure can further include, in addition to administering compound (1), administering one or more therapeutic agents effective for treating the same or different disease than the disease being treated by compound (1). Methods provided by the present disclosure include administration of compound (1) and one or more other therapeutic agents provided that the combined administration does not inhibit the therapeutic efficacy of compound (1) and/or does not produce adverse combination effects.

In certain embodiments, dosage forms comprising compound (1) may be administered concurrently with the administration of another therapeutic agent, which may be part of the same dosage form as, or in a different dosage form than, that comprising compound (1). Compound (1) may be administered prior or subsequent to administration of another therapeutic agent. In certain embodiments of combination therapy, the combination therapy may comprise alternating between administering compound (1) and a composition comprising another therapeutic agent, e.g., to minimize adverse drug effects associated with a particular drug. When compound (1) is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising compound (1) may be administered with one or more substances to enhance, modulate and/or control release, bioavailability, therapeutic efficacy, therapeutic potency, stability, and the like of compound (1). For example, to enhance the therapeutic efficacy of compound (1) or its metabolite, R-baclofen, compound (1) may be co-administered with, or a dosage form comprising compound (1) may comprise, one or more active agents to increase the absorption or diffusion of compound (1) or R-baclofen from the gastrointestinal tract to the systemic circulation, or to inhibit degradation of compound (1) or R-baclofen in the blood of a patient. In certain embodiments, a dosage form comprising compound (1) may be co-administered with an active agent having pharmacological affects that enhance the therapeutic efficacy of compound (1).

Additionally, dosage forms provided by the present disclosure may be used in combination with other drugs that are themselves known to cause spasticity, gastro-esophageal reflux disease, narcotic addiction or abuse, alcohol addiction or abuse, nicotine addiction or abuse, emesis, cough, neuropathic pain, and/or musculoskeletal pain as an adverse effect, thereby preventing or reducing the occurrence of such adverse effects.

In certain embodiments, dosage forms provided by the present disclosure may be administered to a patient for treating a movement disorder such as spasticity in combination with a therapy or another therapeutic agent known or believed to be effective in treating a movement disorder such as spasticity. Examples of drugs for treating movement disorders such as spasticity and which may be administered in conjunction with compound (1) include: levodopa, mild sedatives such as benzodiazepines including alprazolam, chlordiazepoxide, clonazepam, clorazepate, diazepam, lorazepam, and oxazepam; muscle relaxants such as baclofen, anticholinergic drugs such as trihexyphenidyl, atropine, scopolamine, and diphenhydramine; antipsychotics such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; and antidepressants such as amitriptyline.

In certain embodiments, dosage forms provided by the present disclosure may be administered to a patient for treating a gastrointestinal disorder such as gastro-esophageal reflux disease in combination with a therapy or another therapeutic agent known or believed to be effective in treating a gastrointestinal disorder such as gastro-esophageal reflux disease. Examples of drugs for treating gastrointestinal disorders such as gastro-esophageal reflux disease and which may be administered in conjunction with compound (1) include: $H_2$ inhibitors such as cimetidine, famotidine, nizatidine, and ranitidine; proton pump inhibitors such as omeprazole, lansoprazole, pantoprazole, rabeprazole, and exomeprazole; and prokinetics such as cisparide, bethanechol, and metoclopramide.

In certain embodiments, dosage forms provided by the present disclosure may be administered to a patient for treating emesis in combination with a therapy or another therapeutic agent known or believed to be effective in treating emesis. Examples of drugs for treating emesis (nausea and vomiting) and which may be administered in conjunction with compound (1) include benzamines such as metoclopramide; phenothiazines such as prochlorperazine, perphenazine, chlorpromazine, promethazine, and thiethylperazine; butyrophenones such as droperidol and haloperidol; dopamine 2 antagonists such as metoclorpamide; $5-HT_3$ antagonists such as ondansetron, granisetron, dolasetron, palonosetron; NK-1 receptor antagonists such as aprepitant, corticosteroids such as dexamethazone; antihistamines such as diphenhydramine and hydroxyzine; cannabinoids such as dronabinol; and benzodiazepines such as lorazepam, midazolam, alprazolam, and olanzapine.

In certain embodiments, dosage forms provided by the present disclosure may be administered to a patient for treating alcohol addiction or abuse in combination with a therapy or another therapeutic agent known or believed to be effective in treating alcohol addiction or abuse. Examples of drugs for treating alcohol addiction or abuse and which may be administered in conjunction with compound (1) include disulfuram, naltrexone, clonidine, methadone, 1-alpha-acetylmethadol, buprenorphine, and bupropion.

In certain embodiments, dosage forms provided by the present disclosure may be administered to a patient for treating narcotic addiction or abuse in combination with a therapy or another therapeutic agent known or believed to be effective in treating narcotic addiction or abuse. Examples of drugs for treating narcotic addiction or abuse and which may be administered in conjunction with compound (1) include buprenorphine, tramadol, methadone, and naltrexone.

In certain embodiments, dosage forms provided by the present disclosure may be administered to a patient for treating nicotine addiction or abuse in combination with a therapy or another therapeutic agent known or believed to be effective in treating nicotine addiction or abuse. Examples of drugs for treating nicotine addiction or abuse and which may be administered in conjunction with compound (1) include bupropion, clonidine, and nicotine.

In certain embodiments, dosage forms provided by the present disclosure may be administered to a patient for treating cough in combination with a therapy or another therapeutic agent known or believed to be effective in treating cough. Examples of drugs for treating cough and which may be administered in conjunction with compound (1) include dextromethorphan, guaifenesin, hydrocodone, benzonatate, diphenhydramine, pseudoephedrine, acetaminophen, and carbinoxamine.

In certain embodiments, dosage forms provided by the present disclosure may be administered to a patient for treating neuropathic pain in combination with a therapy or another therapeutic agent known or believed to be effective in treating neuropathic pain. Examples of drugs useful for treating pain include: opioid analgesics such as morphine, codeine, fentanyl, meperidine, methadone, propoxyphene, levorphanol, hydromorphone, oxycodone, oxymorphone, tramadol and pentazocine; nonopioid analgesics such as aspirin, ibuprofen, ketoprofen, naproxen, and acetaminophen; non-steroidal anti-inflammatory drugs such as aspirin, choline magnesium trisalicylate, diflunisal, salsalate, celecoxib, rofecoxib, valdecoxib, diclofenac, etodolac, fenoprofen, flubiprofen, ibuprofen, indomethacin, ketoprofen, ketorolac, meclofanamate, mefenamic acid, meloxicam, nabumetone, oxaprozin, piroxicam, sulindac, and tometin; antiepileptics such as gabapentin, pregabalin, carbamazepine, phenyloin, lamotrigine, and topiramate; antidepressants such as duloxetine, amitriptyline, venlafaxine, nortryptyline, imipramine, and desipramine; local anesthetics such as lidocaine, and mexiletine; NMDA receptor antagonists such as dextropethorphan, memantine, and ketamine; N-type calcium-channel blockers such as ziconotide; vanilloid receptor-1 modulators such as capsaicin; cannabinoid receptor modulators such as sativex; neurokinin receptor antagonists such as lanepitant; other analgesics such as neurotropin; and other drugs such as desipramine, clonazepam, divalproex, oxcarbazepine, divalproex, butorphanol, valdecoxib, vicoprofen, pentazocine, propoxyhene, fenoprofen, piroxicam, indometnacin, hydroxyzine, buprenorphine, benzocaine, clonidine, flurbiprofen, meperidine, lacosamide, desvenlafaxine, and bicifadine.

In certain embodiments, a drug useful for treating neuropathic pain is chosen from propoxyphene, meperidine, hydromorphone, hydrocodone, morphine, codeine, 2-piperidinol-1-alkanol, eliprodil, ifenprodil, rofecoxib, celecoxib, salicylic acid, diclofenac, piroxicam indomethacin, ibuprofen, naproxen, gabapentin, carbemazepine, pregabalin, topiramate, valproic acid, sumatriptan, elitriptan, rizatriptan, zolmitriptan, naratriptan, flexeril, carisoprodol, robaxisal, norgesic, dantrium, diazepam, chlordiazepoxide, alprazolam, lorazepam, acetaminophen, nitrous oxide, halothane, lidocaine, etidocaine, ropivacaine, chloroprocaine, sarapin, bupivacaine, capsicin, desipramine, amitriptyline, doxepin, perphenazine, protriptyline, tranylcypromine, baclofen, clonidine, mexelitine, diphenhydramine, hydroxyzine, caffeine, prednisone, methyl-prednisone, decadron, sertraline, paroxetine, fluoxetine, tramadol, levodopa, dextromethorphan, substance P antagonists, and botulinum toxin.

In certain embodiments, a drug useful for treating neuropathic pain can be chosen from a nicotine receptor partial agonist and an analgesic agent.

Non-pharmacological therapies for treating neuropathic pain include transcutaneous electrical nerve stimulation, percutaneous electrical nerve stimulation, and acupuncture.

In certain embodiments, dosage forms provided by the present disclosure may be administered to a patient for treating fibromyalgia in combination with a therapy or another therapeutic agent known or believed to be effective in treating fibromyalgia, or in certain embodiments, a disease, disorder, or condition associated with fibromyalgia. Drug therapy for fibromyalgia may be tailored to the severity and frequency of fibromyalgia episodes. For occasional episodes, acute treatment may be indicated. For fibromyalgia episodes occurring two or more times per month, or when attacks greatly impact the patient's daily life, chronic therapy on an ongoing basis may be appropriate.

Treatments for fibromyalgia that reduce the frequency of episodes and include non-steroidal anti-inflammatory agents (NSAIDs), adrenergic beta-blockers, calcium channel blockers, tricyclic antidepressants, selective serotonin reuptake inhibitors, anticonvulsants, NMDA receptor antagonists, dopamine agonists, selective 5-$HT_3$ receptor antagonists, opioids, muscle relaxants, sedative hypnotics, and other therapy. Examples of NSAIDs useful for treating fibromyalgia include aspirin, ibuprofen, fenoprofen, flurbiprofen, ketoprofen, mefenamic acid, and naproxen. Examples of adrenergic beta-blockers useful for treating fibromyalgia include acebutolol, atenolol, imilol, metoprolol, nadolol, pindolol, propranolol, and timolol. Examples of calcium channel blockers useful for treating fibromyalgia include amlodipine, diltiazem, dotarizine, felodipine, flunarizine, nicardipine, nifedipine, nimodipine, nisoldipine, and verapamil. Examples of tricyclic antidepressants useful for treating fibromyalgia include amitriptyline, desipramine, doxepin, imipramine, nortriptyline, cyclobenzaprine, and protriptyline. Examples of selective serotonin reuptake inhibitors useful for treating fibromyalgia include fluoxetine, methysergide, nefazodone, paroxetine, sertraline, and citalopram. Examples of other antidepressants useful for treating fibromyalgia include bupropion, nefazodone, norepinephrine, venlafaxine, duloxetine, and trazodone. Examples of anticonvulsants (antiepileptics) useful for treating fibromyalgia include divalproex sodium, felbamate, gabapentin, lamotrigine, levetiracetam, oxcarbazepine, tiagabine, topiramate, valproate, and zonisamide. Examples of NMDA receptor antagonists useful for treating fibromyalgia include dextromethorphan, magnesium, and ketamine. Examples of dopamine agonists useful for treating fibromyalgia include α-dihydroergocryptine. Examples of opioids useful for preventing fibromyalgia are tramadol, oxycodone, and methadone. An example of a muscle relaxant useful for treating fibromyalgia is cyclobenzaprine. Examples of therapies useful for treating fibromyalgia include exercise, interferon, growth hormone, hormone therapy, diet low in animal fat and high in fiber, and complementary therapies such as counseling/psychotherapy, relaxation training, progressive muscle relaxation, guided imagery, diaphragmatic breathing, biofeedback, acupuncture, and physical and massage therapy.

Acute fibromyalgia treatments intended to eliminate or reduce the severity of muscular/skeletal pain and any associated symptoms include serotonin receptor agonists, such as triptans (5-hydroxytryptophan (5-HT) agonists), for example, almotriptan, eletriptan, frovatriptan, naratriptan, rizatriptan, sumatriptan, and zolmitriptan; ergotamine-based compounds such as dihydroergotamine and ergotamine; antiemetics such as metoclopramide and prochlorperazine; and compounds that provide analgesic effects.

Other examples of drugs useful in treating fibromyalgia include acetaminophen, aspirin, caffeine, cyproheptadine, methysergide, valproic acid, NSAIDs such as diclofenac, flurbiprofen, ketaprofen, ketorolac, ibuprofen, indomethacin, meclofenamate, and naproxen sodium; opioids such as codeine, meperidine, and oxycodone; and glucocorticoids such as dexamethasone, prednisone, and methylprednisolone.

In certain embodiments, dosage forms provided by the present disclosure may be administered to a patient for treating musculoskeletal pain in combination with a therapy or another therapeutic agent known or believed to be effective in treating musculoskeletal pain. Examples of drugs useful for treating musculoskeletal pain include cyclobenzaprine, dantrolene, methocarbamol, orphenadrine, tizanidrine, metaxalone, carisoprodol, chlorphenesin, chlorzoxazone, alprazolam, bromazepam, chlordiazepoxide, clorazepate, diazepam, flunitriazepam, lorazepam, medazepam, midazolam, oxazepam, prazepam, triazolam, temazepam, and botulinum toxin. In certain embodiments, any of the drugs useful for treating neuropathic pain may be co-administered with compound (1) for treating musculoskeletal pain.

In certain embodiments, dosage forms provided by the present disclosure may be administered to a patient for treating low back pain in combination with a therapy or another therapeutic agent known or believed to be effective in treating low back pain. Examples of drugs useful for treating low back pain include NSAIDs such as aspirin, naproxen, and ibuprofen; anticonvulsants, antidepressants such as amitriptyline and desipramine; and opioids such as codeine, oxycodone, hydrocodone, and morphine. In certain embodiments, any of the drugs useful for treating neuropathic pain may be co-administered with a prodrug of a $GABA_B$ agonist for treating low back pain. Therapies for low back pain include the use of cold and hot compresses, bed rest, exercise, spinal manipulation, acupuncture, biofeedback, interventional therapy, traction, transcutaneous electrical nerve stimulation, ultrasound, vertebroplasty, kyphoplasty, discectomy, foraminotomy, intradiscal electrothermal therapy, nucleoplasty, radiofrequency lesioning, spinal fusion, and spinal laminectomy.

In certain embodiments, dosage forms provided by the present disclosure may be administered to a patient for treating low back pain in combination with a therapy or other therapeutic agent for treating muscle spasms, for example muscle spasms associated with low back pain, such as muscle relaxants. Examples of drugs useful as muscle relaxants for treating muscle spasms include baclofen, carisoprodol, chlorzoxazone, cyclobenzaprine, diazepam, metaxalone, methocarbamol, orphenadrine, and tizanidine.

In certain embodiments, dosage forms provided by the present disclosure may be administered to a patient for treating urinary incontinence in combination with a therapy or another therapeutic agent known or believed to be effective in treating urinary incontinence. Examples of drugs useful for treating urinary incontinence include amitriptyline, belladonna, darifenacin, desmopressin, duloxetine, estrogen, fesoterodine, flavoxate, hyoscyamine, imidafenacin, imipramine, nitrofurantoin, oxybutynin, propiverine, solaberon, solifenacin, tamsulosin hydrochloride, tamsulosin, tolterodine, trospium, type A botulinum toxin, and vardenafil hydrochloride. Other drugs that show potential for treating urinary incontinence and in particular overactive bladder include drugs acting on $K^+$ channels such as NS-8, KW-7158, ZD-0947; 5-$HT_3$ antagonists; 5-$HT_{1a}$ antagonists such as REC-0545; P2X antagonists; NK1 receptor antagonists such as SSR-240600, TA-5538, and aprepitant; $β_3$-agonists such as GW-427353 and KUC-7483, YM-178; and other such as DDP-200 (oxybutynin and gabapentin), nitroflurbiprofen, elocalcitol, NCX-2111, and besipirdine (Colli et al., *Expert Opin Investig Drugs* 2007, 16(7), 999-1007). $β_3$-Adrenoceptor agonists have also recently been proposed for the treatment of overactive bladder (Tyagi et al., *Drugs of the Future* 2009, 34(8), 635-640). Other drugs useful for treating urinary incontinence are disclosed in Robinson and Cardozo, *Maturitas* 2010 doi:10.1016/j.maturitas.2009.12.022.

EXAMPLES

The following examples describe in detail oral tablet dosage forms comprising compound (1). It will be apparent to those skilled in the art that many modifications, both to materials and methods, may be practiced without departing from the scope of the disclosure.

Example 1

Preparation and Characterization of Compound (1) Dry Powders

Compound (1) Lot 70 was crystallized using the following procedure. To a 5 L three-necked round bottom flask equipped with a mechanical stirrer, Teflon-coated thermocouple, reflux condenser, and nitrogen inlet was added compound (1) (72 g), acetone (186 mL) and hexane (672 mL) The mixture was stirred (60% speed) and heated to 50° C. for 1 hour. All material had dissolved. Additional hexane (1081 mL) was added over 1 hour, maintaining the temperature at 50° C. The solution was cooled to 45° C. and maintained at 45° C. for 5 hours, at which time solids had formed. The solution was further cooled to 40° C. for 12 hours, then 35° C. for 12 hours. The solution was then cooled to 22-25° C. for 2 hours. Product was collected by filtration (fast) through a sintered glass funnel, and rinsed with a solution of acetone (100 mL) and hexane (900 mL). The wet filter cake was transferred to a vacuum oven and dried at 40° C. for 12 hours to afford crystalline compound (1) (Lot 70, 70 g, 97%) as a white solid.

Compound (1) Lot 71 was crystallized using the following procedure. To a 5 L three-necked round bottom flask equipped with a mechanical stirrer, Teflon-coated thermocouple, reflux condenser, and nitrogen inlet was added compound (1) (72 g), acetone (186 mL) and hexane (672 mL) The mixture was stirred (60% speed) and heated to 50° C. for 1 hour. All material had dissolved. Additional hexane (1081 mL) was added over 2 minutes, and the temperature decreased to 39° C. with formation of solids. The solution was cooled to 22-25° C. over 1 hour, and then cooled to 0-5° C. for 1 hour. Product was collected by filtration (slow) through a sintered glass funnel, and rinsed with a solution of acetone (100 mL) and hexane (900 mL). The wet filter cake was transferred to a vacuum oven and dried at 40° C. for 12 hours to afford crystalline compound (1) (Lot 71, 70 g, 97%) as a white solid.

Crystalline compound (1) Lot 4 was prepared using the same concentrations and solvents, but with a linear cooling ramp from 50° C. to 0° C. for 2.5 hours.

Various properties of crystalline compound (1) prepared by slow crystallization (Lot 70), fast crystallization (Lot 71), and an intermediate rate of crystallization (Lot 4) are shown in Table 2.

TABLE 2

Characterization of compound (1) crystal morphology.

| | Particle size (μm) | | | | | | |
|---|---|---|---|---|---|---|---|
| | Wet method | | Dry method | | Flowdex | Observed filtration | SEM | Relative crystallization |
| Batch | dv0.5 | dv0.9 | dv0.5 | dv0.9 | (mm) | rate | Morphology | rate |
| Lot 4 | 3.35 | 40.47 | 11.09 | 102 | 23 | slow | ~25-50 microns rounded aggregates of primary crystals <5 microns | intermediate crystallization |
| Lot 70 | 4.81 | 37.2 | 27.53 | 106.87 | 26 | fast | ~100 micron filaments | slow crystallization |
| Lot 71 | 22.17 | 63.02 | 17.64 | 107.48 | 26 | slow | ~25-50 microns jagged aggregates of primary crystals <5 microns | fast crystallization |

The particle size and shape of compound (1) samples were characterized by scanning electron microscopy (SEM) analysis. Samples from each of the three lots were mounted on double-sided carbon tape, sputter-coated with a thin layer of platinum, and then examined using a Hitachi-4700 SEM. SEM micrographs of the three lots at 500× magnification are shown in FIG. 1. Corresponding images of the three lots at 10,000× magnification are shown in FIG. 2.

Lot 4 (FIGS. 1A and 2A) comprises rounded aggregates about 25-50 microns in diameter. By contrast, Lot 70 (FIGS. 1B and 2B) comprises filaments about 100 microns in length. Lot 71 (FIGS. 1C and 2C) comprises yet another morphology characterized by irregularly shaped aggregates about 25-50 microns in length/width.

Example 2

Flow Characterization of Dry Powders

The flow of dry powders was characterized using a FLODEX™ Powder Flowability Index Test Instrument (Hanson Research Corporation, Chatsworth, Calif.). The instrument was equipped with a cylindrical metal reservoir, which holds the test powder prior to flow testing. The cylindrical reservoir has an inside diameter of 5.7 cm and a length of 7.4 mm. The bottom end of the reservoir can be closed with removable metal discs. Each disc has a round orifice centered in the disc. Orifice diameters range from 4 mm to 10 mm in 1 mm increments, and from 10 mm to 34 mm in 2 mm increments. Prior to flow testing, the orifice is blocked. Powder is then placed over the blocked orifice. When the orifice is unblocked, powder can flow through the orifice under the force of gravity if the orifice diameter is sufficiently large. Powder that flows through small orifices is considered to have flow properties useful for tableting. For example, a Flodex measurement (Flodex) of less than about 24 mm is typically used for high-speed tableting operations at commercial scale. A Flodex less than about 20 mm is useful for high-speed tableting operations. A Flodex of 18 mm or less is considered especially useful for high speed tableting operations.

The Flodex is determined by first gently filling the reservoir with approximately 70 cc of test powder while the orifice at the bottom is blocked, while avoiding severe piling, and without vibrating or tapping the powder bed. Next, the orifice is unblocked. This can be accomplished by opening a shutter that is supplied with the instrument. Alternatively, if a shutter is not used, the powder-filled reservoir fitted with a disc can be set on a dry, flat surface to block the orifice. Then, slowly and evenly, the reservoir is lifted to allow the powders to flow. In either procedure, if the powder flows through the orifice, a clear channel is left within the powder bed. If the powder does not flow through the orifice, an arch-shaped cavity within the powder bed is formed above the orifice and is referred to as an arch. The flow test is conducted with various orifice sizes until the minimum orifice size for good flow is identified, which is referred to as the Flodex. The Flodex is the minimum orifice diameter at which the powder flows through the orifice more times than it does not in at least three measurement trials.

Example 3

Flow Properties of Compound (1) and Excipients

The Flodex for three lots of neat compound (1) and a variety of neat tableting excipients are shown in Table 3. The three lots of neat compound (1) are chemically equivalent but each lot differs by particle size and shape (see Example 1, FIG. 1 and FIG. 2). As shown in Table 3, Lot 4 exhibits the lowest Flodex. The low Flodex is attributed to the rounded particle shape, which flows more smoothly than fibrous particle masses characteristic of Lot 70 that can tangle or the irregularly shaped particles characteristic of Lot 71 that can impart high interparticle frictional forces when in motion. These measurements demonstrate that the Flodex is sufficiently discriminating to detect and quantify differences in the flow properties of powders comprising particles with different morphologies.

TABLE 3

Flow properties of compound (1) and excipients.

| Test Powder | Arches/Total Trials Orifice Size (mm) | | | | | | | | | | | | | | Flodex (mm) |
|---|---|---|---|---|---|---|---|---|---|---|---|---|---|---|---|
| | 4 | 6 | 8 | 9 | 10 | 12 | 16 | 18 | 20 | 22 | 24 | 26 | 28 | 30 | |
| Compound (1), Lot 4 | | | | | | | | | | 3/3 | 3/3 | 0/3 | | | 24 |
| Compound (1), Lot 70 | | | | | | | | | | 3/3 | 3/3 | 4/6 | 2/6 | | 26 |
| Compound (1), Lot 71 | | | | | | | | | | 3/3 | 3/3 | 3/3 | 1/3 | 0/3 | 26 |
| AVICEL® PH200 | | | 3/3 | 4/7 | 6/9 | 0/3 | | | | | | | | | 12 |
| METHOCEL™ K4M (SP) | | | | | | | 3/3 | 3/3 | 3/3 | 3/3 | 6/9 | 2/9 | | | 28 |
| METHOCEL™ K4M (DC) | | | | | | | | 3/3 | | 3/3 | 3/3 | 3/3 | 2/3 | 7/9 2/9 | 30 |
| EUDRAGIT® RLPO | | | | | | | | | | 3/3 | 3/3 | 3/9 | | | 22 |
| DI-TAB® (unmilled) | 0/3 | 0/3 | | | | 0/3 | | | | | 0/3 | | | | ≤4 |

AVICEL® PH200 listed in Table 3 is microcrystalline cellulose with an average particle size of 190 microns (FMC Biopolymer Corporation, Philadelphia, Pa.). METHOCEL™ K4M SP is hydroxypropyl methylcellulose (METHOCEL™ K4M Standard Premium, Dow Chemical Company, Midland, Mich.). This substituted cellulosic polymer has a hydroxypropoxyl content of approximately 8 wt-%, a methoxyl content of approximately 22 wt-%, a nominal viscosity in water at 2% concentration of approximately 4,000 centipoise, and a particle size such that at least 75 wt-% is less than 149 microns. METHOCEL™ K4M (DC) (Dow Wolff Cellulosics, Midland, Mich.) is chemically identical to METHOCEL™ K4M SP but has a larger particle size of about 250 microns. EUDRAGIT® RLPO (Evonik Industries AG, Darmstadt, Del.) is a copolymer comprising poly(ethyl acrylate, methyl methacrylate, trimethylammonioethyl methacrylate chloride) 1:2:0.2 (USP/NF assay 8.85-11.96% ammonio methacrylate units on a dry substance basis). This acrylate polymer has an average molecular weight of approximately 150,000 grams per mole, and a particle size such that at least 90 weight percent is less than 315 microns. EUDRAGIT® RSPO (Evonik Industries AG, Darmstadt, Del.) is a copolymer of ethyl acrylate, methyl methacrylate and a low content of a methacrylic acid ester with quaternary ammonium groups (USP/NF assay 4.48-6.77% ammonio methacrylate units on a dry substance basis). DI-TAB® is dibasic calcium phosphate, dihydrate (Innophos, Inc., Cranbury, N.J.) having a nominal particle size of 180 microns.

As shown in Table 3 the Flodex of the excipients used in tablet formulations can exhibit significantly different flow properties. The rank order from low to high Flodex is DI-TAB®, AVICEL® PH200, EUDRAGIT® RLPO, METHOCEL™ K4M SP, and METHOCEL™ K4M DC.

Example 4

Flow of Dry Powder Blends

Two dry blends of tableting excipients were prepared and the flow properties determined. Blend A08-011 was prepared by sequentially passing 42.0 g of AVICEL® PH200, 43.4 g of METHOCEL™ K4M (SP), and 25.7 g of EUDRAGIT® RLPO, through a sieve with 20 wires per inch into a container. Thirty-six (36.0) g of DI-TAB® and 1.5 g of colloidal silicon dioxide (CAB-O-SIL™ M-5P, Cabot Corporation, Billerica, Mass.) were pre-mixed and then passed through the same screen into the container. The colloidal silicon dioxide was included in the blend as a flow-promoting agent.

The sized powders were tumble-mixed in a V-blender for 5 minutes. Finally, 1.5 g of magnesium stearate (Univar), previously passed through a sieve with 40 wires per inch, was added to the powder mixture and the entire composition V-blended for 5 minutes. Magnesium stearate served as a tableting lubricant to reduce friction and to promote the smooth ejection of tablets during tablet compression. The flow of the resulting blend (A08-011) exhibited a Flodex of 20 mm.

Blend A08-016 was prepared using a procedure similar to that used to prepare Blend A08-011. Blend A08-016 was equivalent in composition to Blend A08-011 except that the METHOCEL™ K4M SP was replaced with METHOCEL™ K4M DC. Flow of the resulting Blend A08-016 was then measured.

The compositions of the two blends and the respective Flodex are provided in Table 4. Although neat METHOCEL™ K4M SP exhibited a high Flodex of 28 mm and the flow of neat METHOCEL™ K4M DC exhibited an even higher Flodex of 30 mm (Table 3), the blend of the combined excipients exhibited values of 20, and 15 mm, respectively. This result would not be predicted based on the Flodex of the individual components listed in Table 4.

TABLE 4

Flow properties of dry blends of excipients.

| Excipient | Blend A08-011 Composition | | Blend A08-016 Composition | |
|---|---|---|---|---|
|  | wt (g) | wt % | wt (g) | wt % |
| AVICEL ® PH200 | 42.0 | 28.0 | 42.0 | 28.0 |
| METHOCEL ™ K4M SP | 43.4 | 28.9 | — | — |
| METHOCEL ™ K4M DC | — | — | 43.4 | 28.9 |
| EUDRAGIT ® RLPO | 25.7 | 17.1 | 25.7 | 17.1 |
| DI-TAB ® (unmilled) | 36.0 | 24.0 | 36.0 | 24.0 |
| Colloidal Silicon Dioxide | 1.5 | 1.0 | 1.5 | 1.0 |
| Magnesium Stearate | 1.5 | 1.0 | 1.5 | 1.0 |
| Total | 150.0 | 100.0 | 150.0 | 100.0 |
| Flodex Index (mm) | 20 | | 15 | |

Example 5

Flow of Dry Powder Blends Containing Compound (1)

Two dry powder blends formulated with excipients and a single lot of compound (1) were prepared and the flow properties determined. Thirty (30.0) g of compound (1), 69.0 g of AVICEL® PH200, 86.7 g METHOCEL™ K4M SP, and 51.3 g EUDRAGIT® RLPO were sequentially passed through a 20-mesh sieve into a bowl. Fifty-seven (57.0) g of DI-TAB® and 3.0 grams of silicon dioxide were pre-mixed and passed through the same 20-mesh sieve into the bowl. The resulting sized powders were tumble-blended in a 2 quart V-blender for 5 minutes. Finally, 3.0 g of magnesium stearate, previously sized through a 40-mesh sieve, was added to the mixed powder and tumble-mixed for 5 minutes. The Flodex of the resulting blend A08-020 was 22 mm.

A second blend A08-017 was prepared using a procedure similar to that used to prepare blend A08-020. The composition of blend A08-017 was equivalent to that of A08-020 except that METHOCEL™ K4M DC replaced METHOCEL™ K4M SP. The compositions and flow properties of the two blends are summarized in Table 5. The flow of the blend containing compound (1) formulated with METHOCEL™ K4M DC was significantly better with a Flodex of 16 mm compared to the same blend formulated with METHOCEL™ K4M SP at 22 mm This result would not be predicted based only on the results of the flow of the individual components listed in Table 3, which shows that METHOCEL™ K4M SP and METHOCEL™ K4M DC have similar flow properties of 28 mm and 30 mm, respectively.

TABLE 5

Flow properties of dry powder blends containing compound (1).

| Blend Component | Blend A08-020 Composition | | Blend A08-017 Composition | |
|---|---|---|---|---|
|  | wt (g) | wt % | wt (g) | wt % |
| Compound (1), Lot 4 | 30.0 | 10.0 | 20.0 | 10.0 |
| AVICEL ® PH200 | 69.0 | 23.0 | 46.0 | 23.0 |
| METHOCEL ™ K4M SP | 86.7 | 28.9 | — | — |
| METHOCEL ™ K4M DC | — | — | 57.8 | 28.9 |
| EUDRAGIT ® RLPO | 51.3 | 17.1 | 34.2 | 17.1 |
| DI-TAB ® (unmilled) | 57.0 | 19.0 | 38.0 | 19.0 |
| Colloidal Silicon Dioxide | 3.0 | 1.0 | 2.0 | 1.0 |
| Magnesium Stearate | 3.0 | 1.0 | 2.0 | 1.0 |
| Total | 300.0 | 100.0 | 100.0 | 100.0 |
| Flodex (mm) | 22 | | 16 | |

Example 6

Flow of Dry Powder Blends Containing Compound (1) from Different Lots

Three dry powder blends, each formulated with a different lot of compound (1) were prepared and the flow properties of the resulting blends compared. The sizing and mixing procedure used to prepare the blends was the same as described in Example 5. The compositions and corresponding Flodex numbers are summarized in Table 6. Blend B08-019 and Blend B08-020 exhibited Flodex numbers of 21 mm and 13 mm, respectively. Based on the Flodex numbers for the individual lots of compound (1) (Table 3) one would predict that a blend prepared with compound (1)

Lot 70 would exhibit a Flodex comparable to that of the blend prepared with compound (1) Lot 71. However, the Flodex of the blend formulated with Lot 71 was significantly better than that of the blend formulated with Lot 70; 13 mm versus 21 mm, respectively.

TABLE 6

Flow properties of dry powder blends formulated with different lots of compound (1).

| Blend Component | Blend B08-017 Composition | | Blend B08-019 Composition | | Blend B08-020 Composition | |
|---|---|---|---|---|---|---|
| | wt (g) | wt-% | wt (g) | wt-% | wt (g) | wt-% |
| Compound (1) Lot 4 | 7.5 | 10.0 | — | — | — | — |
| Compound (1) Lot 70 | — | — | 7.5 | 10.0 | — | — |
| Compound (1) Lot 71 | — | — | — | — | 7.5 | 10.0 |
| AVICEL ® PH200 | 14.25 | 19.0 | 14.25 | 19.0 | 14.25 | 19.0 |
| METHOCEL ™ K4M DC | 24.68 | 32.9 | 24.68 | 32.9 | 24.68 | 32.9 |
| EUDRAGIT ® RLPO | 12.83 | 17.1 | 12.83 | 17.1 | 12.83 | 17.1 |
| DI-TAB ® (unmilled) | 14.25 | 19.0 | 14.25 | 19.0 | 14.25 | 19.0 |
| Colloidal Silicon Dioxide | 0.75 | 1.0 | 0.75 | 1.0 | 0.75 | 1.0 |
| Magnesium Stearate | 0.75 | 1.0 | 0.75 | 1.0 | 0.75 | 1.0 |
| Total | 75.0 | 100.0 | 75.0 | 100.0 | 75.0 | 100.0 |
| Flodex (mm) | 13 | | 21 | | 13 | |
| Bulk Density (g/cm³) | 0.25 | | 0.25 | | 0.29 | |
| Tap Density (g/cm³) | 0.36 | | 0.38 | | 0.41 | |
| Can Index (% compressibility) | 32 | | 34 | | 30 | |

Example 7

Flow of Dry Powder Blends Containig Compound 1 and EUDRAGIT® RLPO or EUDRAGIT® RSPO Two dry powder blends each formulated with a different grade of EUDRAGIT® were prepared. Sixteen-point-five (16.5) g of AVICEL® PH200, 32.9 g of METHOCEL™ K4M DC, and 22.1 g of EUDRAGIT® RLPO were passed sequentially through a 20 mesh sieve into a common container. Sixteen-point-five (16.5) g DI-TAB® and 1.0 g of colloidal silicon dioxide were pre-mixed, sized through the 20-mesh sieve, and added to the sized powders. The powders were tumble-mixed for 5 minutes in a V-blender. Next, half of the mixed and sized powders was removed. Ten (10.0) g of compound (1), previously sized through a 20-mesh sieve, was spread as a uniform layer over the half-bed of powder. The removed half of the powder bed was then applied over the layer of compound (1) and the resulting tri-layer composition tumble-mixed for 5 minutes. Finally, 1.0 g of magnesium stearate, previously sized through a 40-mesh sieve, was added to the mixture and tumble-mixed in the V-blender for 3.5 minutes to form Blend E08-007.

A second blend was prepared using a similar mixing procedure. Blend E08-013 was identical in composition except EUDRAGIT® RSPO replaced the EUDRAGIT® RLPO. The compositions of both blends are provided in Table 7.

TABLE 7

Composition of dry powder blends formulated with compound (1).

| Blend Component | Blend E08-007 Composition | | Blend E08-013 Composition | |
|---|---|---|---|---|
| | wt (g) | wt % | wt (g) | wt % |
| Compound (1) Lot 4 | 10.0 | 10.0 | 10.0 | 10.0 |
| AVICEL ® PH200 | 16.5 | 16.5 | 16.5 | 16.5 |
| METHOCEL ™ K4M (DC) | 32.9 | 32.9 | 32.9 | 32.9 |
| EUDRAGIT ® RLPO | 22.1 | 22.1 | — | — |
| EUDRAGIT ® RSPO | — | — | 22.1 | 22.1 |
| DI-TAB ® (unmilled) | 16.5 | 16.5 | 16.5 | 16.5 |
| Colloidal Silicon Dioxide | 1.0 | 1.0 | 1.0 | 1.0 |
| Magnesium Stearate | 1.0 | 1.0 | 1.0 | 1.0 |
| Total | 100.0 | 100.0 | 100.0 | 100.0 |

Example 8

Dissolution Profiles of Tablet Formulations

The blends described in Example 5 and Example 6 were compacted into tablets weighing 100 mg using ¼-inch round standard biconvex tablet tooling and dies. Tablets of each type were tested for dissolution of drug in a USP paddle apparatus (Type II) in 900 mL of 50 mM sodium phosphate monobasic, pH 6.8, at a temperature of 37° C. The paddle stirring speed was 75 revolutions per minute. During the dissolution test, the tablets were contained within a stainless steel cage to position the tablets at the bottom of each vessel.

Tablets comprising EUDRAGIT® RLPO (i.e., Blend E08-007) are also referred to as SR4-10 tablet formulations.

Figure 3:
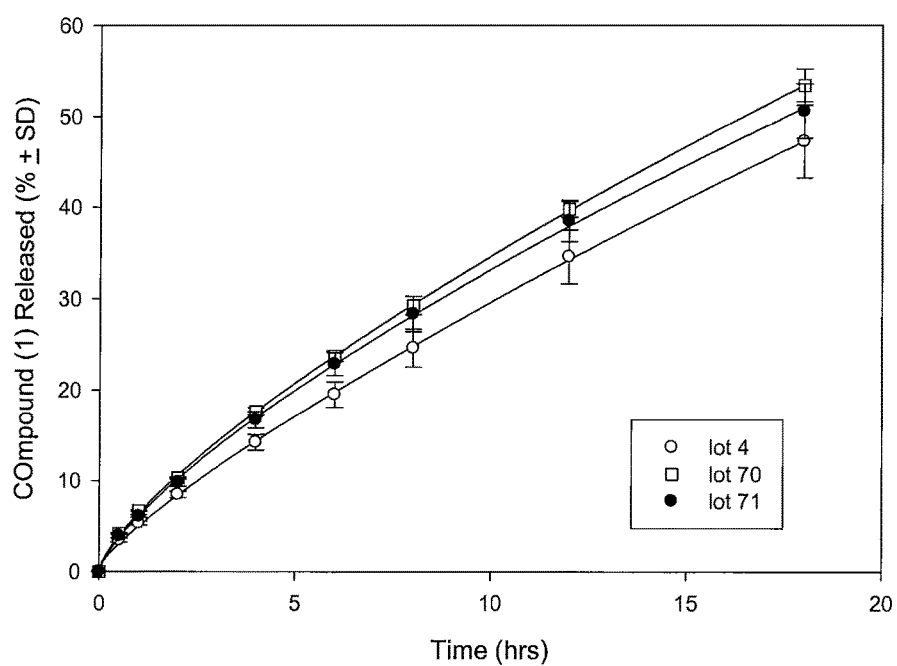
FIG. 3 shows dissolution profiles for tablets containing different lots of compound (1).

Dissolution profiles showing the cumulative percent compound (1) released from a tablet over time for tablets prepared using the blends described in Example 6 are shown in FIG. 3.

Figure 4:
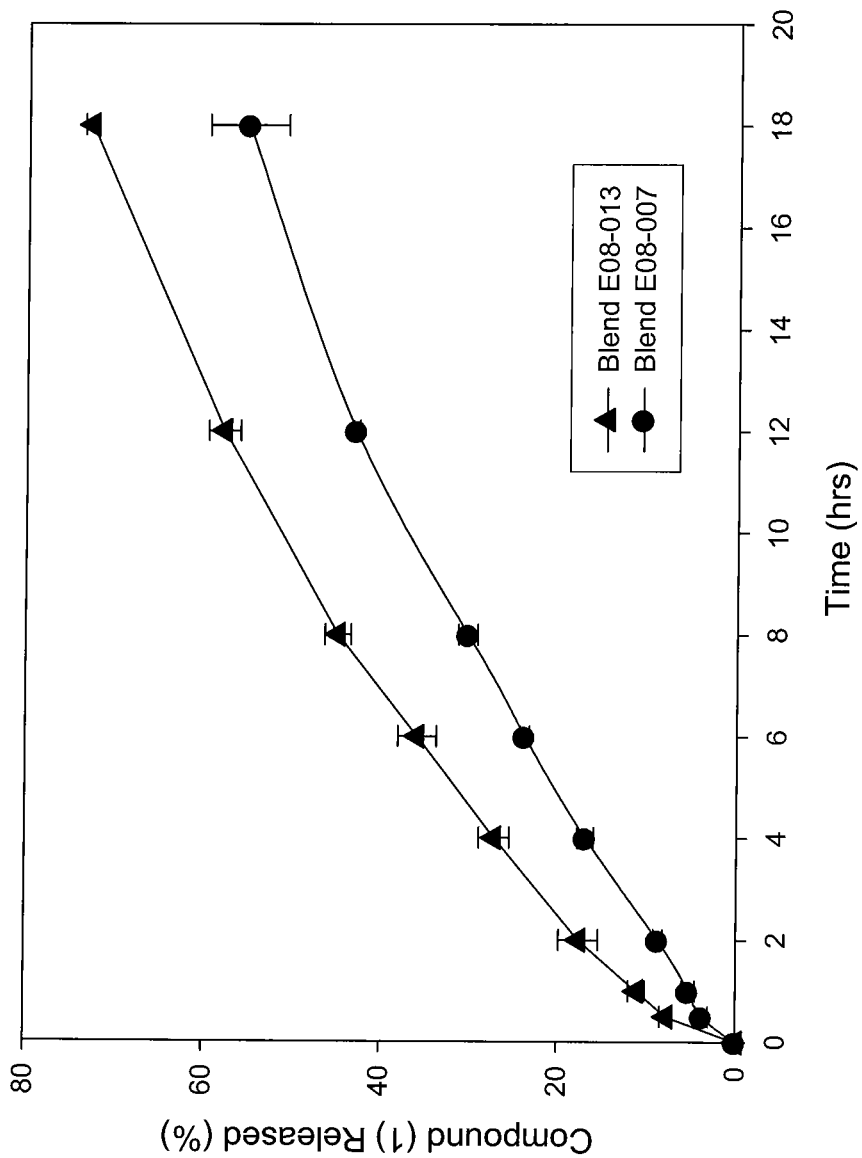
FIG. 4 shows dissolution profiles for tablets containing different grades of EUDRAGIT®.

Dissolution profiles showing the cumulative percent compound (1) released from a tablet over time for tablets prepared using the blends described in Example 7 are shown in FIG. 4. The dissolution profile of the tablets formulated with EUDRAGIT® RSPO is illustrated in the profile with triangular symbols and the dissolution profile of tablets formulated with EUDRAGIT® RLPO is illustrated by the profile with the circular symbols.

Example 9

Preparation and Characterization of 20 mg Compound (1) Tablets (SR4-20)

Tablet batches were manufactured on a pilot scale to assess the feasibility of maintaining acceptable tablet weight and drug content in blending and tableting operations. A powder blend was prepared by passing in order 1,140 g of AVICEL® PH200, 1,974 g of METHOCEL™ K4M DC, 1,026 g of EUDRAGIT® RLPO, 1,140 g of DI-TAB®, and 60 g of colloidal silicon dioxide, through a Russell Finex sifter (Russell Finex, Pineville, N.C.) fitted with a 20-mesh screen. The sized powders were transferred to a one cubic foot V-blender and tumble-mixed for 5 minutes. Approximately 2,670 g of the blend was removed and set aside. Six-hundred (600) g of compound (1) (Lot 4), previously manually passed through a 20-mesh sieve, was spread as a uniform layer over the half-bed of powder remaining in the blender. The 2,670 g of previously removed powder was returned to the blender and the three-layer mixture blended for 5 minutes. Finally, 60 g of magnesium stearate, pre-sifted through a 40-mesh screen, was added to the blend and the mixture blended for 4 minutes to complete the mixing and blending operation of the 6,000 g batch.

Figure 5:
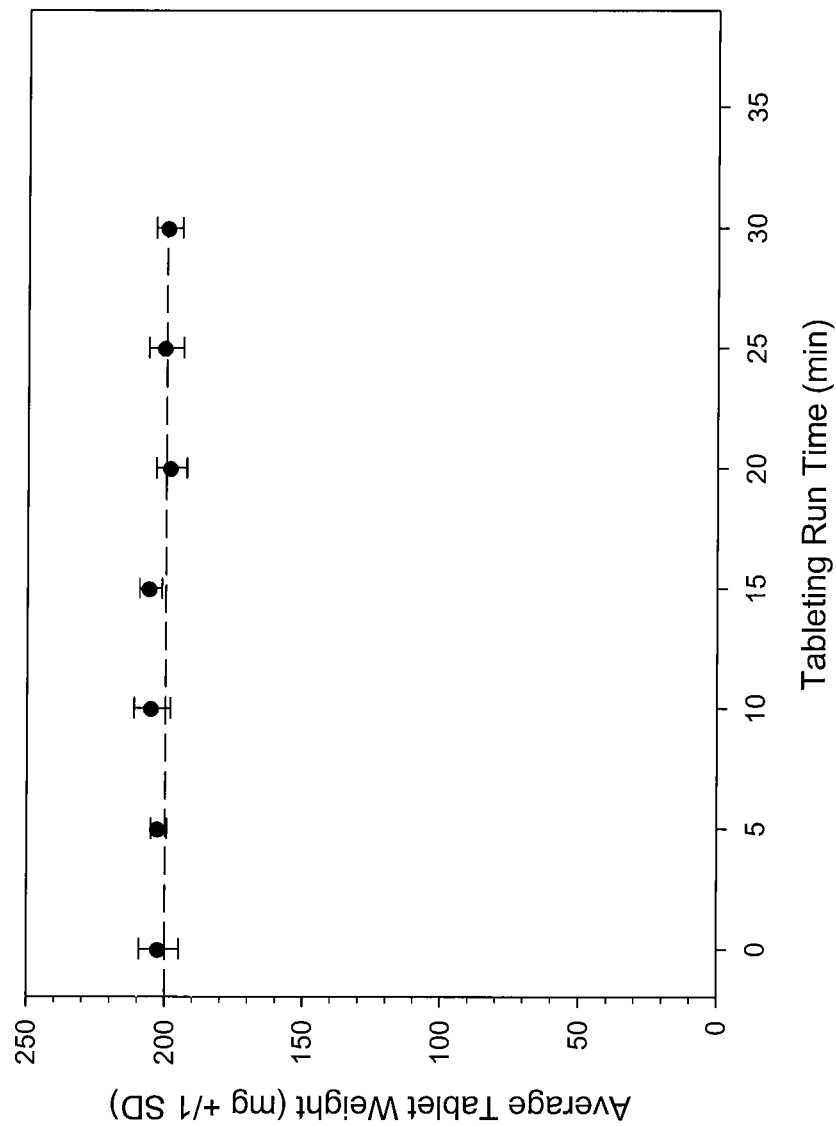
FIG. 5 shows the weight uniformity of 20 mg tablets.

Two-thousand four hundred (2,400) g of the resulting blend was transferred to the hopper of a Kilian T100 rotary tablet press (Kilian & Co., Inc., Horsham, Pa.) fitted with ⁵⁄₁₆-inch standard round concave punch tooling. Tablets were compressed at a rate of 180 tablets per minute with a nominal target weight of 200 mg per tablet. Samples of tablets were collected approximately every 5 minutes and tablet weight measured. The average weight of ten tablets was determined at each time point. The tablet weight histogram shown in FIG. 5 demonstrates that tablet weight is well maintained. Average weight was maintained to within ±5% of the 200 mg target weight (20 mg compound (1) per tablet).

The content of compound (1) in the tablets was also determined. Three tablets collected at each of nine points were analyzed for compound (1) by high pressure liquid chromatography using an Alltech Platinum EPS $C_{18}$ column (4.6×150 mm, 3 μm, 100 Å) (Alltech Associates, Inc., Deerfield, Ill.) at 35° C. with a flow rate of 1.2 mL/min. The mobile phase was 0.02 M $KH_2PO_4$, pH 2.5/water/acetonitrile, 461/44/495 (v/v/v), and the detection wavelength was 220 nm. Tablets were dissolved in 1% (w/v) sodium dodecyl sulfate (SDS) in acetonitrile:water (80:20) and sonicated for 30 minutes (target concentration 0.2 mg/mL compound (1)). All samples were filtered with a 0.45 μm nylon filter prior to analysis. The addition of a small amount of surfactant (i.e., sodium dodecylsulfate (SDS)) has been shown to minimize binding of the drug to insoluble excipients, resulting in improved drug extraction efficiency.

Figure 6:
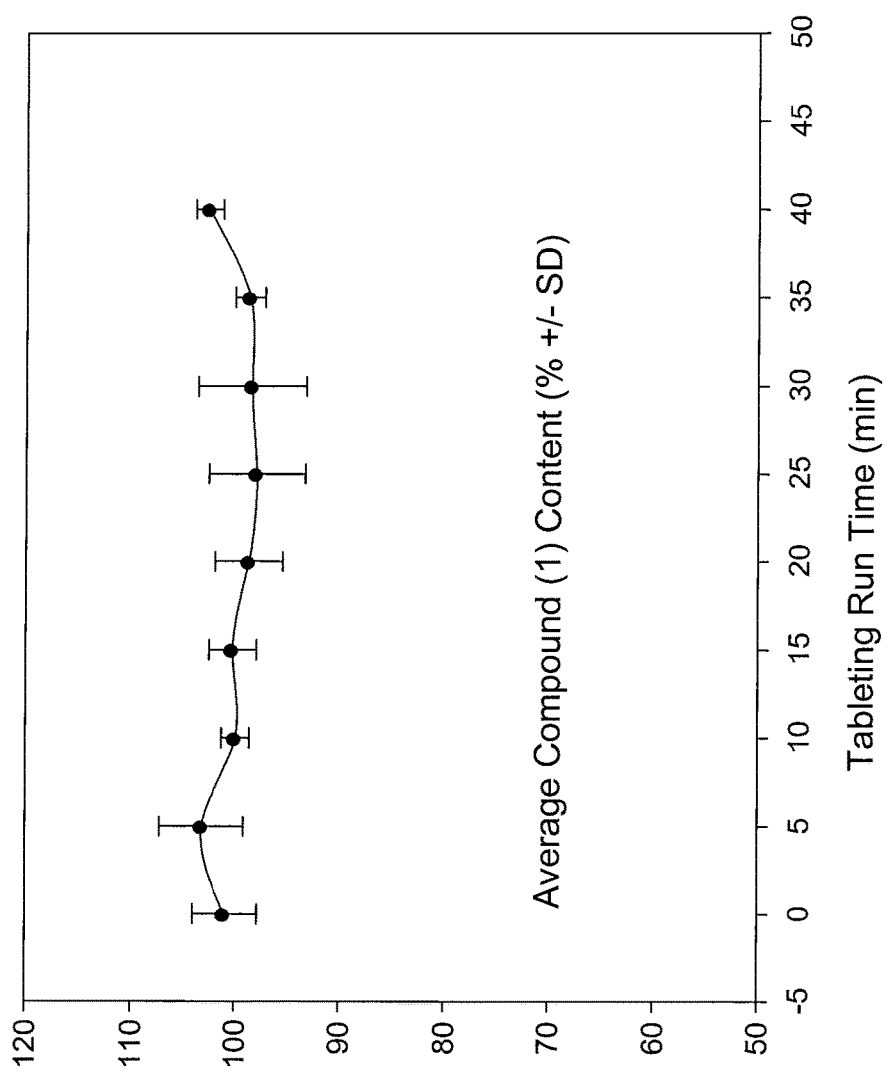
FIG. 6 shows the content uniformity of 20 mg tablets.

The compound (1) content histogram for the tablets is shown in FIG. 6 and is based on a target compound (1) content of 20 mg. Tablet samples were obtained at intervals during a tableting run, wherein the intervals are identified as percent (%) of the total tableting run (100%). A compound (1) content of 20 mg per tablet is equivalent to 100% on the graph ordinate. Average compound (1) content per tablet was well maintained to within ±5% of the target dose at all time points. The range of compound (1) content in individual tablets ranged from a low of 92.6% to a high of 105.7% of the target compound (1) content of 20 mg.

Figure 7:
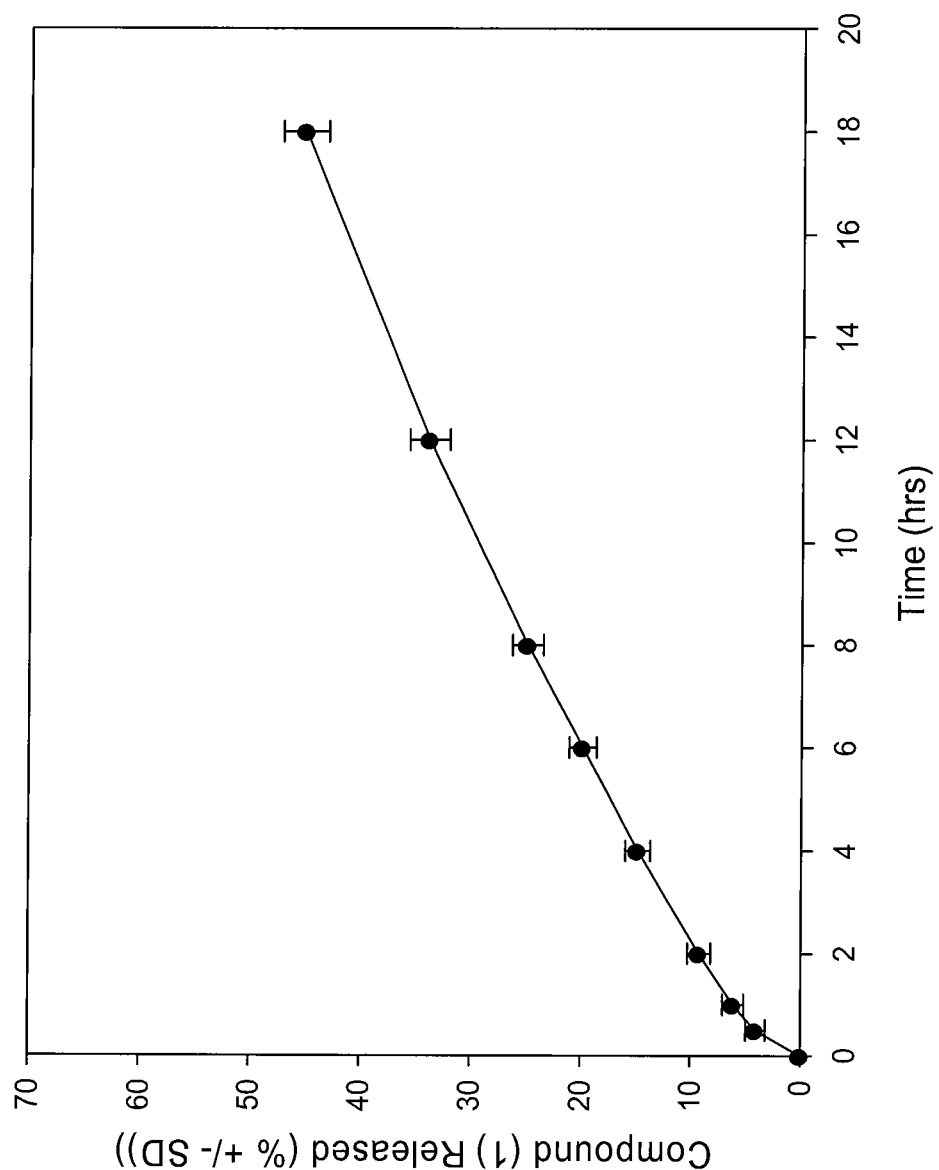
FIG. 7 shows the dissolution profile of 20 mg tablets.

The thickness of tablets was measured with dial calipers to be approximately 4.02 mm The crushing strength of tablets was measured on a tablet hardness tester to be approximately 8.1 kiloponds. The tablets were tested for dissolution using the procedures described in Example 6. Average cumulative release of compound (1) from the 20 mg tablets at 18 hours determined according to Example 8 was about 45% as shown in FIG. 7.

Example 10

Preparation and Characterization of 30 mg Compound (1) Tablets (SR4-30)

Figure 8:
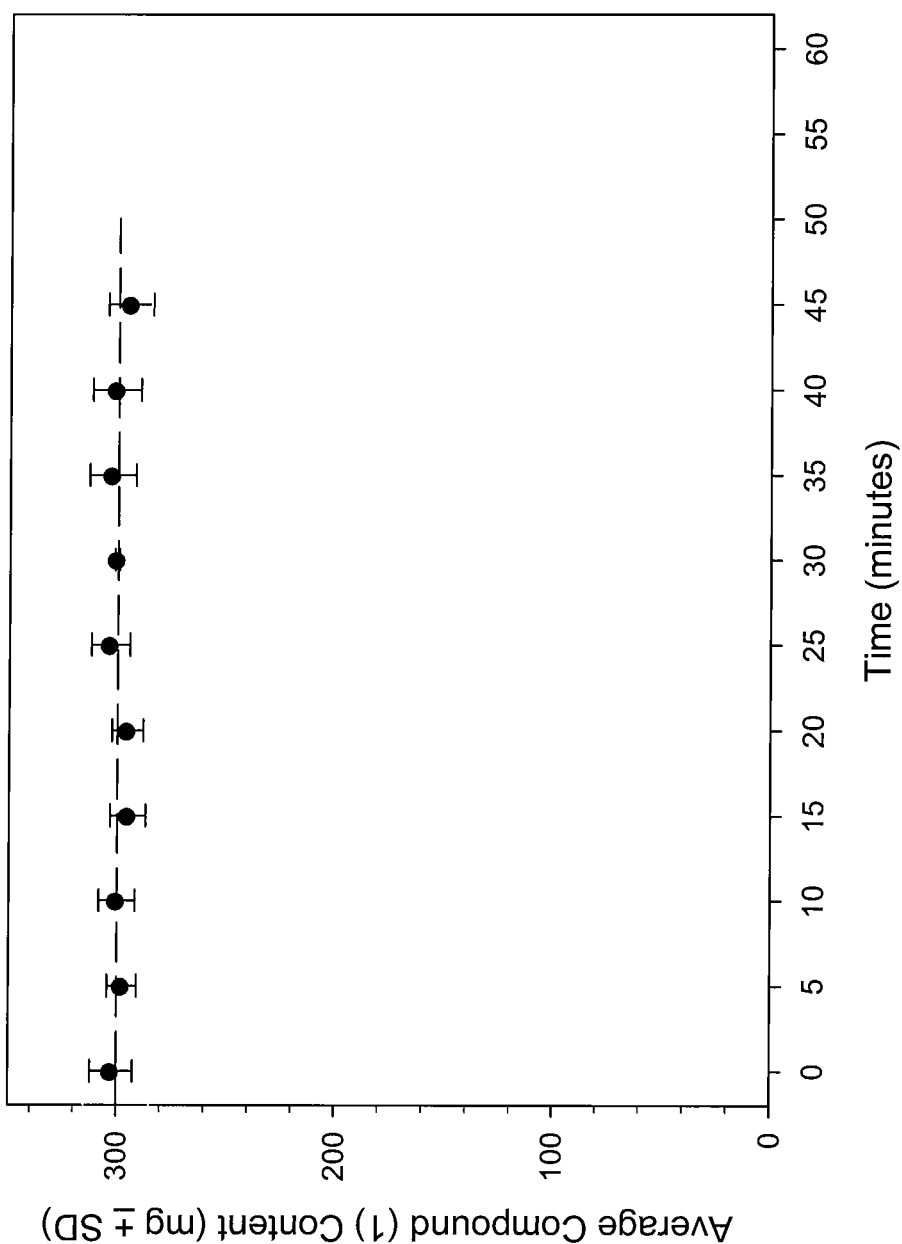
FIG. 8 shows the weight uniformity of 30 mg tablets.

Three-thousand six hundred (3,600) g of the blend described in Example 9 was transferred to the hopper of the Kilian T100 rotary tablet press fitted with ⅜ inch standard round concave punch tooling. Tablets were compressed at a rate of 180 tablets per minute with a nominal target weight of 300 mg per tablet (30 mg compound (1) per tablet). Samples of tablets were collected approximately every 5 minutes and tablet weight measured. The average weight of ten tablets was determined at each point. The tablet weight histogram in FIG. 8 demonstrates that tablet weight was well maintained within 5% of the 300 mg target weight.

Figure 9:
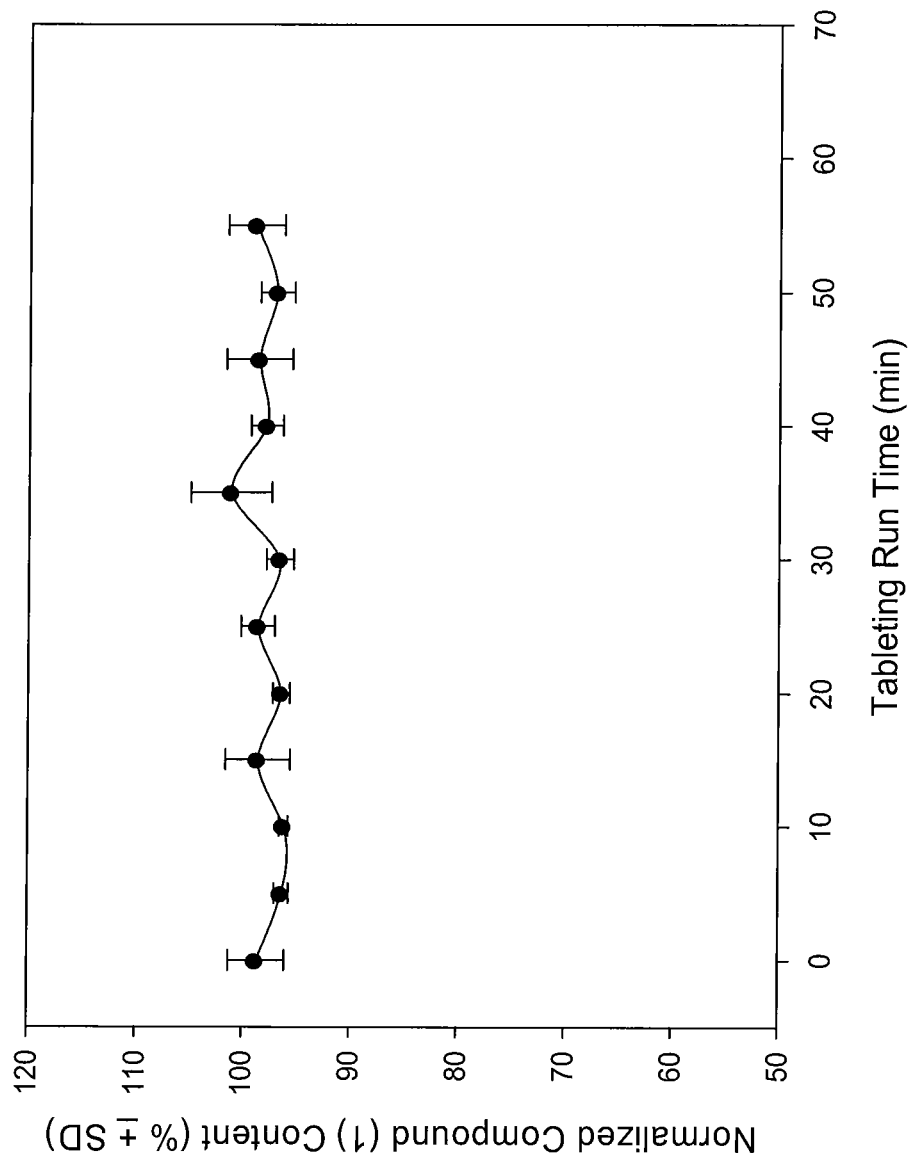
FIG. 9 shows the content uniformity of 30 mg tablets.

The content of compound (1) in tablets was also monitored. Three tablets collected at each of twelve time points were analyzed for compound (1) using HPLC as described in Example 9. The histogram of compound (1) content is shown in FIG. 9. A compound (1) content of 30 mg per tablet equals a target content of 100% on the graph ordinate. Average drug content per tablet was well maintained to within ±5% of the target amount of 30 mg throughout the tableting run. The range of drug content in individual tablets ranged from a low of 95.0% to a high of 103.6% of the 30 mg target weight.

Figure 10:
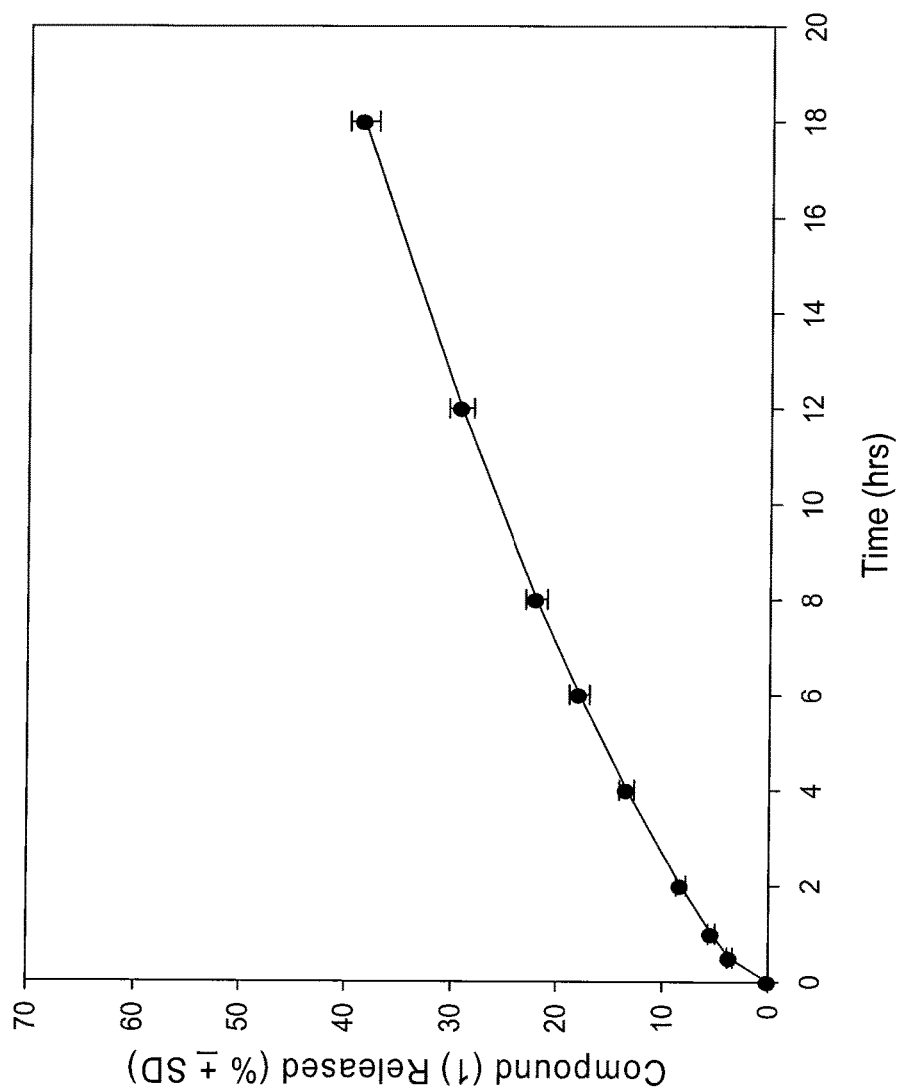
FIG. 10 shows the dissolution profile of 30 mg tablets.

The thickness of tablets was measured with dial calipers to be approximately 4.18 mm. The crushing strength of tablets was measured on a tablet hardness tester to be approximately 9.5 kiloponds. The tablets were tested for dissolution using the procedures described in Example 8. The average cumulative release of compound (1) from the 30 mg tablets at 18 hours determined according to Example 8 was about 39% as shown in FIG. 10.

Example 11

Preparation and Characterization of 10 mg Compound (1) Tablets (Sr4-10)

Sustained release tablets comprising 10 mg compound (1) and weighing about 175.1 mg were prepared using procedures similar to those described in Examples 9 and 10. The composition of the SR4 tablet dosage forms is summarized in Table 8.

TABLE 8

Composition of SR4 tablet dosage forms.

| Component | SR4-10 wt-% | SR4-10 wt/tablet (mg) | SR4-20 wt-% | SR4-20 wt/tablet (mg) | SR4-30 wt-% | SR4-30 wt/tablet (mg) |
|---|---|---|---|---|---|---|
| Compound (1) Lot 4 | 5.71 | 10.0 | 10.0 | 20.0 | 10.0 | 30.0 |
| AVICEL ® PH200 | 21.13 | 37.0 | 19.0 | 38.0 | 19.0 | 57.0 |
| METHOCEL ™ K4M (DC) | 32.90 | 57.6 | 32.9 | 65.8 | 32.9 | 98.7 |
| EUDRAGIT ® RLPO | 17.08 | 29.9 | 17.1 | 34.2 | 17.1 | 51.3 |
| DI-TAB ® (unmilled) | 21.13 | 37.0 | 19.0 | 38.0 | 19.0 | 57.0 |
| Colloidal Silicon Dioxide | 1.03 | 1.8 | 1.0 | 2.0 | 1.0 | 3.0 |
| Magnesium Stearate | 1.03 | 1.8 | 1.0 | 2.0 | 1.0 | 3.0 |
| Total | 100.0 | 175.1 | 100.0 | 200.0 | 100.0 | 300.0 |

Example 12

Preparation of 10 mg Compound (1) SR3 Tablets

Sustained release tablets comprising compound (1) and an ammonioalkyl methacrylate polymer, EUDRAGIT® RL 30D, (SR3) were prepared in a 300 g batch size.

The following amounts of the components were used to prepare a 300 g batch: 12.0 g of compound (1), 128.7 g of microcrystalline cellulose (AVICEL® PH200, FMC Corp., Philadelphia, Pa.), 106.5 g of hydroxypropylmethyl cellulose METHOCEL™ K4M (METHOCEL™ K4M, Dow Chemical), 51.3 g of ammonioalkyl methacrylate copolymer (EUDRAGIT® RL 30D, Degussa), and 1.5 g of magnesium stearate (HYQUAL® vegetable source, Mallinckrodt, Phillipsburg, N.J.). The amount of the components in sustained release tablets (SR3) comprising 10 mg compound (1) and an ammonioalkyl methacrylate polymer is provided in Table 9.

TABLE 9

Composition of SR3 sustained release tablets.

| Ingredient | Amount (mg/tablet) | Composition (wt %) | Ingredient Category |
|---|---|---|---|
| Compound (1) | 10.00 | 4.0 | Prodrug |
| EUDRAGIT ® RL 30D | 42.75 | 17.1 | pH-independent release control polymer, granulating fluid |
| AVICEL ® PH200 | 107.25 | 42.9 | Matrix material |
| EUDRAGIT ® RL 30D | 88.75 | 35.5 | Binding agent |
| Magnesium stearate | 1.25 | 0.5 | Lubricant |
| Total | 250.00 | 100.0 | |

Compound (1) (12 g), microcrystalline cellulose (AVICEL® PH200, FMC Biopolymer) (127.8 g), and hydroxypropylmethyl cellulose (METHOCEL™ K4M SP, Dow Chemical Co.) (106.5 g) were weighed, screened through a #20 mesh stainless steel screen, and mixed in a V-blender (2 quart, Model MB-1, Globepharma, New Brunswick, N.J.) for 5 minutes.

The blend was discharged and wet granulated at high shear using a KG-5 Mixer/Granulator with a 1 L bowl (Key International, Englishtown, N.J.). Wet granulation was performed using 100 mL of water, a tubing dimension of 1 mm, an impeller speed of 250 rpm, and a chopper speed of 1500 rpm.

The wet granulate was then dried in a Fluid Bed Model 0002 (Fluid Air, Aurora, Ill.) granulator/drier using an inlet from of 25 SCFM, an inlet air temperature of 45° C., an outlet air temperature of less than 30° C., and a filter pressure of 200-900 mm H$_2$O. The target weight loss on drying was less than about 3%.

The dried product was passed through a Comil Model U5 mill (Quadro Engineering, Inc., Millburn, N.J.) using a 0.079 inch grater-type screen (ID No. 7L079G03123-(2007) 0503) and a stainless steel, 150 grit (Ra 1.06) surface finish, at an operating speed of 2500 rpm to obtain the milled material for further compression.

The granulate was returned to the KG-5 Mixer/Granulator and coated with a blend comprising an ammonioalkyl methacrylate copolymer and excipients by adding 171 g of EUDRAGIT® RL 30D (Type A, an ammonioalkyl methacrylate copolymer 30% aqueous dispersion characterized by a molecular weight from about 125,000 Daltons to about 175,000 Daltons, available from Degussa) (51.3 g solids) at 2.4 mL/min while mixing at an impeller speed of 250 rpm and a chopper speed of 1500 rpm. The granules were then dried.

Magnesium stearate (1.5 g) (HYQUAL® vegetable source) was weighed and passed through a #40 mesh screen. The milled material and the magnesium stearate were added to the V-blender and blended for 5 minutes at 25 rpm.

The blended material was discharged and compressed to form tablets having a total weight of 250 mg and a compound (1) loading of 10 mg (4 wt-%). A 10 station, Mini Press-IIBD (Globepharma, New Brunswick, N.J.) fitted with 5/16-in diameter IPT standard concentric upper and lower punches and a 5/16-in (ID)×1.1875 OD straight bore steel die was used to compress the tablets. The tablets had a mean final hardness of from about 6 kp to about 9 kp (59 to 88 Newtons).

Example 13

Chemical Stability of Compound (1) in Tablet Formulations

Open dish chemical stability of compound (1) under various conditions of temperature and humidity were determined for SR3-10 and SR4-10 tablet formulations. The tablets were exposed to temperature and humidity for up to 3 months, and the amount of R-baclofen and lactam degradant (R-(4-chloro-phenyl)-pyrrolidin-2-one) were determined. The results are presented in Table 10. The SR4-10 formulation exhibited superior chemical stability compared to the SR3-10 formulation as shown by consistently lower lactam levels at each storage condition at 3-months.

TABLE 10

Chemical stability of compound (1) in tablet formulations.

| Dosage Form | Impurity | 0 Months 5° C. | 1 Month | | | 3 Months | | | |
|---|---|---|---|---|---|---|---|---|---|
| | | | 5° C. | 25° C./ 60% | 40° C./ 20% | 40° C./ 75% | 5° C. | 25° C./ 60% | 40° C./ 20% | 40° C./ 75% |
| SR3-10 | R-baclofen | ND | ND | ND | <0.1 | 0.24 | ND | <0.1 | <0.1 | 0.77 |
| | lactam | ND | ND | ND | <0.1 | 0.09 | <0.1 | <0.1 | 0.13 | 0.77 |
| | Total | ND | ND | * | 0.1 | 0.3 | 0.0 | 0.1 | 0.2 | 1.5 |
| SR4-10 | R-baclofen | ND | ND | * | 0.05 | 0.36 | * | * | 0.06 | 0.67 |
| | lactam | ND | ND | ND | ND | | ND | ND | * | 0.38 |
| | total | ND | ND | * | * | 0.4 | * | * | 0.1 | 0.1 |

* <0.05% (LOQ);
ND = not detected;
values represent wt-%.

Example 14

Steady State Pharmacokinetics of R-Baclofen in Human Patients Following Administration of Tablet Dosage Forms Comprising Compound (1)

A randomized, multiple-dose, four-treatment, four-period cross-over study comparing the steady state pharmacokinetics of 10 mg SR3 and 10 mg, 20 mg, and 30 mg SR4 tablet formulations in fed healthy adult volunteers was performed.

Prior to dosing on study day 1, patients were randomized into one of four sequences. On day 1, all patients received a 20 mg (2×10 mg) dose of compound (1) as a SR3 tablet within 10 minutes of eating breakfast. On day 2, all patients received a 30 mg (3×10 mg) dose of compound (1) as a SR3 tablet within 10 minutes of completing breakfast. On day 3, all patients received 40 mg (4×10 mg) dose of compound (1) as an SR3 tablet within 10 minutes of completing breakfast.

Patients received one of the following four treatments in a randomized manner during Period 1 (days 4 through 7), Period 2 (days 8 through 11), Period 3 (days 12 through 15) and Period 4 (days 16 through 19):

Treatment A: 6×10 mg compound (1) SR3 tablets once a day (QD) within 10 minutes of completing breakfast, for 4 days;

Treatment B: 6×10 mg compound (1) SR4-10 tablets once a day (QD) within 10 minutes of completing breakfast, for 4 days;

Treatment C: 3×20 mg compound (1) SR4-20 tablets once a day (QD) within 10 minutes of completing breakfast, for 4 days; and Treatment D: 2×30 mg compound (1) SR4-30 tablets once a day (QD) within 10 minutes of completing breakfast, for 4 days.

Each treatment group contained sixteen (16) healthy adult volunteers.

Blood samples (approximately 4 mL) were collected from patients prior to dosing and at time intervals post-dosing into tubes containing K2EDTA. Blood sample aliquots were quenched immediately with methanol to prevent further hydrolysis of compound (1). Two aliquots (1 mL each) were immediately transferred to Nalgene tubes and quenched with 3 mL methanol. Blood sample aliquots were stored in a freezer at −80° C. The blood sample aliquots were analyzed for R-baclofen and compound (1) in whole blood supernatant using sensitive and specific LC-MS/MS methods.

Concentration data for R-baclofen and compound (1) in blood was analyzed by noncompartmental methods using WINNONLIN™ Software version 4.1 (Pharsight Corporation, Mountain View, Calif.). Concentration data and pharmacokinetics parameters were plotted using SIGMA-PLOT™ version 9.0 (Systat Software Inc., Point Richmond, Calif.). Actual time points were used for the calculation of pharmacokinetic parameters. The maximum observed drug concentration ($C_{max}$) and time to $C_{max}$ ($T_{max}$) were obtained by observation. The apparent elimination half-life ($T_{1/2}$) was determined by linear regression of three or more log-transformed data points in the terminal phase (calculated as $\ln(2)/K_{el}$ where $K_{el}$ is the terminal elimination rate constant calculated by linear regression of the terminal linear portion of the log concentration vs. time curve). The area under the linear regression models were fit for AUC versus dose and for $C_{max}$ versus dose using SAS™ version 9.1 for Windows (SAS Institute, Cary, N.C.). In both models, the dose effect was parameterized using orthogonal polynomial coefficients for unequally spaced values.

Blood samples were obtained on days 7, 11, 15, and 19. Following Period 4, patients were tapered off the regimen over a period of 4 days. During the course of the study patients were provided standardized clinic meals (approximately 30% calories from fat) with a total daily caloric content of approximately 2000 kcal.

Figure 11:
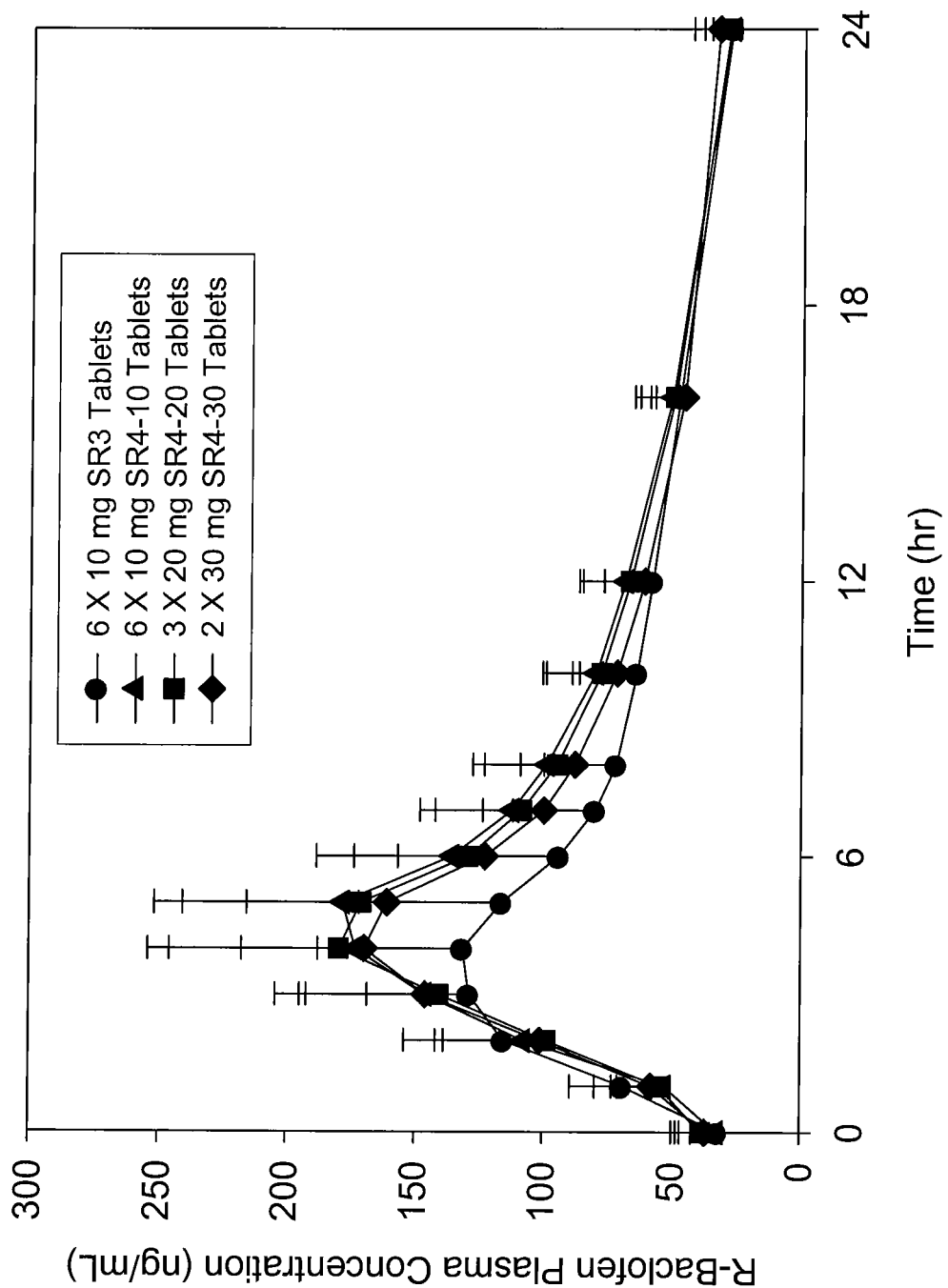
FIG. 11 shows steady state R-baclofen pharmacokinetic profiles in blood of healthy volunteers following administration of SR3 and SR4 dosage forms.

The mean pharmacokinetic parameters for R-baclofen in blood determined at steady state during the four treatments are summarized in Table 1, and the pharmacokinetic profiles are shown in FIG. 11. $AUC_{ss,24}$ values for the three SR4 formulations ranged from about 1750 ng×hr/mL to about 1850 ng×hr/mL compared to the $AUC_{ss,24}$ of about 1500 ng×hr/mL for the SR3 formulation.

Example 15

SR4 Tablets Prepared Using Unstructured Powder Composition (Bench Scale)

A 500 gram powder blend was prepared. First, 28.6 grams of compound (1) was passed through a 20-mesh sieve with a spatula and the resulting sized drug set aside. Then, 105.7 g of AVICEL® PH200, 164.5 g of METHOCEL™ K4M direct compression grade (DC), 85.4 g of EUDRAGIT® RLPO, 5.2 g silicon dioxide grade M5P, and 105.7 g of dibasic calcium phosphate dihydrate as DI-TAB® were passed sequentially through a 20-mesh sieve using a spatula. The sized excipient powders were then transferred to a 2-quart twin-shell blender and tumble mixed for 5 minutes at a rotation speed of 25 revolutions per minute. Two-hundred thirty-three (233) grams of the resulting sized and mixed excipient powders were removed. The sized compound (1) was then spread as a uniformly thick layer over the half bed of powders in the mixer. The 233 grams of removed powders were returned to the shell of the blender and the tri-layer composition was blended for 5 minutes at 25 rpm. Next, 5.2 g of magnesium stearate was passed with a spatula through a 60-mesh sieve and added to the powder bed. Finally, the bed of powders was tumble mixed for 4 minutes at 25 rpm. This formed the unstructured powder blend.

The resulting unstructured powder blend was transferred to the hopper of a Korsch XL 100 tablet press having two stations fitted with 5/16 inch round standard concave tooling (Korsch America Inc., South Easton, Mass.). The powders were compressed into tablets having a nominal weight of 175 mg such that each tablet contained a nominal content of compound (1) of 10 mg. At the beginning and during the compression process, samples of tablets were collected. The resulting tablet samples were analyzed for the content of compound (1) by high performance liquid chromatography. Additionally, the tablet samples were analyzed for DI-TAB® content using ion chromatography.

Figure 12:
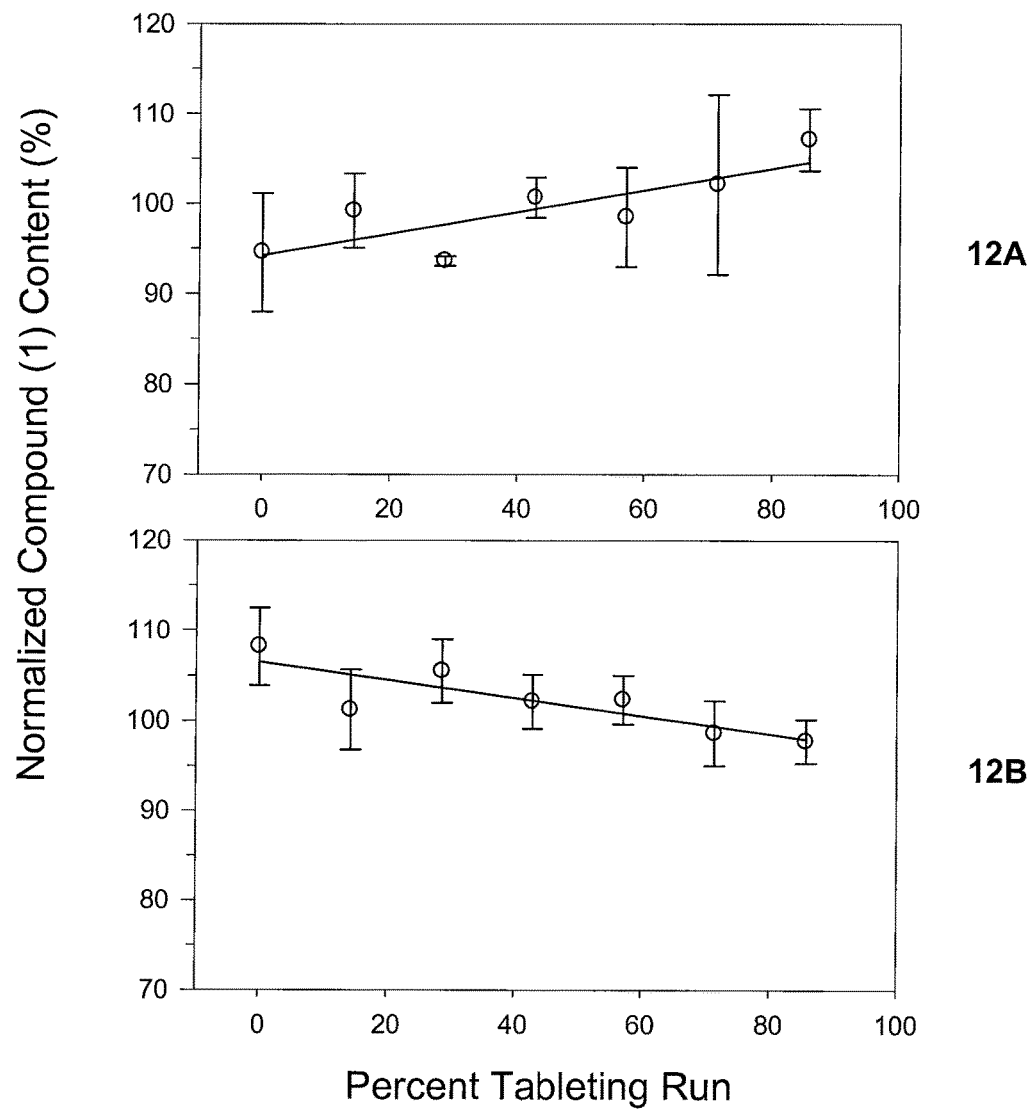
FIG. 12 shows tablet uniformity parameters for (A) compound (1) and (B) DI-TAB® in SR4 tablets prepared using an unstructured powder composition.

The resulting tablet content data are plotted in FIG. 12. FIG. 12A shows the content of compound (1) in tablets during a tableting run. Each data point represents the average content of compound (1) in three tablets relative to the target amount of 10.0 mg compound (1) sampled a particular point during a tableting run and represented as a percent (%) of the entire tableting run (100%). The error bars for each data point represent the relative standard deviation of the three measured values at each time point. The slope of the linear regression fit to the compound (1) content data was +0.121. The relative standard deviation of compound (1) content throughout the run was 6.34%. FIG. 12B shows the content of DI-TAB® within each tablet during the same tableting run. The slope of the linear regression fit to the DI-TAB® content data was −0.099. The relative standard deviation of DI-TAB® content throughout the run was 5.60%.

These histograms reveal that the content of compound (1) in the tablets is low at the beginning of the tableting run. Additionally, the content of compound (1) within the tablets increases during the tableting run. It is also clear that the content of compound (1) is high at the end of the run. Moreover, the content of the DI-TAB® within the tablets follows the opposite trend. The content of DI-TAB® is high at the beginning of the run and steadily decreases throughout the tableting run.

This phenomenon is explained by the unstructured nature of the powder blend used to prepare these tablets and the bulk density of the major components comprising the blend. The bulk density values of the major components within this unstructured blend are summarized in Table 11.

TABLE 11

Bulk density of Example 15 blend composition.

| Major Component | Bulk Density (g/cc) |
| --- | --- |
| Compound (1) | 0.15 |
| AVICEL ® PH200 | 0.30 |
| METHOCEL ™ K4M (DC) | 0.14 |
| EUDRAGIT ® RLPO | 0.39 |
| DI-TAB ® (unmilled) | 0.92 |

The density of the DI-TAB® exceeds the density of any other component. It is in more than twice as dense as any other component within the blend. Therefore, within the unstructured powder blend, simple handling and processing of the blend induces sufficient vibration to cause the denser DI-TAB® component to settle under the force of gravity to the bottom of the blend. In so doing, the less dense components such as baclofen prodrug compound (1) are displaced to the top of the blend. When the blend was fed to the hopper of the tablet press, the lowest portion of the unstructured powder bed, which contains the relatively high fraction of DI-TAB® and relatively low fraction of compound (1) is the first to be converted to tablets. Therefore, the tablets at the beginning of the run have low drug content and high DI-TAB® content. Conversely, the tablets at the end of the tableting run have relatively high drug content and relatively low DI-TAB® content. The linear regression analysis of the data in FIG. 12 therefore reflect a positive slope for the curve representing the content of compound (1) and a corresponding negative slope of similar magnitude for the curve representing the content of DI-TAB®.

Example 16

SR4 Tablets Prepared Using Structured Powder Composition (Bench Scale)

A structured powder blend was prepared. First 33.0 grams of baclofen prodrug compound (1), 5.94 g silicon dioxide M5P, and 122.1 DI-TAB® were placed in a polyethylene bag and tumble mixed for 2 minutes. The pre-mixed powders were then passed though a cone mill (Quadro Comil Model U5, Quadro Engineering Corp., Waterloo, Ontario, Canada). The cone mill was fitted with a screen having round mesh opening with a diameter of 457 microns and operated at an impeller speed of 3000 rpm.

This milling process resulted in DI-TAB® particles that are coated with the baclofen prodrug compound (1) and used to prepare the structured powder blend.

Continuing with the preparation of the structured powder blend, 172.8 grams of METHOCEL™ K4M DC was passed through a 20-mesh sieve and loaded into a 2-quart twin shell blender. Then, 146.4 g of the cone milled compound (1)/DI-TAB®/silicon dioxide mixture was loaded into the twin shell mixture as a uniformly thick layer over the hydroxypropyl methylcellulose. Then, 89.7 g of EUDRAGIT® RLPO and 111.0 g of AVICEL® PH200 were sized through a 20-mesh sieve and loaded into the twin shell mixer. The composition was then tumble mixed for 10 minutes at 25 rpm. One-hundred (100) grams of the mixture was then removed. Five and four-tenths (5.4) g of magnesium stearate was passed through a 40-mesh sieve and stirred with a spatula into the 100 grams of blend. Finally, the 100 gram sample with magnesium stearate was added back to the blend and the entire batch was tumble mixed for 4 minutes at 25 rpm. This formed the structure powder blend.

Figure 13:
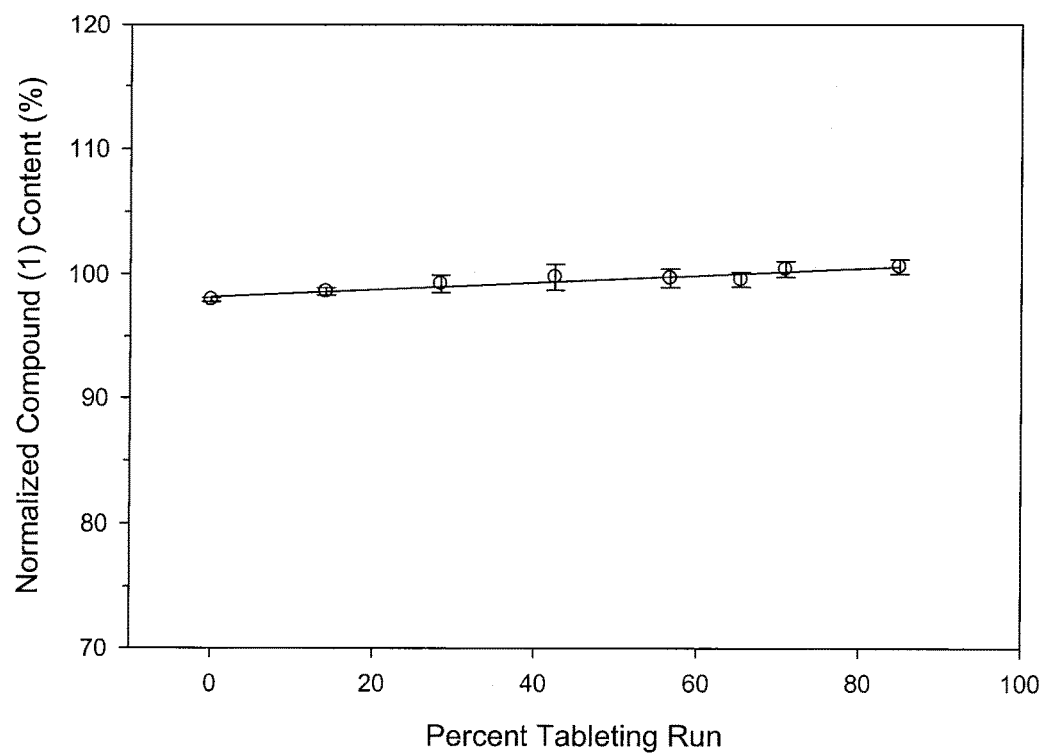
FIG. 13 shows tablet uniformity parameters for compound (1) in SR4 tablets prepared using a structured powder composition.

The resulting structured powder blend was transferred to the hopper of a Korsch XL100 tablet press. The press was fitted with 5/16 inch round standard concave punches and dies set at 2 stations. The blend was compressed into tablets using a nominal target weight of 175 mg to provide a unit dose of 10 mg compound (1). Tablet samples were collected and analyzed according to the procedures described in Example 15. The resulting data are presented in FIG. 13. FIG. 13 shows the tablet content of compound (1) normalized to the target content of compound (1) (±SD) at intervals during the total tableting run (100%). The slope of the linear regression fit to the data was +0.028. The relative standard deviation of compound (1) content throughout the batch was 1.00%.

Comparing the content results of the unstructured blend in FIG. 12 to the results of the structured blend in FIG. 13 shows the significant improvement in compound (1) content uniformity provided by the structured powder blend. The slope of linear regression for the compound (1) content of tablets made from the structured blend is +0.028 compared to the slope for compound (1) content of tablets made from the unstructured blend of +0.121. One skilled in the art will appreciate that the closer the slope is to zero, the more uniform the average content throughout the batch. Likewise, relative standard deviation (RSD) of the contents for the tablets fabricated from the structured powder blend was 1.00%. This indicates much better content uniformity in compound (1) content within the tablets than for tablets made from the unstructured blend which had a relative standard deviation of 6.34%.

Example 17

SR4 Tablets Prepared Using an Unstructured Powder Blend (Pilot Manufacturing Scale)

The following process was used to prepare 6 kg of unstructured powder blend. First, 0.340 kg of compound (1) was hand screened through a sieve having a mesh of 20 wires per inch. Then, 1.258 kg of AVICEL® PH200, 0.061 kg of colloidal silicon dioxide, 1.958 kg of METHOCEL™ K4M (DC), 1.258 kg of DI-TAB®, and 1.017 kg of EUDRAGIT® RLPO were passed through a Finex electric sifter fitted with a 20-mesh sieve (Russell Finex Inc.). The sized excipients were loaded into a 1 cubic foot V-blender and tumble-mixed at a rotation speed of 25 rpm for 5 minutes. Half of the resulting excipient blend was removed. Then, the sized prodrug compound (1) was layered over the half bed of powders. The remaining half bed of excipients was layered over the compound (1). The resulting 3-layer composition was then tumble-mixed in the V-blender at a rotation speed of 25 rpm for 5 minutes. Magnesium stearate (0.061 kg) was passed through a mesh having 40 wires per inch and then added to the bed of powders. The resulting composition was tumble mixed for 4 minutes at 25 rpm. This formed an SR4 blend prepared without high shear mixing.

The resulting 6 kg of blend was fed to a Kilian T100 rotary tablet press fitted with 9 stations of 5/16 inch standard concave round punches and dies (IMA Kilian GmbH & Co. KG, Köln, DE). Tablets were compressed at a speed of 25 rpm with a weight of approximately 175 mg and a hardness of approximately 7 kN. Each tablet contained a nominal content of 10 mg of compound (1). Tablet samples were collected in process approximately every 37,000 tablets. The content of the compound (1) was determined using high performance liquid chromatography in 3 tablets at each sampling point.

Figure 14:
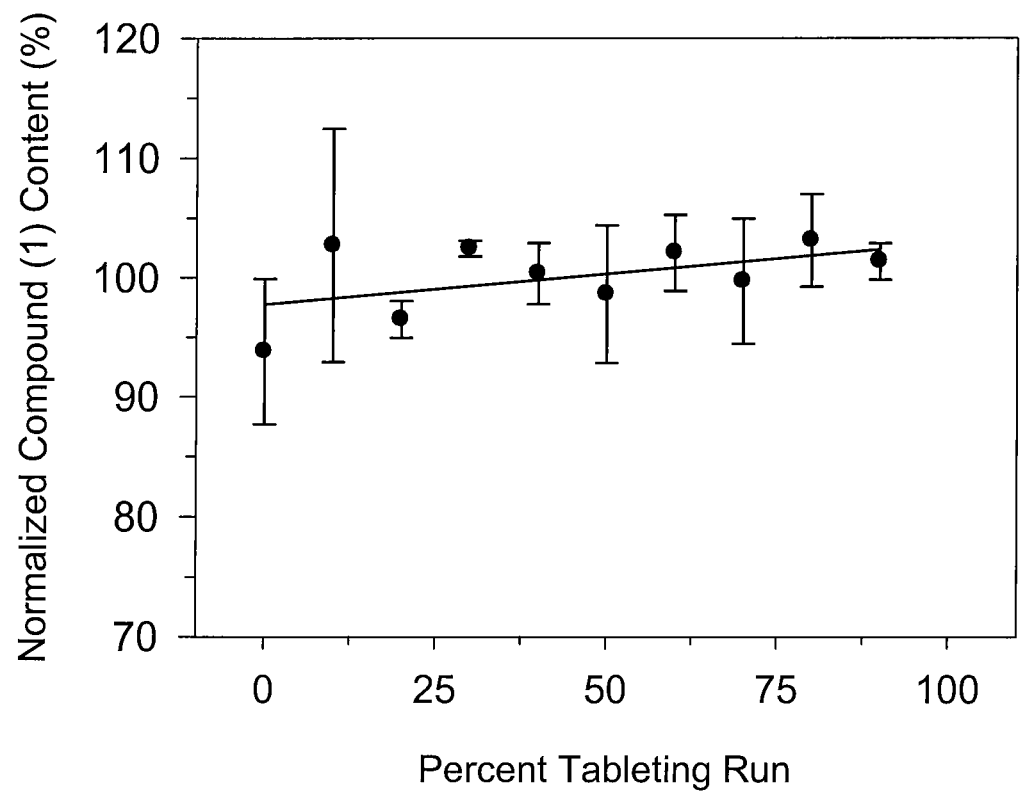
FIG. 14 shows tablet uniformity parameters for compound (1) in SR4 tablets prepared using an unstructured powder composition on a pilot scale.

The resulting histogram is presented in FIG. 14. FIG. 14 shows the tablet content of compound (1) normalized to the target content of compound (1) (±SD) at intervals during the total tableting run (100%). The slope of the linear regression fit to the data was +0.051. The relative standard deviation of compound (1) content throughout the batch of approximately 340,000 tablets was 4.94%.

Example 18

SR4 Tablets Prepared Using a Structured Powder Blend (Pilot Manufacturing Scale)

The following process was used to prepare 6 kg of a structured powder blend. Particles of A-TAB® were coated with compound (1) using the following procedure. First, 0.600 kg of A-TAB® was loaded into an 8 quart V-blender. Then, 0.350 kg of compound (1) was layered over the A-TAB®. 0.695 kg of additional A-TAB® was then applied as a layer over compound (1). The three-layer composition was then tumble-mixed in the blender at 25 rpm for 4 minutes. The resulting mixture was passed through a Quadro Comil Model 197 cone mill fitted with a screen having round openings with a diameter of 813 microns, a rectangular impeller, and an impeller spacer of 0.225 inches. The impeller was run at a speed of 2000 rpm. The mixture was scooped to the mill at a rate of about 0.3 kg per minute to produce compound (1) coated with A-TAB®.

Next, 1.000 kg of METHOCEL™ K4M DC and 0.063 kg of silicon dioxide were added to the 8 quart V-blender and mixed for 2 minutes at 25 rpm. The resulting hydroxypropylmethyl cellulose (HPMC) mixture was then passed through the cone mill using the same parameters as were used to prepare compound (1) coated with A-TAB®.

The HPMC mixture was then transferred to a 1 ft³ Lödige high-shear blender Gebrüder Lödige Maschinenbau GmbH, Paderborn, Del.). The mixture containing compound (1) was then applied as a layer over the HPMC mixture. Next, 1.309 kg of AVICEL® PH200, and 1.046 kg of EUDRAGIT® RLPO were added as layers to the blender. The resulting 4-layer mixture was blended at high shear for 5 minutes.

The resulting mixture was transferred to a 1 ft³ V-blender. Magnesium stearate (0.046 kg) that had been previously passed through a 40-mesh sieve was added to the mixture and blended for 4 minutes at 25 rpm. The mixture was discharged to a drum which completed the formation of the structured powder blend.

The resulting structured powder blend was compressed into tablets using a Kilian T100 fitted with 9 stations of 5/16 standard concave round punches and dies and a 2-paddle feeder in the feed frame. The turret of the press was run at 25 rpm and the paddle feeder was operated at 6 rpm. The blend was scooped to the hopper of the press. Tablets were compressed with a nominal target weight of 175 mg and nominal target compound (1) content of 10.0 mg. Hardness of the tablets was approximately 7 kp and tablet thickness was approximately 3.6 mm. The friability of the tablets was 0.3%.

Figure 15:
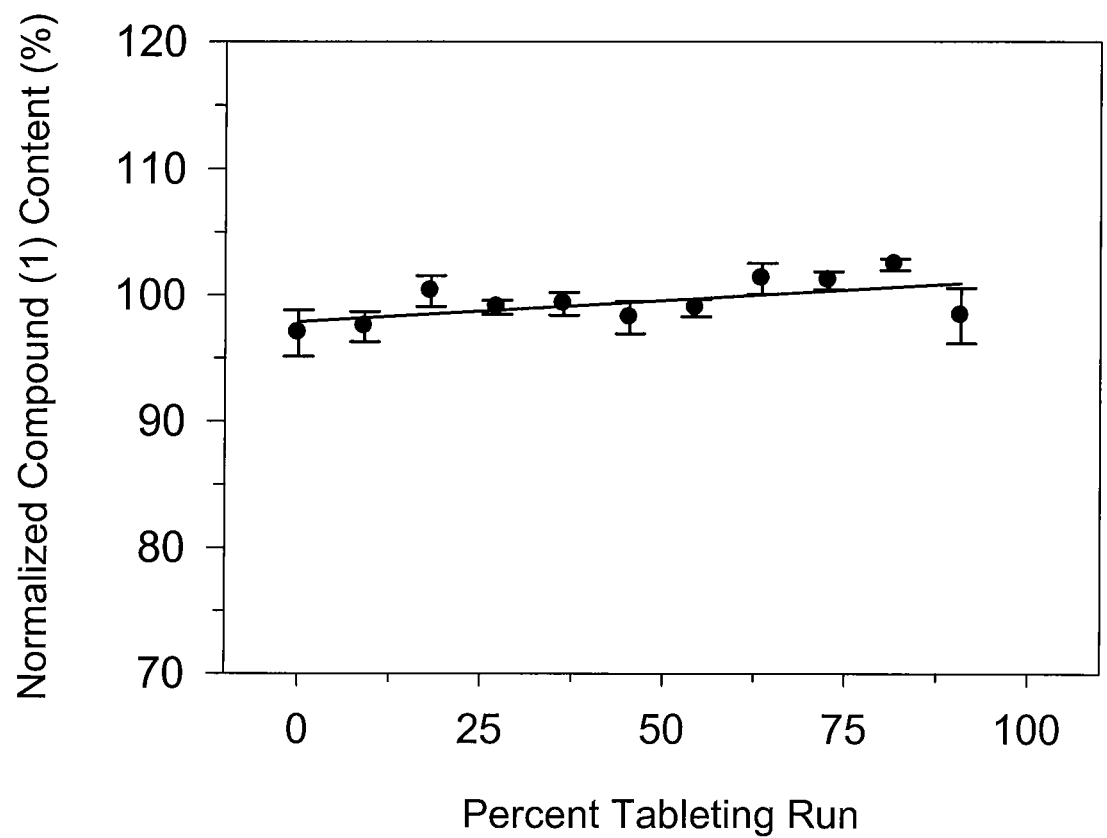
FIG. 15 shows tablet uniformity parameters for compound (1) in SR4 tablets prepared using an unstructured powder composition on a pilot scale.

Tablet samples were collected at intervals at approximately 3,375 tablets during the compression run. Three tablets were analyzed for compound (1) content at each of the collected intervals. The resulting data were plotted in the histogram presented in FIG. 15. FIG. 15 shows the tablet content of compound (1) normalized to the target content of compound (1) (±SD) at intervals during the total tableting run (100%). The slope of the linear regression to the data was +0.033 and the relative standard deviation was 1.95%.

The content uniformity in tablets manufactured with the unstructured powder blend as described in Example 17 compared to the uniformity of tablets manufactured from the structured powder blend described in Example 18 is summarized in Table 12. The closer the slope of the histogram is to zero, the more uniform the drug content from beginning to end of the batch. The smaller the relative standard deviation the more uniform the drug content is within the batch. The tablets manufactured from the structured powder blend show significantly better uniformity of compound (1) content by both measures.

Passing the blend of compound (1) and A-TAB® through a cone mill produced A-TAB® core particles coated with compound (1). These coated particles adhered to other components of the blend to form a three-dimensional structure that reduced segregation of the A-TAB®. High shear blending further reduced particle size and homogenized the blend.

TABLE 12

Tablet uniformity parameters.

| Uniformity Parameter | Unstructured Powder Blend | Structured Powder Blend |
|---|---|---|
| Slope | +0.051 | +0.033 |
| RSD (%) | 4.94 | 1.95 |

Example 19

Dissolution of SR4 Tablets Prepared Using a Structured Powder Blend

Tablets were prepared using a Korsch XL100 tablet press with round standard concave tooling at a pressure from 10 kN to 20 kN. The composition of SR4 tablets containing 10 mg, 20 mg, 30 mg, and 40 mg compound (1) is summarized in Table 13. The dissolution profiles for SR4 tablets are summarized in Table 14.

TABLE 13

Composition of SR4 tablets prepared using the Comil and high shear process.

| | SR4-10 | | SR4-20 | | SR4-30 | | SR4-40 | |
|---|---|---|---|---|---|---|---|---|
| | Tablet Geometry | | | | | | | |
| | 9/32-in | | 5/16-in | | 3/8-in | | 3/8-in | |
| Formulation Component | wt % | wt/tablet (mg) | wt % | wt/tablet (mg) | wt % | wt/tablet (mg) | wt % | wt/tablet (mg) |
| Compound (1) | 5.71 | 10.00 | 10.00 | 20.0 | 10.00 | 30.00 | 11.1 | 40.0 |
| AVICEL ® PH200 | 21.14 | 37.00 | 19.25 | 38.5 | 18.75 | 56.25 | 30.5 | 109.8 |
| METHOCEL ™-K4M (DC) | 32.91 | 57.59 | 32.90 | 65.8 | 32.90 | 98.70 | 23.6 | 85.0 |
| EUDRAGIT ® RLPO | 17.09 | 29.91 | 17.10 | 34.2 | 17.10 | 51.30 | 5.0 | 18.0 |
| Dibasic calcium phosphate, anhydrous | 21.34 | 37.40 | 19.00 | 38.0 | 19.00 | 57.00 | 27.8 | 100.0 |
| Mg stearate | 1.03 | 1.80 | 0.75 | 1.5 | 1.25 | 3.75 | 1.0 | 3.6 |
| Silicon dioxide | 0.74 | 1.31 | 1.00 | 2.0 | 1.00 | 1.00 | 1.0 | 3.6 |
| Total | 100.0 | 175.0 | 100.0 | 200.0 | 100.0 | 300.0 | 100.0 | 360.0 |

TABLE 14

Dissolution profiles for SR4 tablets.

| Time (hr) | SR4-10 Cumulative Release (wt %) (±SD) | SR4-20 Cumulative Release (wt %) (±SD) | SR4-30 Cumulative Release (wt %) (±SD) | SR4-40 Cumulative Release (wt %) (±SD) |
|---|---|---|---|---|
| 0 | 0 (0.0) | 0 (0.0) | 0 (0.0) | 0 (0.0) |
| 0.5 | 6 (0.3) | 3.5 (0.5) | 4 (0.2) | 6 (0.5) |
| 1 | 9 (0.5) | 5.7 (0.5) | 7 (0.4) | 9 (0.5) |
| 2 | 13 (0.7) | 9.2 (0.7) | 11 (0.5) | 14 (0.5) |
| 4 | 20 (1.0) | 15.5 (0.8) | 17 (0.7) | 21 (0.6) |
| 6 | 25 (1.2) | 20.8 (1.2) | 22 (0.7) | 27 (0.7) |
| 8 | 30 (1.3) | 26.5 (0.8) | 27 (0.8) | 32 (0.7) |
| 12 | 39 (1.3) | 35.8 (1.7) | 35 (0.9) | 41 (0.7) |
| 18 | 50 (1.1) | 48.5 (2.8) | 45 (1.1) | 52 (0.6) |

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A sustained release oral tablet dosage form comprising:
   dibasic calcium phosphate dihydrate or dibasic calcium phosphate anhydrous coated with about 5 to about 50 mg (3R)-4{[(1S)-2-methyl-1-(2-methylpropanoyloxy)propoxy]carbonylamino}-3-(4-chlorophenyl)butanoic acid or a pharmaceutically acceptable salt thereof;
   about 15 wt-% to about 40 wt-% microcrystalline cellulose;
   about 15 wt-% to about 40 wt-% hydroxypropylmethyl cellulose; and
   about 3 wt-% to about 30 wt-% of a release rate-controlling polymer
   based on the total weight of the dosage form;
   wherein the dosage form provides for sustained release of (3R)-4{[(1S)-2-methyl-1-(2-methylpropanoyloxy)propoxy]carbonylamino}-3-(4-chlorophenyl)butanoic acid or a pharmaceutically acceptable salt thereof during passage of the dosage form through the gastrointestinal tract.

2. The sustained release oral tablet dosage form of claim 1, wherein the release rate-controlling polymer is a copolymer comprising poly(ethyl acrylate, methyl methacrylate, trimethylammonioethyl methacrylate chloride) 1:2:0.2.

3. The sustained release oral tablet dosage form of claim 1, comprising about 0.5 wt-% to about 1.5 wt-% magnesium stearate, colloidal silicon dioxide, and dibasic calcium phosphate, anhydrous.

4. The sustained release oral tablet dosage form of claim 1, wherein the total weight of the dosage form is about 100 mg to about 600 mg.

5. The sustained release oral tablet dosage form of claim 1, wherein release of the (3R)-4{[(1S)-2-methyl-1-(2-methylpropanoyloxy)propoxy]carbonylamino}-3-(4-chlorophenyl)butanoic acid of pharmaceutically acceptable salt thereof from the oral dosage form exhibits an in vitro dissolution profile in 50 mM, pH 6.8 sodium phosphate buffer at 37° C. stirred at 75 rpm (USP, Type II) as follows:
   about 10% to about 30% of the (3R)-4{[(1S)-2-methyl-1-(2-methylpropanoyloxy)propoxy]carbonylamino}-3-(4-chlorophenyl)butanoic acid or pharmaceutically acceptable salt thereof is released within about 4 hours;
   about 15% to about 35% of the (3R)-4{[(1S)-2-methyl-1-(2-methylpropanoyloxy)propoxy]carbonylamino}-3-(4-chlorophenyl)butanoic acid or pharmaceutically acceptable salt thereof is released within about 8 hours;
   about 20% to about 50% of the (3R)-4{[(1S)-2-methyl-1-(2-methylpropanoyloxy)propoxy]carbonylamino}-3-(4-chlorophenyl)butanoic acid or pharmaceutically acceptable salt thereof is released within about 12 hours; and
   about 30% to about 80% of the (3R)-4{[(1S)-2-methyl-1-(2-methylpropanoyloxy)propoxy]carbonylamino}-3-(4-chlorophenyl)butanoic acid or pharmaceutically acceptable salt thereof is released within about 18 hours.

6. The sustained release oral tablet dosage form of claim 1, wherein release of the (3R)-4{[(1S)-2-methyl-1-(2-methylpropanoyloxy)propoxy]carbonylamino}-3-(4-chlorophenyl)butanoic acid or pharmaceutically acceptable salt thereof from the oral dosage form exhibits an in vitro dissolution profile in 50 mM, pH 6.8, sodium phosphate buffer at 37° C. stirred at 75 rpm (USP Type II) as follows:

about 10% to about 20% of the (3R)-4{[(1S)-2-methyl-1-(2-methylpropanoyloxy)propoxy]carbonylamino}-3-(4-chlorophenyl)butanoic acid or pharmaceutically acceptable salt thereof is released with about 4 hours;

about 20% to about 30% of the (3R)-4{[(1S)-2-methyl-1-(2-methylpropanoyloxy)propoxy]carbonylamino}-3-(4-chlorophenyl)butanoic acid or pharmaceutically acceptable salt thereof is released within about 8 hours;

about 25% to about 45% of the (3R)-4{[(1S)-2-methyl-1-(2-methylpropanoyloxy)propoxy]carbonylamino}-3-(4-chlorophenyl)butanoic acid or pharmaceutically acceptable salt thereof is released within about 12 hours; and about 35% to about 55% of the (3R)-4{[(1S)-2-methyl-1-(2-methylpropanoyloxy)propoxy]carbonylamino}-3-(4-chlorophenyl)butanoic acid or pharmaceutically acceptable salt thereof is released within about 18 hours.

7. The sustained oral tablet dosage form of claim 1, which following oral administration to sixteen healthy adult human patients at a dose of about 60 mg (3R)-4{[(1S)-2-methyl-1-(2-methylpropanoyloxy)propoxy]carbonylamino}-3-(4-chlorophenyl)butanoic acid provides a mean steady state pharmacokinetic profile characterized by: a $C_{ss,max}$ of about 202±56 ng/mL; a $T_{ss,max}$ of about 3.9±1.0 hours; a $C_{ss,12}$ of about 19 ng/mL; a $T_{ss,1/2}$ of about 10.9±3.8 hours; and an $AUC_{ss,24}$ of about 1803±420 ng·hr/mL.

8. The sustained release oral tablet dosage form of claim 1, which following oral administration to sixteen healthy adult human patients at a dose of about 60 mg (3R)-4{[(1S)-2-methyl-1-(2-methylpropanoyloxy)propoxy]carbonylamino}-3-(4-chlorophenyl)butanoic acid provides a mean steady state pharmacokinetic profile of R-3-amino-3-(4-cholorophenyl)butanoic acid in the blood of the patient characterized by a $C_{ss,max}/C_{ss,12}$ of about 8 to about 15.

9. The sustained release oral tablet dosage form of claim 1, having a friability less than about 0.5 wt-% determined according to USP 1216.

10. The sustained release oral tablet dosage form of claim 1, comprising
0.1 wt-% to 2 wt-% colloidal silicon dioxide; and
0.1 wt-% to 2 wt-% magnesium stearate.

11. The sustained release oral tablet dosage form of claim 1, comprising
0.1 wt-% to 2 wt-% colloidal silicon dioxide; and
0.1 wt-% to 2 wt-% magnesium stearate.

12. The sustained release oral tablet dosage form of claim 1, wherein the hydroxypropylmethyl cellulose comprises a hydroxypropoxy content of approximately 8 wt-%, a methoxy content of approximately 22 wt-%, a nominal viscosity in water at 2% concentration of approximately 4,000 centipoise, and a particle size such that at least 75 wt-% is less than 250 microns.

* * * * *